US011884653B2

(12) United States Patent
Davisson et al.

(10) Patent No.: US 11,884,653 B2
(45) Date of Patent: *Jan. 30, 2024

(54) ARYLNAPHTHALENE COMPOUNDS AS VACUOLAR-ATPASE INHIBITORS AND THE USE THEREOF

(71) Applicants: Purdue Research Foundation, West Lafayette, IN (US); Trustees of Boston University, Boston, MA (US)

(72) Inventors: Vincent Jo Davisson, West Lafayette, IN (US); Aaron Raymond Lindstrom, Lafayette, IN (US); Naoaki Fujii, West Lafayette, IN (US); Robert A. Davey, Boston, MA (US)

(73) Assignees: Purdue Research Foundation, West Lafayette, IN (US); Trustees of Boston University, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/223,106

(22) Filed: Apr. 6, 2021

(65) Prior Publication Data

US 2021/0230149 A1    Jul. 29, 2021

Related U.S. Application Data

(63) Continuation-in-part of application No. 16/982,354, filed as application No. PCT/US2019/022695 on Mar. 18, 2019.

(60) Provisional application No. 62/644,637, filed on Mar. 19, 2018.

(51) Int. Cl.
*C07D 405/04* (2006.01)
*C07D 407/04* (2006.01)

(52) U.S. Cl.
CPC .................. *C07D 407/04* (2013.01)

(58) Field of Classification Search
CPC .. C07D 405/04; C07D 405/14; A61K 31/352; A61K 31/365; A61P 31/14
See application file for complete search history.

(56) References Cited

U.S. PATENT DOCUMENTS 4,486,445 A * 12/1984 Patel ..................... C07D 407/10
549/299
2021/0060042 A1 * 3/2021 Zhang ................ A61K 31/7048

FOREIGN PATENT DOCUMENTS

WO    WO 2008/058897    *    5/2008
WO    WO 2019/182947    *    9/2019

OTHER PUBLICATIONS

STN Registry 1222800-74-9 (2010).*
STN Registry 340827-04-5 (2001).*
Lindstrom et al., Phenotypic Prioritization of Diphyllin Derivatives That Block Filoviral Cell Entry by Vacuolar (H+)-ATPase Inhibition, ChemMedChem (2018) 13, pp. 2664-2676.*
Kostova et al., CAPLUS Abstract 132:345480 (2000).*
Yu et al., Synthesis and bioevaluation of novel analogues of justicidin A, Med Chem Res. 19, pp. 71-76 (2010).*
Fan et al., CAPLUS Abstract 160:158962 (2013), pp. 664-668.*
Zhao et al., CAPLUS Abstract 159:577162 (2013), pp. 675-690.*
Bosseray et al., PubMed Abstract (Pathol Biol (Paris) 50(8): 483-92), 2002.*
Douglas, Jr., Introduction to Viral Diseases, Cecil Textbook of Medicine, 20th Edition, vol. 2, pp. 1739-1747 (1996).*
Goff, PubMed Abstract (J Gene Med 3(6): 517-28), 2001.*
Razonable et al., PubMed Abstract (Herpes 10(3): 60-5), 2003.*

* cited by examiner

*Primary Examiner* — Deepak R Rao
(74) *Attorney, Agent, or Firm* — Schwegman Lundberg & Woessner, P.A.

(57) ABSTRACT

Ebola virus and Marburg virus are filoviruses and are responsible for outbreaks that cause up to 90% fatality, including the recent outbreak in West Africa that has resulted in over 11,000 deaths. The present disclosure generally relates to series novel arylnaphthalene compounds, having a formula (I) or a pharmaceutically acceptable salt thereof, as a vacuolar-ATPase inhibitor that are useful for the treatment for a broad spectrum of viral infections, including those infections caused by filoviruses. Pharmaceutical composition matters and methods of use are within the scope of this invention.

14 Claims, 3 Drawing Sheets

ARYLNAPHTHALENE COMPOUNDS AS VACUOLAR-ATPASE INHIBITORS AND THE USE THEREOF

CROSS REFERENCE TO RELATED APPLICATIONS

This present patent application is a continuation-in-part application of U.S. Utility patent application Ser. No. 16/982,354, filed Sep. 18, 2020, which is a national stage application under 35 U.S.C. § 371(c) of International Application No. PCT/US19/22695, filed on Mar. 18, 2019, which relates to and claims the priority under 35 U.S.C. § 119(e) to U.S. Provisional Patent Application Ser. No. 62/644,637 filed on Mar. 19, 2018, the contents of which are hereby incorporated by reference in their entirety into the present disclosure.

STATEMENT OF U.S. GOVERNMENT SUPPORT

This invention was made with government support under AI128364 awarded by the National Institutes of Health. The government has certain rights in the invention.

TECHNICAL FIELD

The present disclosure generally relates to new compounds for therapeutic uses. In particular, this disclosure relates to novel arylnaphthalene compounds as a vacuolar-ATPase inhibitor that are useful for the treatment of various viral infections.

BACKGROUND

This section introduces aspects that may help facilitate a better understanding of the disclosure. Accordingly, these statements are to be read in this light and are not to be understood as admissions about what is or is not prior art.

Filoviruses are highly contagious, lethal viruses that cause severe hemorrhagic fever in humans and primates (Ansari, A A, *J. Autoimmun.* 2014, 55, 1-9; Messaoudi, I., et al, *Nat. Rev. Microbiol.* 2015, 13(11), 663-676; White, J M, et al., *Nat. Rev. Microbiol.* 2012, 10(5), 317-322). They are negative-strand RNA, filamentous viruses that group into 3 families named Ceuvavirus, Ebolaviruses (EBOV) and Marburgviruses (MARV). Viruses from the latter two families are responsible for outbreaks that have up to 90% fatality, including the recent outbreak in West Africa that resulted in over 28,000 reported cases and 11,317 deaths according to the WHO. Currently, there are no approved therapeutic measures for the treatment of filovirus infections but the development of a vaccine is being prioritized by the FDA and a promising viral polymerase inhibitor has also recently advanced in development (Sheahan, T P, et al., *Sci. Transl. Med.* 2017, 9, eaal3653). There are unmet needs in fighting those viral infections.

BRIEF SUMMARY OF INVENTION

The present invention generally relates to new compounds for therapeutic uses. In particular, this disclosure relates to novel arylnaphthalene compounds as a vacuolar-ATPase inhibitor that are useful for treatment of various viral infections.

Also described herein are pharmaceutical compositions of such compounds and methods for treating a viral infection by administering therapeutically effective amounts of such compound alone or in a pharmaceutical composition.

In some illustrative embodiments, the present invention relates to a compound having the formula (I)

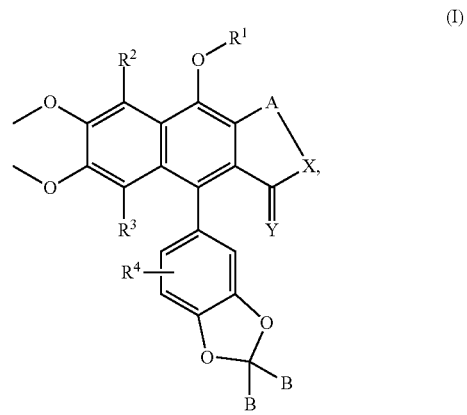

(I)

or a pharmaceutically acceptable salt thereof, wherein
A is $C=O$, $CR_2$, $CH_2$, CHR, O, S, NH, NR, wherein R is an alkyl;
B is hydrogen (H), deuterium (D), or fluorine (F);
X is $C=O$, $CR_2$, $CH_2$, CHR, O, S, NH, NR, wherein R is an alkyl;
Y is O, $CF_2$, $CH_2$, CHR, S, NH, NR, wherein R is an alkyl;
$R^1$ is hydrogen, an alkyl, alkylamide, alkenyl, alkenylamide, alkenylamino, alkynyl, alkynylamide, alkynylamino, heteroalkyl, heteroalkenyl, heteroalkynyl, heterocyclyl, cycloalkyl, cycloalkenyl, cycloheteroalkyl, cycloheteroalkenyl, acyl, aryl, heteroaryl, arylalkyl, arylalkenyl, or arylalkynyl; and
$R^2$, $R^3$, and $R^4$ are each independently selected from the group consisting of hydrogen, deuterium, —CN, —$CF_3$, and a halo.

In some illustrative embodiments, the present invention relates to a compound having the formula (I), wherein $R^1$ is

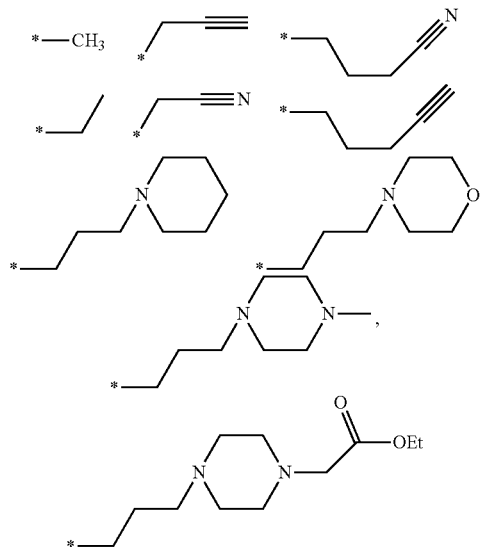

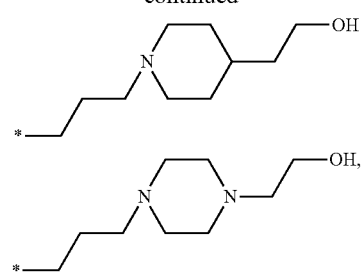
—CH$_2$CH$_2$O(CH$_2$)nR$^7$, —CH$_2$CH$_2$CH$_2$O(CH$_2$)nR$^7$, —CH$_2$CH$_2$CH$_2$CH$_2$O(CH$_2$)nR$^7$, —CH$_2$(CH$_2$)nR$^7$, or, wherein n=1~4 and
R$^7$ is
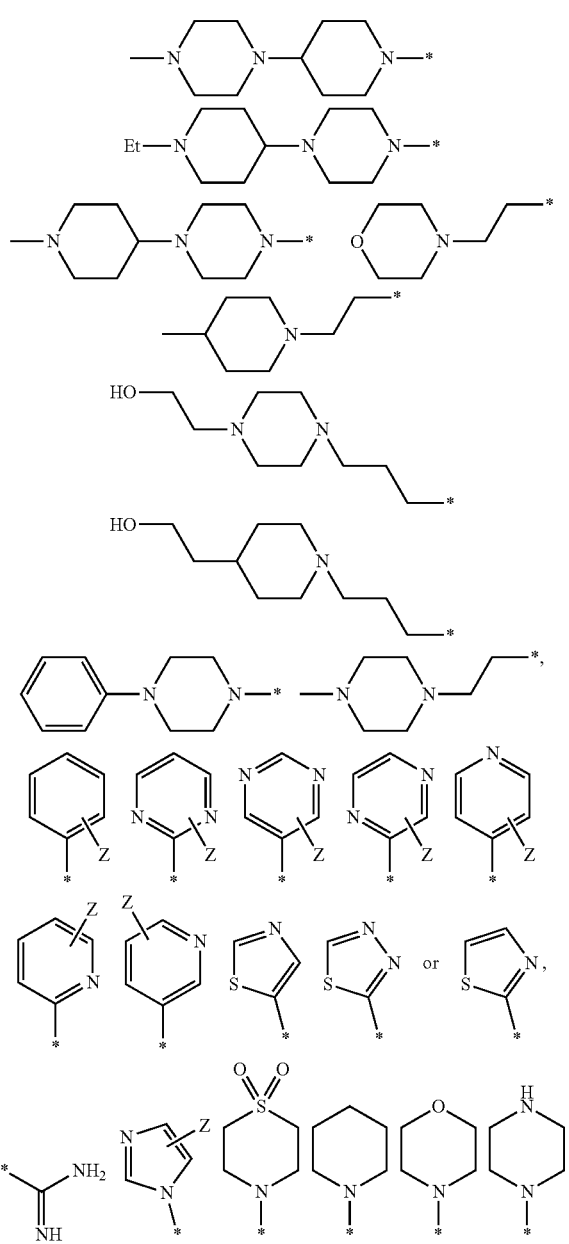
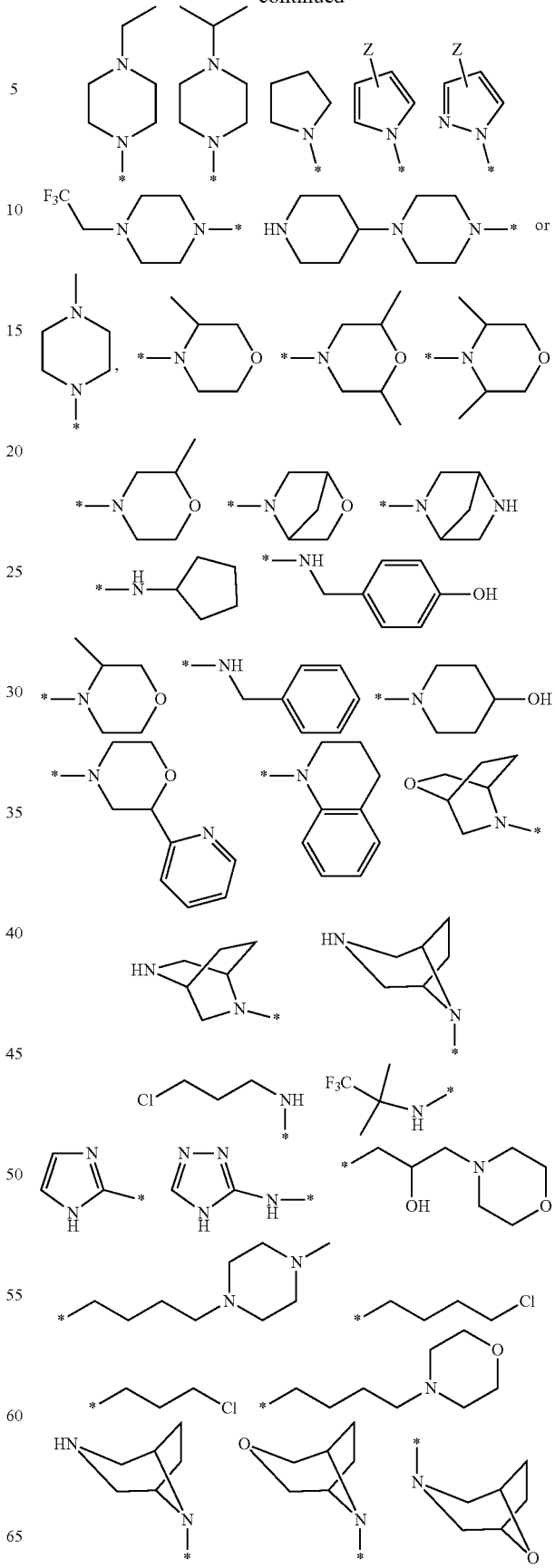

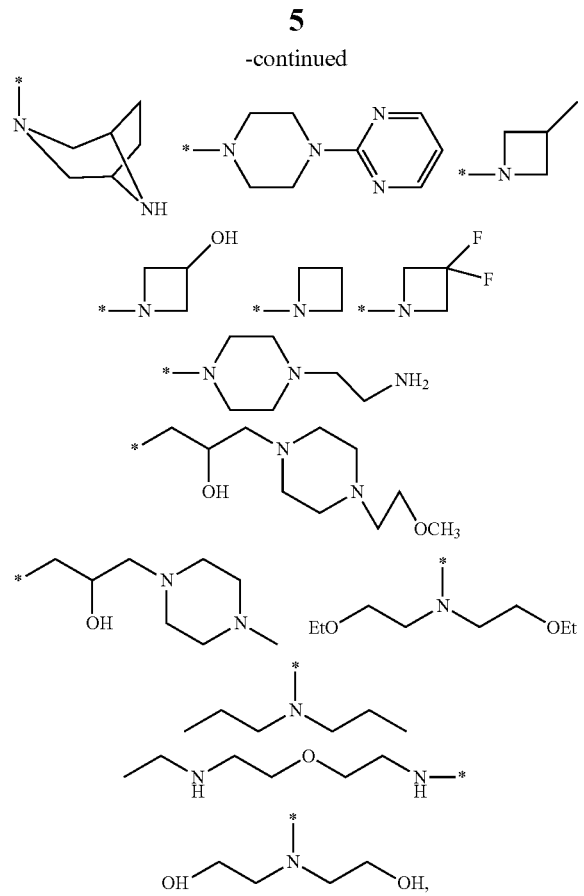

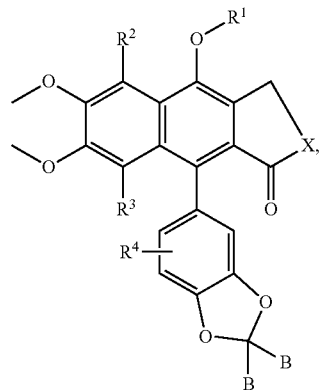

wherein Z is a halogen, C1~C3 alkyl, —CF$_3$, —CN, or —CONR$_2$, wherein R is hydrogen or a C1~C3 alkyl, and * represents site of attachment.

In some illustrative embodiments, the present invention relates to a compound having the formula (II):

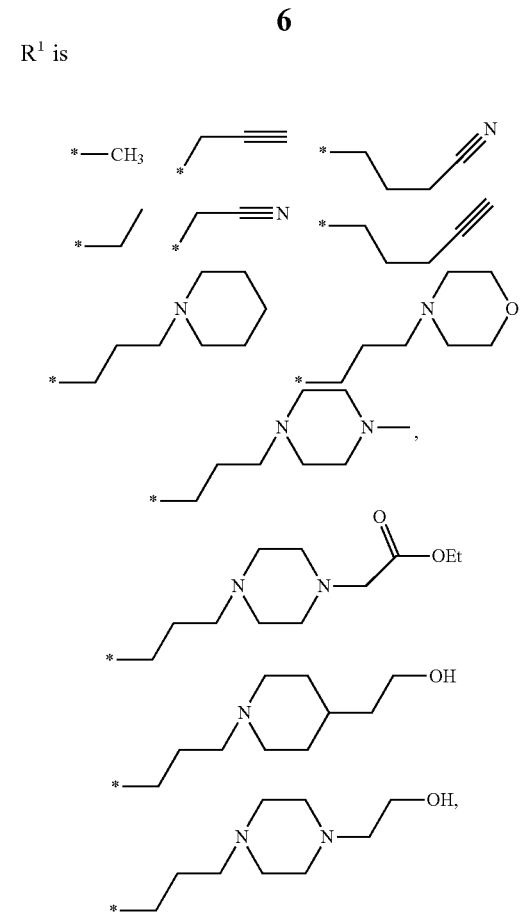

(II)

or a pharmaceutically acceptable salt thereof, wherein
B is hydrogen (H), deuterium (D), or fluorine (F);
X is CR$_2$, CH$_2$, CHR, O, S, NH, NR, wherein R is an alkyl;
R$^2$, R$^3$, and R$^4$ are each independently selected from the group consisting of hydrogen, deuterium, —CN, —CF$_3$, and a halo; and R$^1$ is

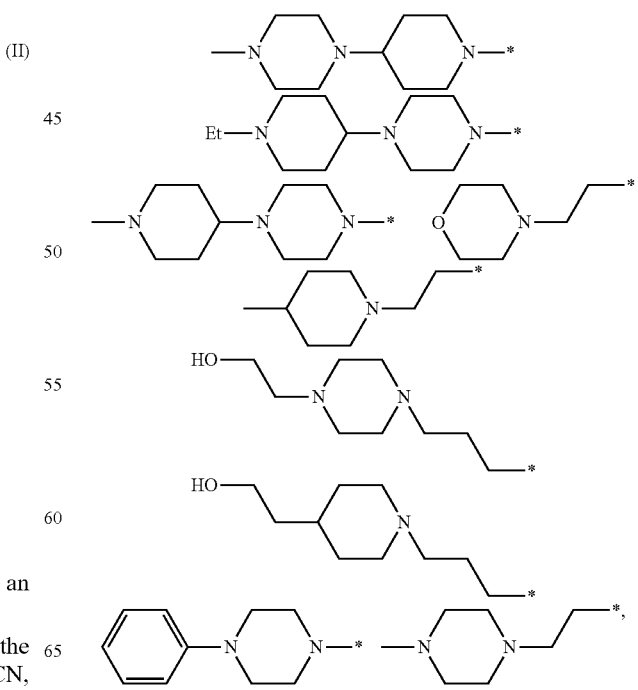

—CH$_2$CH$_2$O(CH$_2$)nR$^7$, —CH$_2$CH$_2$CH$_2$O(CH$_2$)nR$^7$, —CH$_2$CH$_2$CH$_2$CH$_2$O(CH$_2$)nR$^7$, —CH$_2$(CH$_2$)nR$^7$, or, wherein n=1~4 and
R$^7$ is

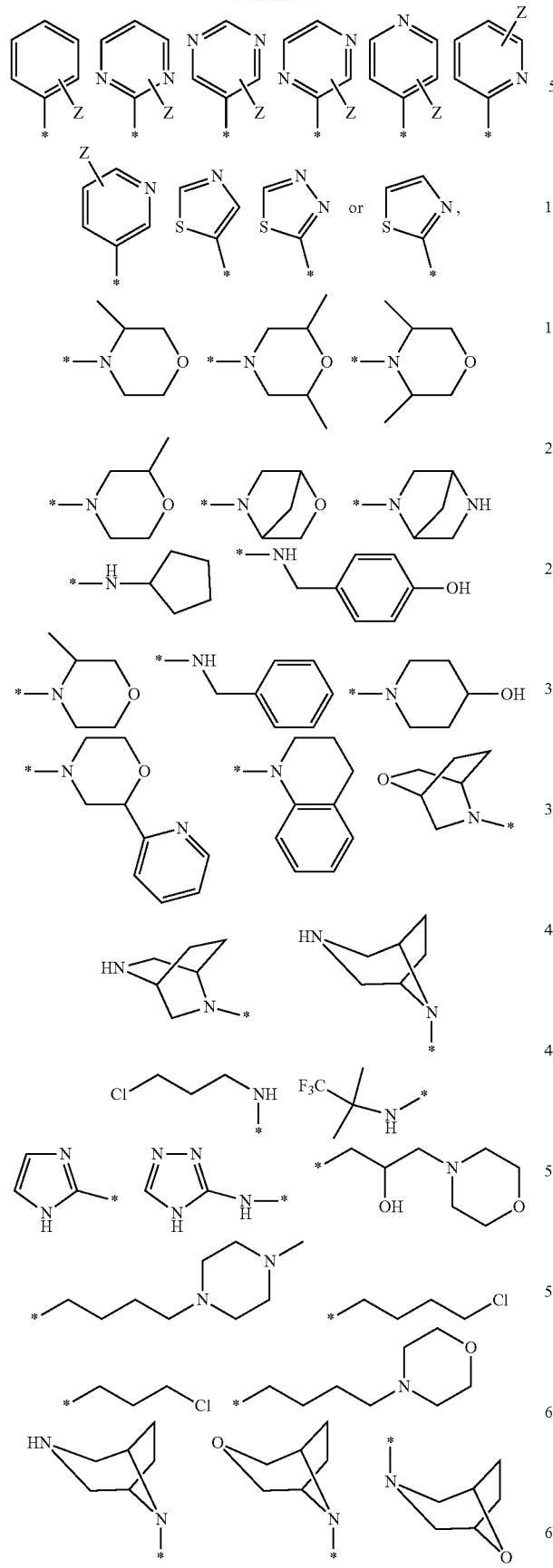
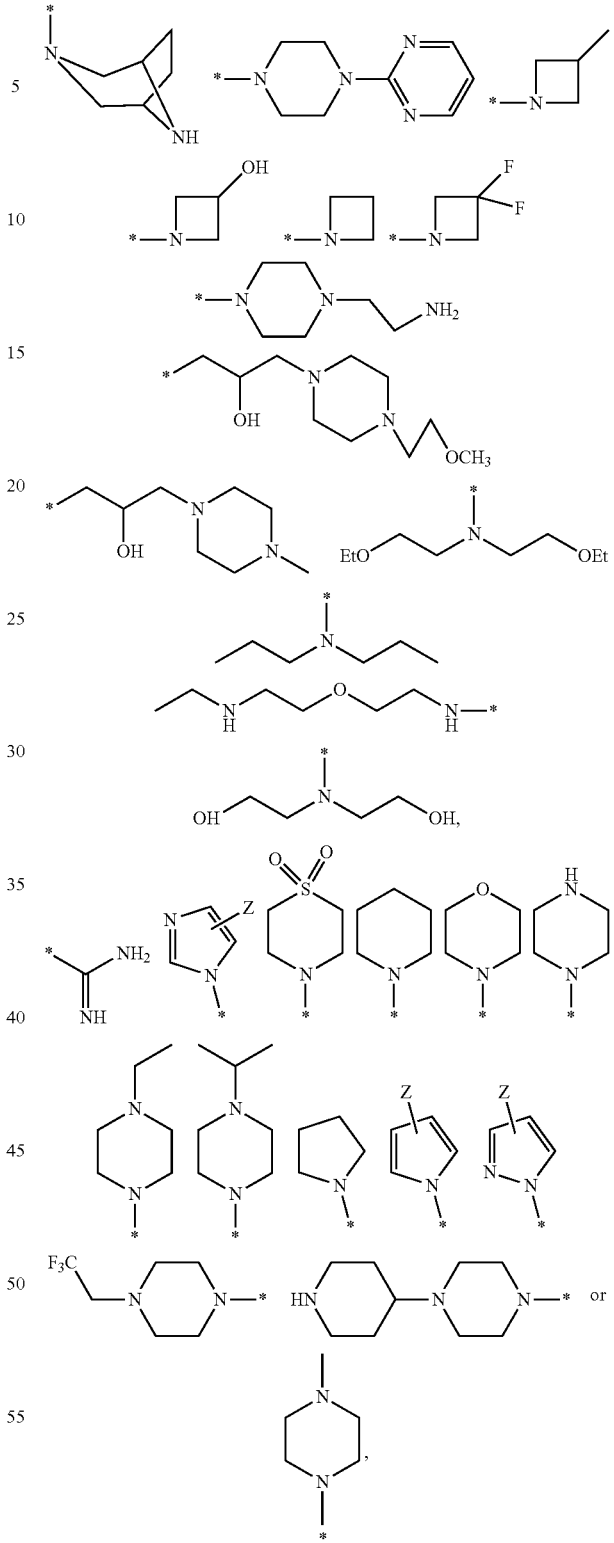
wherein Z is a halogen, C1~C3 alkyl, —CF$_3$, —CN, or —CONR$_2$, wherein R is hydrogen or a C1~C3 alkyl, and * represents site of attachment.
In some illustrative embodiments, the present invention relates to a compound having the formula (III),

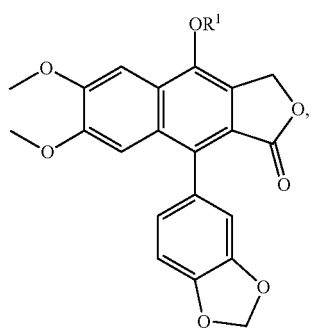
(III)
wherein R¹ is selected from the group consisting of
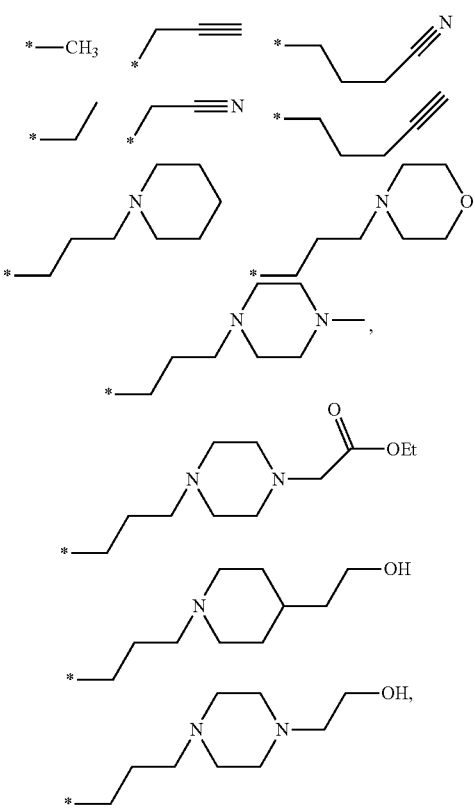
—CH₂CH₂O(CH₂)nR⁷, —CH₂CH₂CH₂O(CH₂)nR⁷, —CH₂CH₂CH₂CH₂O(CH₂)nR⁷, —CH₂(CH₂)nR⁷, or, wherein n=1~4 and
  R⁷ is
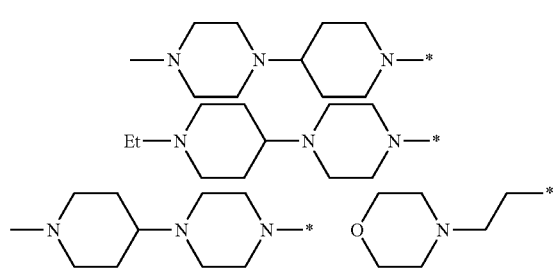
-continued
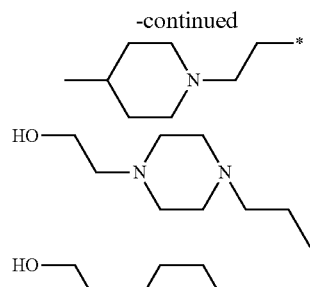
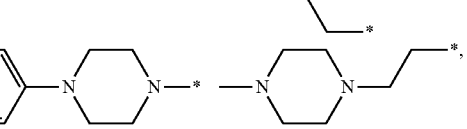
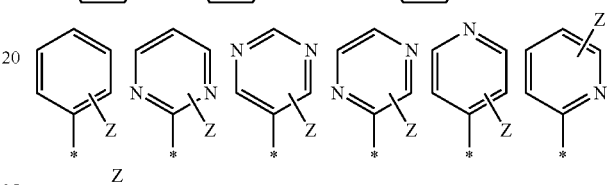
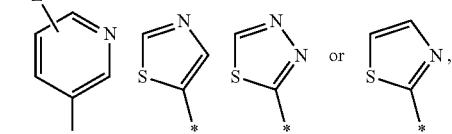
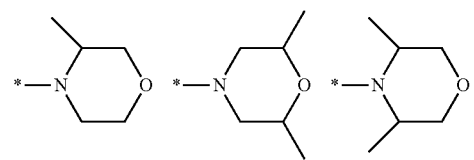
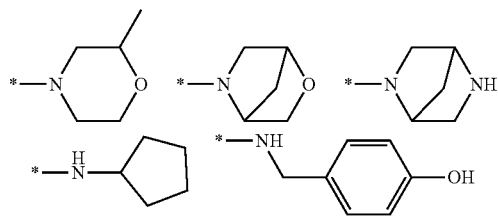
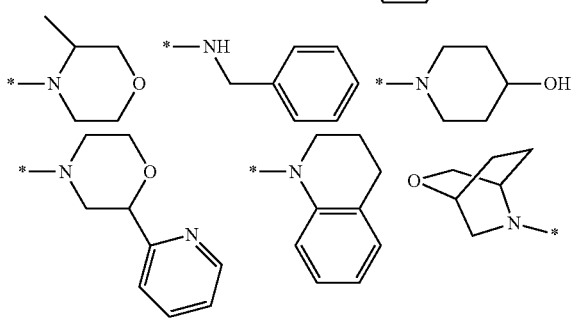
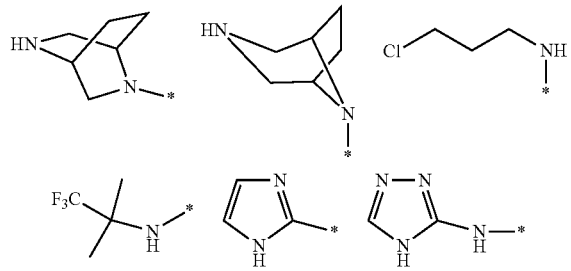

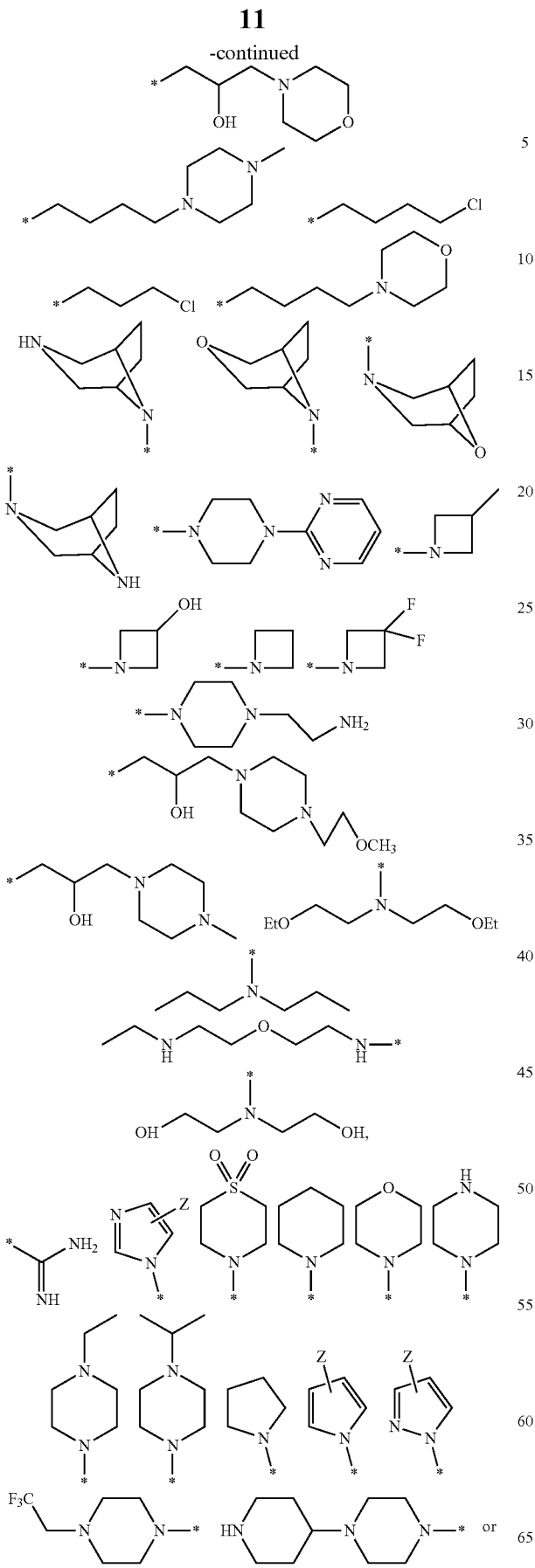
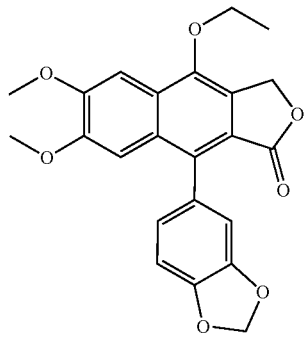
wherein Z is a halogen, C1~C3 alkyl, —CF$_3$, —CN, or —CONR$_2$, wherein R is hydrogen or a C1~C3 alkyl, and * represents site of attachment.
In some illustrative embodiments, the present invention relates to a compound having the formula (I), wherein said compound has the following structure:
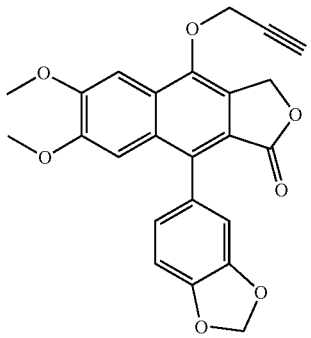
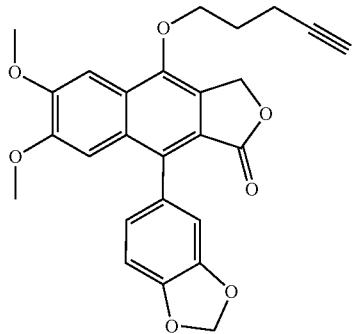

-continued

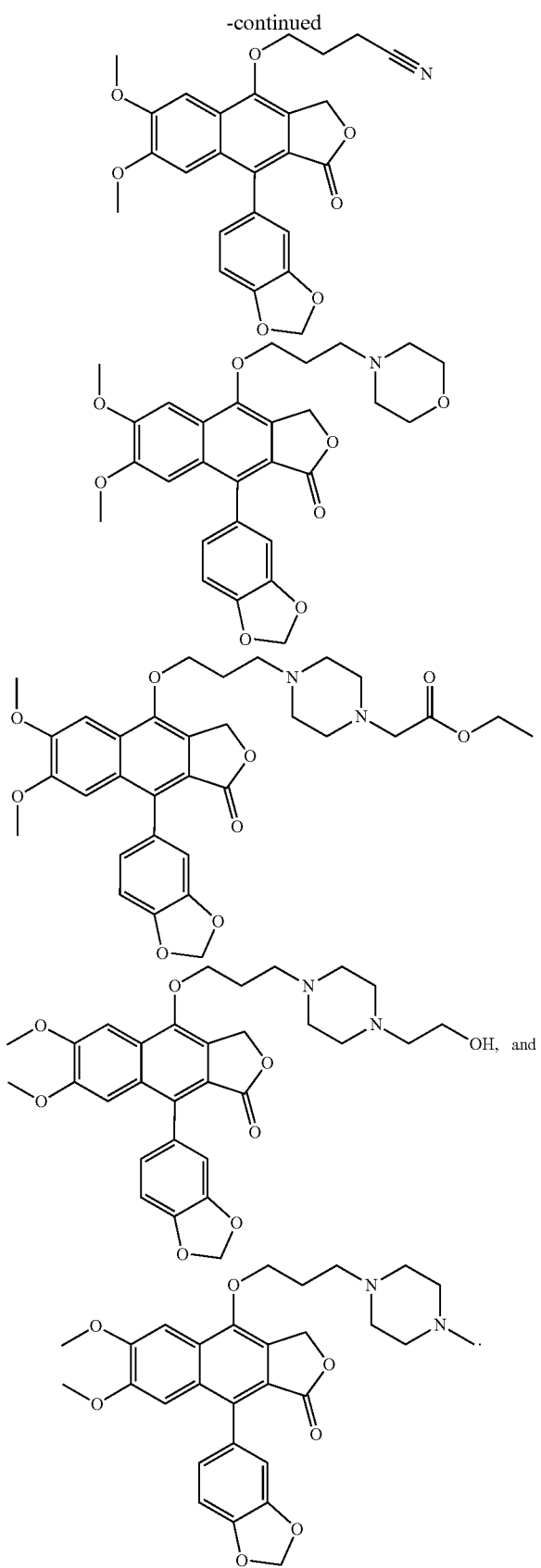

In some illustrative embodiments, the present invention relates to a pharmaceutical composition comprising one or more compounds having the formulae (I), (II), or (III) as disclosed herein, or a pharmaceutically acceptable salt thereof, together with one or more diluents, excipients or carriers.

In some illustrative embodiments, the present invention relates to a compound having the formulae (I), (II), or (III) as disclosed herein, or a pharmaceutically acceptable salt thereof, wherein the compound is an antiviral agent.

In some illustrative embodiments, the present invention relates to a compound having the formulae (I), (II), or (III) as disclosed herein, or a pharmaceutically acceptable salt thereof, wherein the compound is an antiviral agent for the treatment of a viral infection by flaviviridae viruses, including Dengue virus, West Nile virus, Yellow fever virus, Japanese encephalitis virus, Powassan virus, Zika virus, and Usutu virus; respiratory viruses, including MERS coronavirus, Influenza A H1N1 virus, Respiratory syncytial virus; Arenaviridae virus, including Tacaribe virus, Pichinde virus, Junin virus, Lassa fever virus, Lymphocytic Choriomeningitis virus; Filoviridae virus, including Ebolavirus, Marburgvirus; Togaviridae virus, including Venezuelan equine encephalitis virus, Eastern equine encephalitis virus, Western equine encephalitis virus, and Chikungunya virus; Mayarovirus; and Hantavirus.

In some illustrative embodiments, the present invention relates to a method for treating a patient with a viral infection, comprising the step of administering a therapeutically effective amount of one or more compounds having the formulae (I), (II), or (III) as disclosed herein, or a pharmaceutically acceptable salt thereof, and one or more carriers, diluents, or excipients, to a patient in need of relief from said infection.

In some illustrative embodiments, the present invention relates to a method for treating a patient with an infection, comprising the step of administering a therapeutically effective amount of one or more compounds, together with one or more carriers, diluents, or excipients, to a patient in need of relief from said infection, the compound having formula (I):

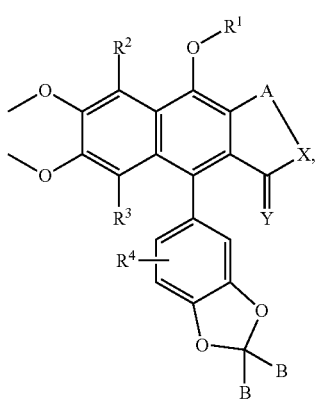

(I)

or a pharmaceutically acceptable salt thereof, wherein
A is C=O, CR$_2$, CH$_2$, CHR, O, S, NH, NR, wherein R is an alkyl;
B is hydrogen (H), deuterium (D), or fluorine (F);
X is C=O, CR$_2$, CH$_2$, CHR, O, S, NH, NR, wherein R is an alkyl;
Y is O, CF$_2$, CH$_2$, CHR, S, NH, NR, wherein R is an alkyl;

R[1] is hydrogen, an alkyl, alkylamide, alkenyl, alkenylamide, alkenylamino, alkynyl, alkynylamide, alkynylamino, heteroalkyl, heteroalkenyl, heteroalkynyl, heterocyclyl, cycloalkyl, cycloalkenyl, cycloheteroalkyl, cycloheteroalkenyl, acyl, aryl, heteroaryl, arylalkyl, arylalkenyl, or arylalkynyl; and R[2], R[3], and R[4] are each independently selected from the group consisting of hydrogen, deuterium, —CN, —CF$_3$, and a halo.

In some illustrative embodiments, the present invention relates to a method for treating a patient with an infection, comprising the step of administering a therapeutically effective amount of one or more compounds, together with one or more carriers, diluents, or excipients, to a patient in need of relief from said infection, wherein said compound has a formula

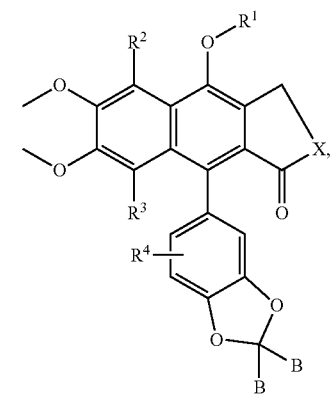

(II)

or a pharmaceutically acceptable salt thereof, wherein
B is hydrogen (H), deuterium (D), or fluorine (F);
X is CR$_2$, CH$_2$, CHR, O, S, NH, NR, wherein R is an alkyl;
R[2], R[3], and R[4] are each independently selected from the group consisting of hydrogen, deuterium, —CN, —CF$_3$, and a halo; and
R[1] is

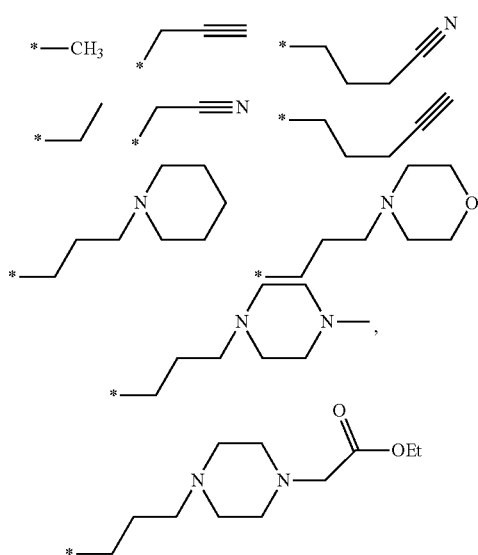

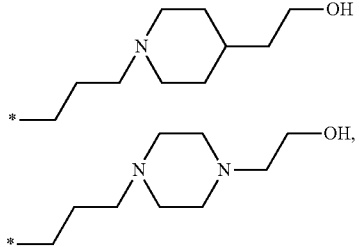

—CH$_2$CH$_2$O(CH$_2$)nR[7], —CH$_2$CH$_2$CH$_2$O(CH$_2$)nR[7], —CH$_2$CH$_2$CH$_2$CH$_2$O(CH$_2$)nR[7], —CH$_2$(CH$_2$)nR[7], or, wherein n=1~4 and
R[7] is

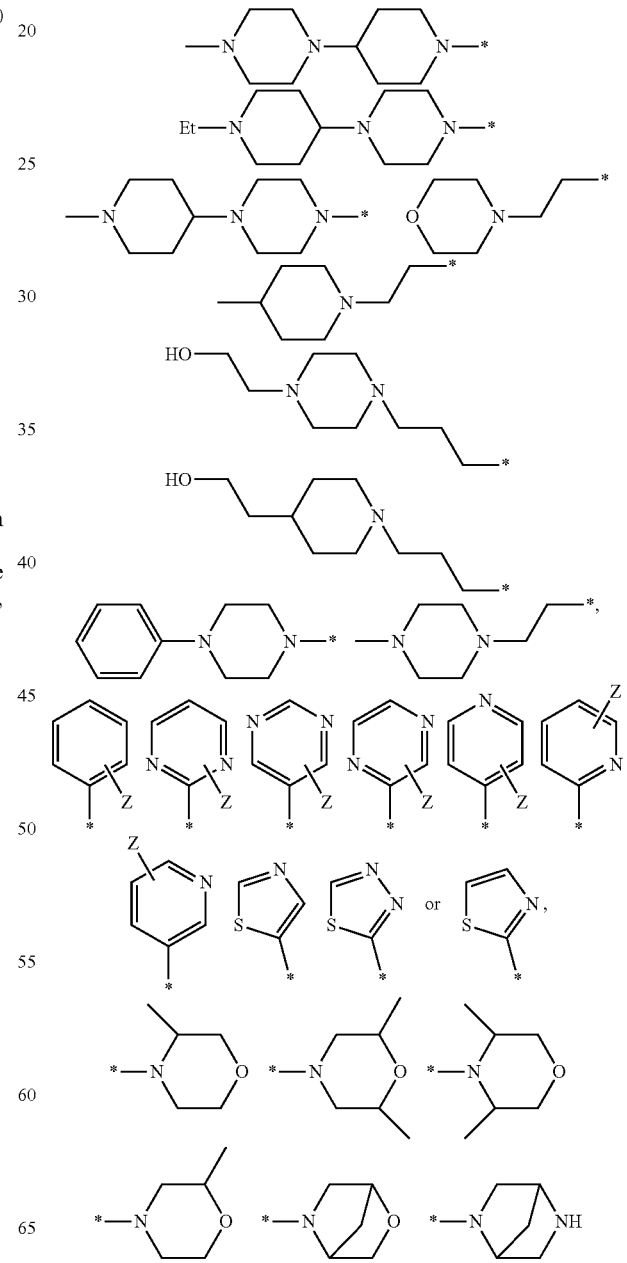

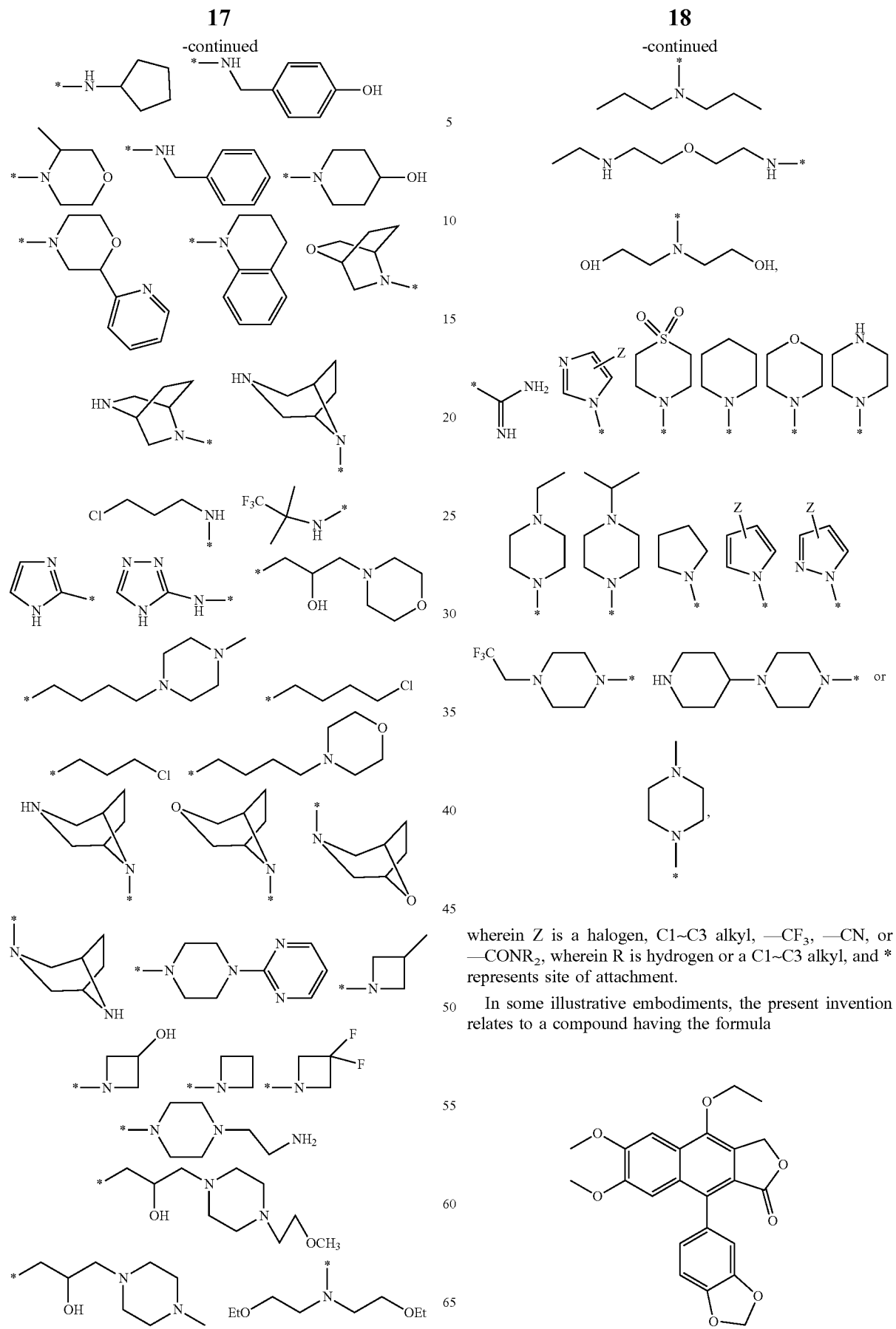
wherein Z is a halogen, C1~C3 alkyl, —CF₃, —CN, or —CONR₂, wherein R is hydrogen or a C1~C3 alkyl, and * represents site of attachment.
In some illustrative embodiments, the present invention relates to a compound having the formula 19
-continued
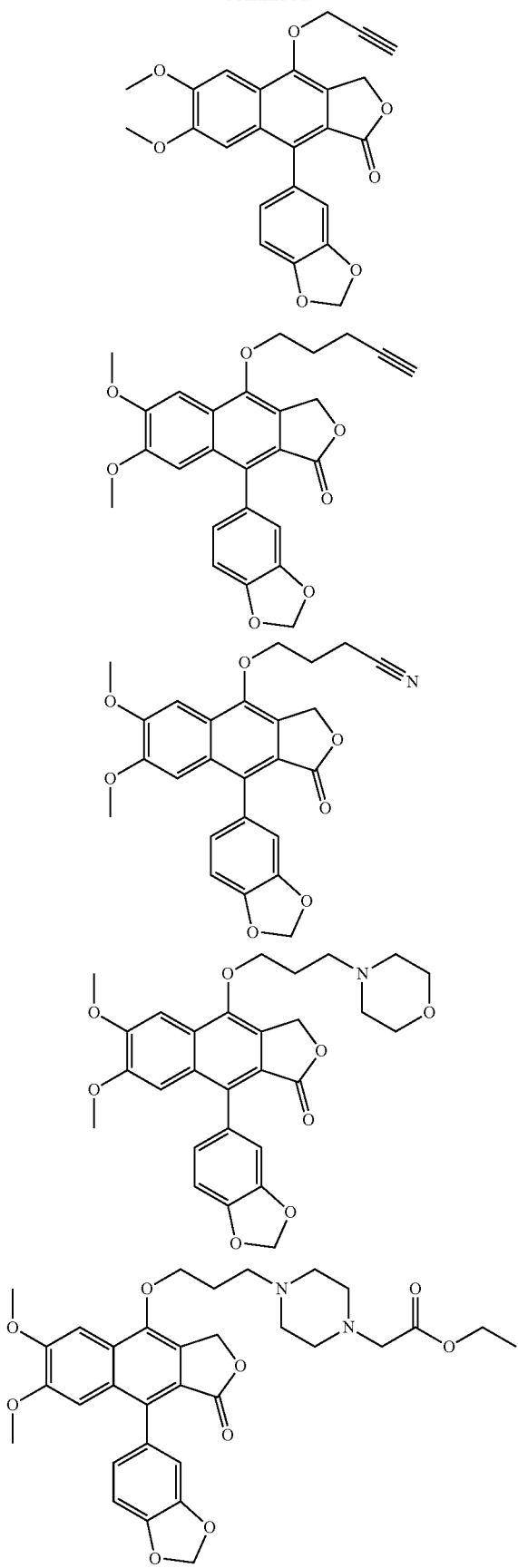
20
-continued
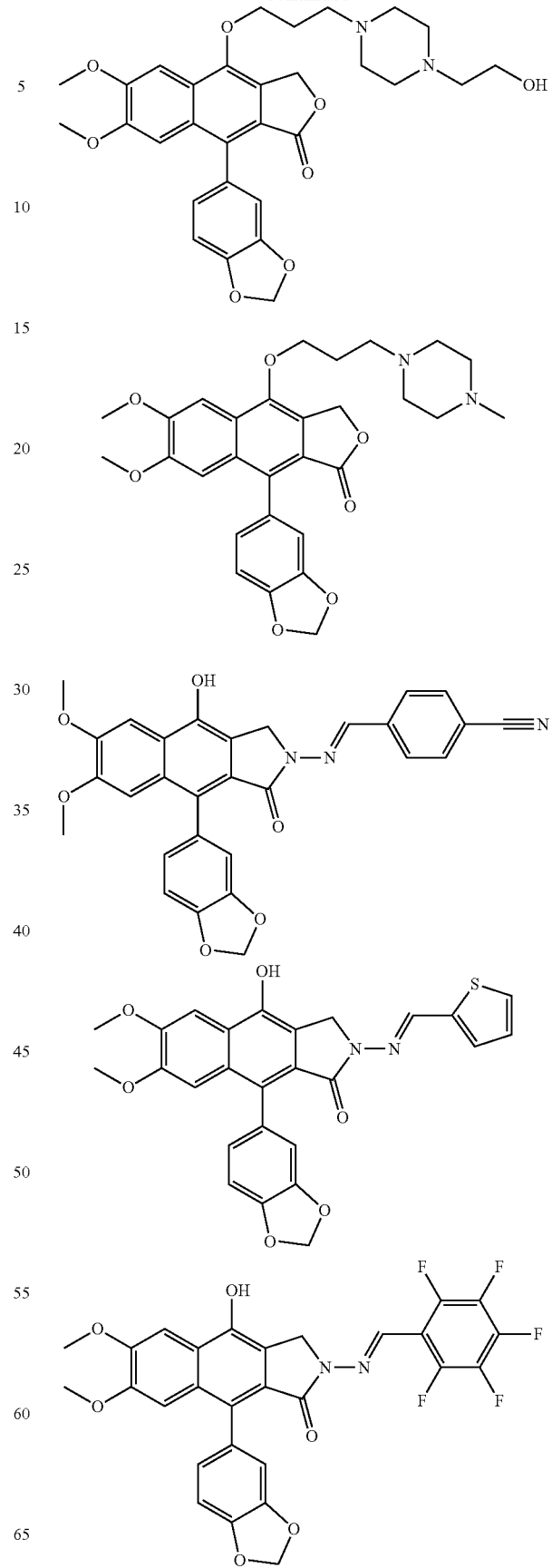

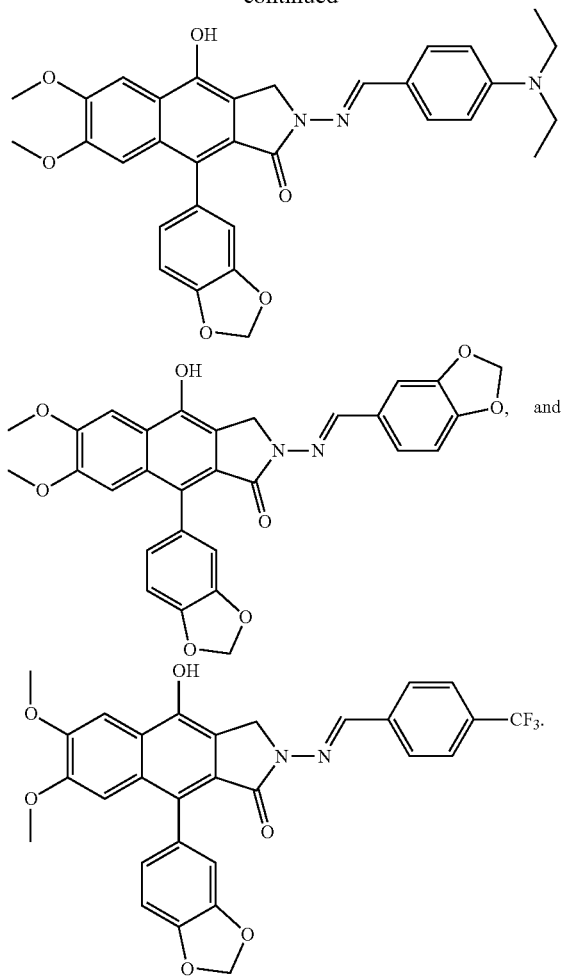

In some other illustrative embodiments, the present invention relates to a pharmaceutical composition comprising one or more compounds disclosed herein, or a pharmaceutically acceptable salt thereof, together with one or more diluents, excipients or carriers.

In some illustrative embodiments, the present invention relates to compounds disclosed herein, wherein the compounds are an antiviral agent.

In some other illustrative embodiments, the present invention relates to one or more compounds disclosed herein, wherein the compounds are an antiviral agent for the treatment of a viral infection by flaviviridae viruses, including Dengue virus, West Nile virus, Yellow fever virus, Japanese encephalitis virus, Powassan virus, Zika virus, and Usutu virus; respiratory viruses, including MERS coronavirus, Influenza A H1N1 virus, Respiratory syncytial virus; Arenaviridae virus, including Tacaribe virus, Pichinde virus, Junin virus, Lassa fever virus, Lymphocytic Choriomeningitis virus; Filoviridae virus, including Ebolavirus, Marburgvirus; Togaviridae virus, including Venezuelan equine encephalitis virus, Eastern equine encephalitis virus, Western equine encephalitis virus, and Chikungunya virus; Mayarovirus; and Hantavirus.

In some other illustrative embodiments, the present invention relates to a method for treating a patient with a viral infection, wherein said method comprises the step of administering a therapeutically effective amount of one or more compounds disclosed herein, and one or more carriers, diluents, or excipients, to a patient in need of relief from said infection.

In some other illustrative embodiments, the present invention relates to a method for treating a patient with a viral infection, wherein said method comprises the step of administering a therapeutically effective amount of a compound disclosed herein in combination with one or more other compounds of the same or different mode of action, and one or more carriers, diluents, or excipients, to a patient in need of relief from said viral infection.

In some illustrative embodiments, the present invention relates to a drug conjugate, wherein the drug conjugate comprises one or more compounds disclosed herein, wherein the conjugate confers cell-type or tissue type targeting or the conjugate targets another pathway that synergizes the action of compounds disclosed herein.

In some other illustrative embodiments, the present invention relates to a pharmaceutical composition comprising nanoparticles of one or more compounds disclosed herein, together with one or more diluents, excipients or carriers.

In some other illustrative embodiments, the present invention relates to a method for treating a patient with an infection comprising the step of administering a therapeutically effective amount of one or more compounds according formula (III), together with one or more carriers, diluents, or excipients, to a patient in need of relief from said infection, wherein said infection is a viral infection.

In some other illustrative embodiments, the present invention relates to a method for treating a patient with an infection comprising the step of administering a therapeutically effective amount of one or more compounds according formula (III), together with one or more carriers, diluents, or excipients, to a patient in need of relief from said infection, wherein said viral infection is an infection by flaviviridae viruses, including Dengue virus, West Nile virus, Yellow fever virus, Japanese encephalitis virus, Powassan virus, Zika virus, and Usutu virus; respiratory viruses, including MERS coronavirus, Influenza A H1N1 virus, Respiratory syncytial virus; Arenaviridae virus, including Tacaribe virus, Pichinde virus, Junin virus, Lassa fever virus, Lymphocytic Choriomeningitis virus; Filoviridae virus, including Ebolavirus, Marburgvirus; Togaviridae virus, including Venezuelan equine encephalitis virus, Eastern equine encephalitis virus, Western equine encephalitis virus, and Chikungunya virus; Mayarovirus; and Hantavirus.

In some other illustrative embodiments, the present invention relates to a method for treating a patient with an infection comprising the step of administering a therapeutically effective amount of one or more compounds together with one or more carriers, diluents, or excipients, to a patient in need of relief from said infection, wherein said compound is

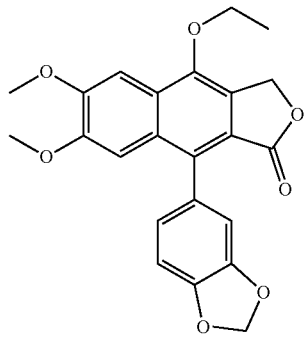

23
-continued
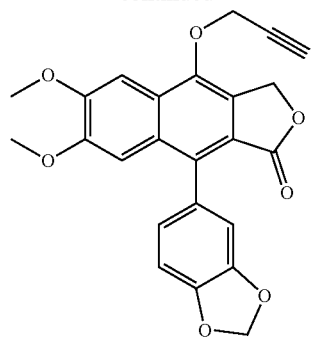
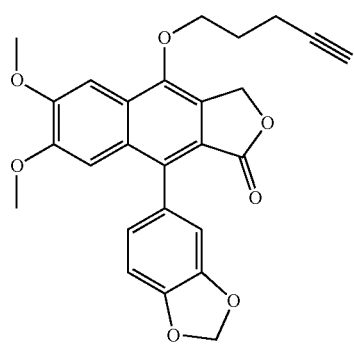
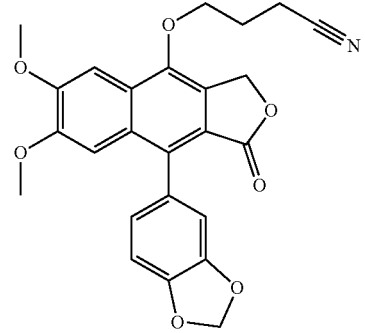
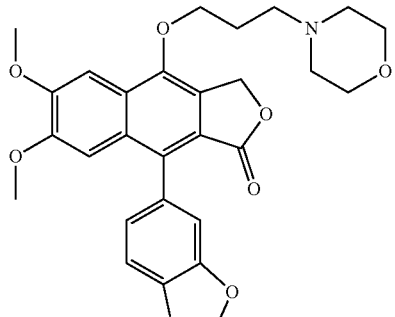
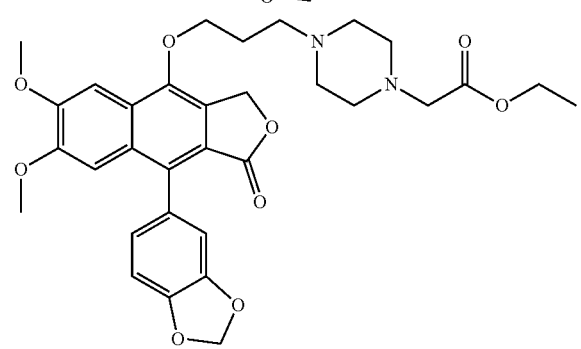
24
-continued
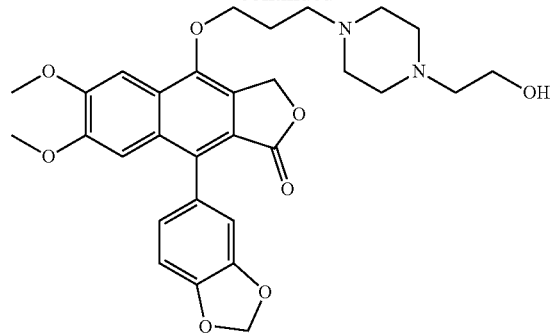
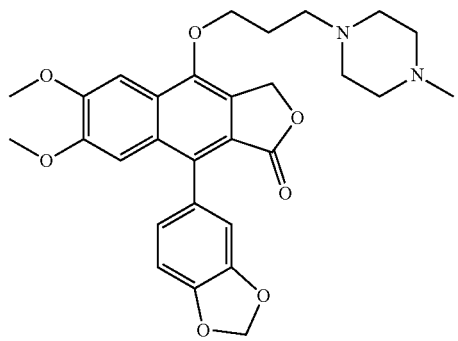
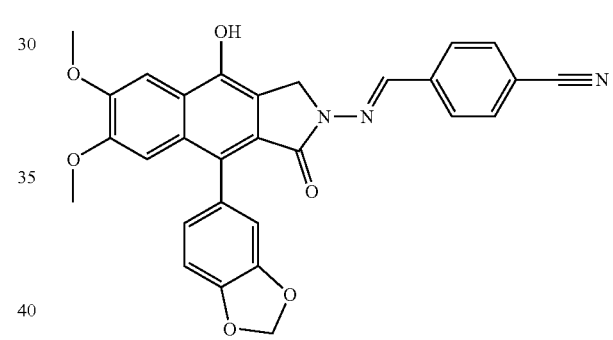
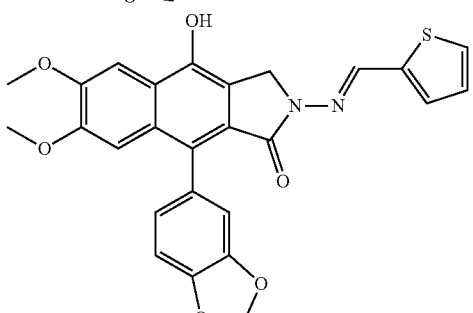
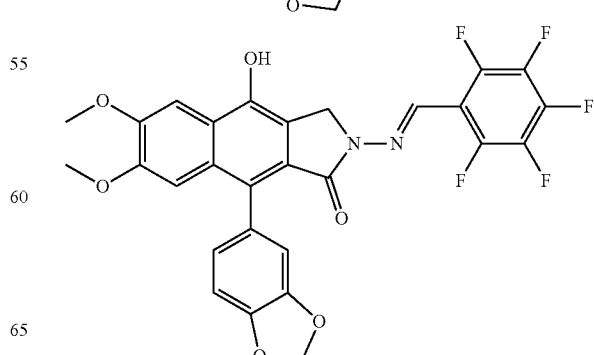

-continued

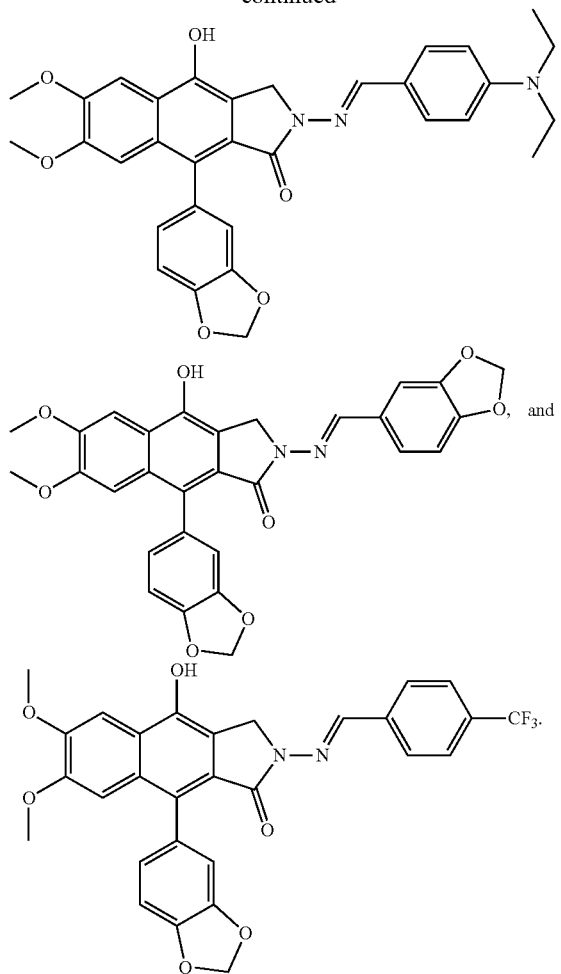

and

BRIEF DESCRIPTION OF THE FIGURES

The above and other objects, features, and advantages of the present invention will become more apparent when taken in conjunction with the following description and drawings, wherein.

DETAILED DESCRIPTION

Figure 1A:
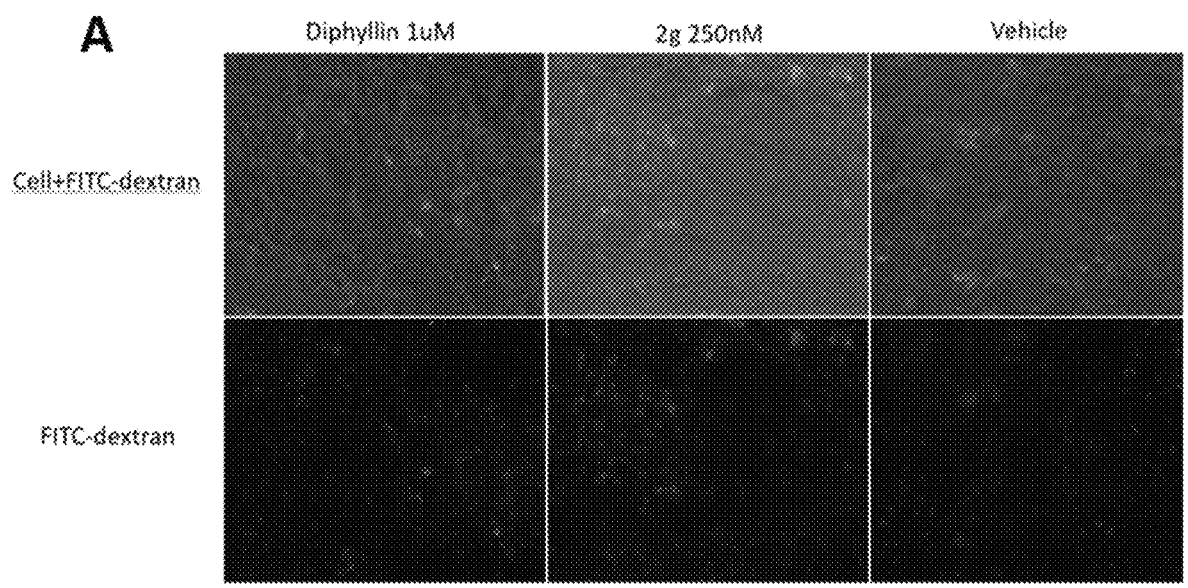
FIG. 1A shows FITC-dextran stained (0.5 mg/ml) HEK293 cells after 4 hr treatment with chosen inhibitor or vehicle, demonstrating that diphyllin derivatives cause an increase in intracellular vesicle pH but no corresponding change in cytosolic pH.

For the purposes of promoting an understanding of the principles of the present disclosure, references will now be made to the embodiments illustrated in the drawings, and specific language will be used to describe the same. It will nevertheless be understood that no limitation of the scope of this disclosure is thereby intended.

The present invention generally relates to new compounds for therapeutic uses. In particular, this disclosure relates to novel arylnaphthalene compounds as a vacuolar-ATPase inhibitor that are useful for treatment of various viral infections.

Also described herein are pharmaceutical compositions of such compounds and methods for treating a viral infection by administering therapeutically effective amounts of such compound alone or in a pharmaceutical composition.

As used herein, the following terms and phrases shall have the meanings set forth below. Unless defined otherwise, all technical and scientific terms used herein have the same meaning as commonly understood to one of ordinary skill in the art.

A "halogen" designates F, CI, Br or I. A "halogen-substitution" or "halo" substitution designates replacement of one or more hydrogen atoms with F, CI, Br or I.

As used herein, the term "alkyl" refers to a saturated monovalent chain of carbon atoms, which may be optionally branched. It is understood that in embodiments that include alkyl, illustrative variations of those embodiments include lower alkyl, such as $C_1$-$C_6$ alkyl, methyl, ethyl, propyl, 3-methylpentyl, and the like.

As used herein, the term "alkenyl" refers to an unsaturated monovalent chain of carbon atoms including at least one double bond, which may be optionally branched. It is understood that in embodiments that include alkenyl, illustrative variations of those embodiments include lower alkenyl, such as $C_2$-$C_6$, $C_2$-$C_4$ alkenyl, and the like.

As used herein, the term "alkynyl" refers to an unsaturated monovalent chain of carbon atoms including at least one triple bond, which may be optionally branched. It is understood that in embodiments that include alkynyl, illustrative variations of those embodiments include lower alkynyl, such as $C_2$-$C_6$, $C_2$-$C_4$ alkynyl, and the like.

As used herein, the term "cycloalkyl" refers to a monovalent chain of carbon atoms, a portion of which forms a ring. It is understood that in embodiments that include cycloalkyl, illustrative variations of those embodiments include lower cycloalkyl, such as $C_3$-$C_8$ cycloalkyl, cyclopropyl, cyclohexyl, 3-ethylcyclopentyl, and the like.

As used herein, the term "cycloalkenyl" refers to an unsaturated monovalent chain of carbon atoms, a portion of which forms a ring. It is understood that in embodiments that include cycloalkenyl, illustrative variations of those embodiments include lower cycloalkenyl, such as $C_3$-$C_8$, $C_3$-$C_6$ cycloalkenyl.

As used herein, the term "alkylene" refers to a saturated bivalent chain of carbon atoms, which may be optionally branched. It is understood that in embodiments that include alkylene, illustrative variations of those embodiments include lower alkylene, such as C2-C4, alkylene, methylene, ethylene, propylene, 3-methylpentylene, and the like.

It is understood that each of alkyl, cycloalkyl, alkenyl, cycloalkenyl, alkylene, and heterocycle may be optionally substituted with independently selected groups such as alkyl, haloalkyl, hydroxyalkyl, aminoalkyl, carboxylic acid and derivatives thereof, including esters, amides, and nitrites, hydroxy, alkoxy, acyloxy, amino, alky and dialkylamino, acylamino, thio, and the like, and combinations thereof.

As used herein, the term "heterocyclic" or "heterocycle" refers to a monovalent chain of carbon and heteroatoms, wherein the heteroatoms are selected from nitrogen, oxygen, and sulfur, and a portion of which, at least one heteroatom, forms a ring. The term "heterocycle" may include both "aromatic heterocycles" and "non-aromatic heterocycles." Heterocycles include 4-7 membered monocyclic and 8-12 membered bicyclic rings, such as imidazolyl, thiazolyl, oxazolyl, oxazinyl, thiazinyl, dithianyl, dioxanyl, isoxazolyl, isothiazolyl, triazolyl, furanyl, tetrahydrofuranyl, dihydrofuranyl, pyranyl, tetrazolyl, pyrazolyl, pyrazinyl, pyridazinyl, imidazolyl, pyridinyl, pyrrolyl, dihydropyrrolyl, pyrrolidinyl, piperidinyl, piperazinyl, pyrimidinyl, morpholinyl, tetrahydrothiophenyl, thiophenyl, azetidinyl, oxetanyl, thiiranyl, oxiranyl, aziridinyl, and the like. "Heterocycles" may be optionally substituted at any one or more positions capable of bearing a hydrogen atom.

As used herein, the term "aryl" includes monocyclic and polycyclic aromatic carbocyclic groups, each of which may be optionally substituted. The term "optionally substituted aryl" refers to an aromatic mono or polycyclic ring of carbon atoms, such as phenyl, naphthyl, and the like, which may be optionally substituted with one or more independently selected substituents, such as halo, hydroxyl, amino, alkyl, or alkoxy, alkylsulfony, cyano, nitro, and the like.

The term "heteroaryl" or "aromatic heterocycle" includes substituted or unsubstituted aromatic single ring structures, preferably 5-to 7-membered rings, more preferably 5-to 6-membered rings, whose ring structures include at least one heteroatom, preferably one to four heteroatoms, more preferably one or two heteroatoms. The term "heteroaryl" may also include ring systems having one or two rings wherein at least one of the rings is heteroaromatic, e.g., the other cyclic rings can be cycloalkyl, cycloalkenyl, cycloalkynyl, aromatic carbocycle, heteroaryl, and/or heterocycle. Heteroaryl groups include, without limitation, pyridyl, N-oxopyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, and the like. In some embodiments, the heteroaryl group has from 1 to about 20 carbon atoms, and in further embodiments from about 3 to about 20 carbon atoms. In some embodiments, the heteroaryl group contains 3 to about 14, 3 to about 7, or 5 to 6 ring-forming atoms. In some embodiments, the heteroaryl group has 1 to about 4, 1 to about 3, or 1 to 2 heteroatoms.

In some embodiments, "heterocycloalkyl" refers to a non-aromatic heterocycle where one or more of the ring-forming atoms are a heteroatom such as an O, N, or S atom. Heterocycloalkyl groups can include mono- or polycyclic (e.g., having 2, 3 or 4 fused rings) ring systems as well as spirocycles. Example heterocycloalkyl groups include morpholino, thiomorpholino, piperazinyl, tetrahydrofuranyl, tetrahydrothienyl, 2,3-dihydrobenzofuryl, 1,3-benzodioxole, benzo-1,4-dioxane, piperidinyl, pyrrolidinyl, isoxazolidinyl, isothiazolidinyl, pyrazolidinyl, oxazolidinyl, thiazolidinyl, imidazolidinyl, and the like. Also included in the definition of heterocycloalkyl are moieties that have one or more aromatic rings fused (i.e., having a bond in common with) to the nonaromatic heterocyclic ring, for example phthalimidyl, naphthalimidyl, and benzo derivatives of heterocycles. A heterocycloalkyl group having one or more fused aromatic rings can be attached though either the aromatic or non-aromatic portion.

The term "optionally substituted," or "optional substituents," as used herein, means that the groups in question are either unsubstituted or substituted with one or more of the substituents specified. When the groups in question are substituted with more than one substituent, the substituents may be the same or different. Furthermore, when using the terms "independently," "independently are," and "independently selected from" mean that the groups in question may be the same or different. Certain of the herein defined terms may occur more than once in the structure, and upon such occurrence each term shall be defined independently of the other.

The term "patient" includes human and non-human animals such as companion animals (dogs and cats and the like) and livestock animals. Livestock animals are animals raised for food production. The patient to be treated is preferably a mammal, in particular a human being.

The term "pharmaceutically acceptable carrier" is art-recognized and refers to a pharmaceutically-acceptable material, composition or vehicle, such as a liquid or solid filler, diluent, excipient, solvent or encapsulating material, involved in carrying or transporting any subject composition or component thereof. Each carrier must be "acceptable" in the sense of being compatible with the subject composition and its components and not injurious to the patient. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

As used herein, the term "administering" includes all means of introducing the compounds and compositions described herein to the patient, including, but are not limited to, oral (po), intravenous (iv), intramuscular (im), subcutaneous (sc), transdermal, inhalation, buccal, ocular, sublingual, vaginal, rectal, and the like. The compounds and compositions described herein may be administered in unit dosage forms and/or formulations containing conventional nontoxic pharmaceutically acceptable carriers, adjuvants, and vehicles.

Solid medicinal forms can comprise inert components and carrier substances, such as calcium carbonate, calcium phosphate, sodium phosphate, lactose, starch, mannitol, alginates, gelatine, guar gum, magnesium stearate, aluminium stearate, methyl cellulose, talc, highly dispersed silicic acids, silicone oil, higher molecular weight fatty acids, (such as stearic acid), gelatine, agar agar or vegetable or animal fats and oils, or solid high molecular weight polymers (such as polyethylene glycol); preparations which are suitable for oral administration can comprise additional flavorings and/or sweetening agents, if desired.

Liquid medicinal forms can be sterilized and/or, where appropriate, comprise auxiliary substances, such as preservatives, stabilizers, wetting agents, penetrating agents, emulsifiers, spreading agents, solubilizers, salts, sugars or sugar alcohols for regulating the osmotic pressure or for buffering, and/or viscosity regulators. Examples of such additives are tartrate and citrate buffers, ethanol and sequestering agents (such as ethylenediaminetetraacetic acid and its nontoxic salts). High molecular weight polymers, such as liquid polyethylene oxides, microcrystalline celluloses, carboxymethyl celluloses, polyvinylpyrrolidones, dextrans or gelatine, are suitable for regulating the viscosity. Examples of solid carrier substances are starch, lactose, mannitol, methyl cellulose, talc, highly dispersed silicic acids, high molecular weight fatty acids (such as stearic acid), gelatine, agar, calcium phosphate, magnesium stearate, animal and vegetable fats, and solid high molecular weight polymers, such as polyethylene glycol.

Oily suspensions for parenteral or topical applications can be vegetable, synthetic or semisynthetic oils, such as liquid fatty acid esters having in each case from 8 to 22 carbon atoms in the fatty acid chains, for example palmitic acid, lauric acid, tridecanoic acid, margaric acid, stearic acid, arachidic acid, myristic acid, behenic acid, pentadecanoic acid, linoleic acid, elaidic acid, brasidic acid, erucic acid or oleic acid, which are esterified with monohydric to trihydric alcohols having from 1 to 6 carbon atoms, such as methanol, ethanol, propanol, butanol, pentanol or their isomers, glycol or glycerol. Examples of such fatty acid esters are commercially available miglyols, isopropyl myristate, isopropyl palmitate, isopropyl stearate, PEG 6-capric acid, caprylic/capric acid esters of saturated fatty alcohols, polyoxyethylene glycerol trioleates, ethyl oleate, waxy fatty acid esters, such as artificial ducktail gland fat, coconut fatty acid isopropyl ester, oleyl oleate, decyl oleate, ethyl lactate, dibutyl phthalate, diisopropyl adipate, polyol fatty acid esters, inter alia. Silicone oils of differing viscosity, or fatty alcohols, such as isotridecyl alcohol, 2-octyldodecanol, cetylstearyl alcohol or oleyl alcohol, or fatty acids, such as oleic acid, are also suitable. It is furthermore possible to use vegetable oils, such as castor oil, almond oil, olive oil, sesame oil, cotton seed oil, groundnut oil, soybean oil or the like.

Suitable solvents, gelatinizing agents and solubilizers are water or water miscible solvents. Examples of suitable substances are alcohols, such as ethanol or isopropyl alcohol, benzyl alcohol, 2-octyldodecanol, polyethylene glycols, phthalates, adipates, propylene glycol, glycerol, di- or tripropylene glycol, waxes, methyl cello solve, cello solve, esters, morpholines, dioxane, dimethyl sulphoxide, dimethylformamide, tetrahydrofuran, cyclohexanone, etc.

Mixtures of gelatinizing agents and film-forming agents are also perfectly possible. In this case, use is made, in particular, of ionic macromolecules such as sodium carboxymethyl cellulose, polyacrylic acid, polymethacrylic acid and their salts, sodium amylopectin semiglycolate, alginic acid or propylene glycol alginate as the sodium salt, gum arabic, xanthan gum, guar gum or carrageenan. The following can be used as additional formulation aids: glycerol, paraffin of differing viscosity, triethanolamine, collagen, allantoin and novantisolic acid. Use of surfactants, emulsifiers or wetting agents, for example of sodium lauryl sulphate, fatty alcohol ether sulphates, di-sodium-N-lauryl-iminodipropionate, polyethoxylated castor oil or sorbitan monooleate, sorbitan monostearate, polysorbates (e.g. Tween), cetyl alcohol, lecithin, glycerol monostearate, polyoxyethylene stearate, alkylphenol polyglycol ethers, cetyltrimethylammonium chloride or mono-/dialkylpolyglycol ether orthophosphoric acid monoethanolamine salts can also be required for the formulation. Stabilizers, such as montmorillonites or colloidal silicic acids, for stabilizing emulsions or preventing the breakdown of active substances such as antioxidants, for example tocopherols or butylhydroxyanisole, or preservatives, such as p-hydroxybenzoic acid esters, can likewise be used for preparing the desired formulations.

Preparations for parenteral administration can be present in separate dose unit forms, such as ampoules or vials. Use is preferably made of solutions of the active compound, preferably aqueous solution and, in particular, isotonic solutions and also suspensions. These injection forms can be made available as ready-to-use preparations or only be prepared directly before use, by mixing the active compound, for example the lyophilisate, where appropriate containing other solid carrier substances, with the desired solvent or suspending agent.

Intranasal preparations can be present as aqueous or oily solutions or as aqueous or oily suspensions. They can also be present as lyophilisates which are prepared before use using the suitable solvent or suspending agent.

Inhalable preparations can present as powders, solutions or suspensions. Preferably, inhalable preparations are in the form of powders, e.g. as a mixture of the active ingredient with a suitable formulation aid such as lactose.

The preparations are produced, aliquoted and sealed under the customary antimicrobial and aseptic conditions.

As indicated above, a compound of the invention may be administered as a combination therapy with further active agents, e.g. therapeutically active compounds useful in the treatment of cancer, for example, prostate cancer, ovarian cancer, lung cancer, or breast cancer. For a combination therapy, the active ingredients may be formulated as compositions containing several active ingredients in a single dose form and/or as kits containing individual active ingredients in separate dose forms. The active ingredients used in combination therapy may be co-administered or administered separate It is to be understood that the total daily usage of the compounds and compositions described herein may be decided by the attending physician within the scope of sound medical judgment. The specific therapeutically effective dose level for any particular patient will depend upon a variety of factors, including the disorder being treated and the severity of the disorder; activity of the specific compound employed; the specific composition employed; the age, body weight, general health, gender, and diet of the patient: the time of administration, and rate of excretion of the specific compound employed, the duration of the treatment, the drugs used in combination or coincidentally with the specific compound employed; and like factors well known to the researcher, veterinarian, medical doctor or other clinician of ordinary skill.

Depending upon the route of administration, a wide range of permissible dosages are contemplated herein, including doses falling in the range from about 1 µg/kg to about 1 g/kg. The dosage may be single or divided, and may be administered according to a wide variety of dosing protocols, including q.d$_6$, b.i.d$_6$, t.i.d, or even every other day, once a week, once a month, and the like. In each case the therapeutically effective amount described herein corresponds to the instance of administration, or alternatively to the total daily, weekly, or monthly dose.

As used herein, the term "therapeutically effective amount" refers to that amount of active compound or pharmaceutical agent that elicits the biological or medicinal response in a tissue system, animal or human that is being sought by a researcher, veterinarian, medical doctor or other clinicians, which includes alleviation of the symptoms of the disease or disorder being treated. In one aspect, the therapeutically effective amount is that which may treat or alleviate the disease or symptoms of the disease at a reasonable benefit/risk ratio applicable to any medical treatment.

As used herein, the term "therapeutically effective amount" refers to the amount to be administered to a patient, and may be based on body surface area, patient weight, and/or patient condition. In addition, it is appreciated that there is an interrelationship of dosages determined for humans and those dosages determined for animals, including test animals (illustratively based on milligrams per meter squared of body surface) as described by Freireich, E. J., et al., Cancer Chemother. Rep. 1966, 50 (4), 219, the disclosure of which is incorporated herein by reference. Body surface area may be approximately determined from patient height and weight (see, e.g., Scientific Tables, Geigy Pharmaceuticals, Ardley, New York, pages 537-538 (1970)). A therapeutically effective amount of the compounds described herein may be defined as any amount useful for inhibiting the growth of (or killing) a population of malignant cells or cancer cells, such as may be found in a patient in need of relief from such cancer or malignancy. Typically, such effective amounts range from about 5 mg/kg to about 500 mg/kg, from about 5 mg/kg to about 250 mg/kg, and/or from about 5 mg/kg to about 150 mg/kg of compound per patient body weight. It is appreciated that effective doses may also vary depending on the route of administration, optional excipient usage, and the possibility of co-usage of the compound with other conventional and non-conventional therapeutic treatments, including other anti-tumor agents, radiation therapy, and the like.

In the present disclosure the term "about" can allow for a degree of variability in a value or range, for example, within 10%, within 5%, or within 1% of a stated value or of a stated limit of a range. In the present disclosure the term "substantially" can allow for a degree of variability in a value or range, for example, within 90%, within 95%, or within 99% of a stated value or of a stated limit of a range.

In some illustrative embodiments, the present invention relates to a compound having the formula (I)

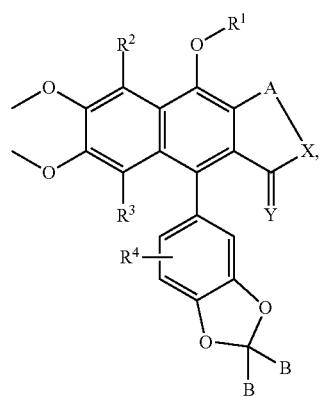

(I)

or a pharmaceutically acceptable salt thereof, wherein

A is C=O, $CR_2$, $CH_2$, CHR, O, S, NH, NR, wherein R is an alkyl;
B is hydrogen (H), deuterium (D), or fluorine (F);
X is C=O, $CR_2$, $CH_2$, CHR, O, S, NH, NR, wherein R is an alkyl;
Y is O, $CF_2$, $CH_2$, CHR, S, NH, NR, wherein R is an alkyl;
$R^1$ is hydrogen, an alkyl, alkylamide, alkenyl, alkenylamide, alkenylamino, alkynyl, alkynylamide, alkynylamino, heteroalkyl, heteroalkenyl, heteroalkynyl, heterocycll, cycloalkyl, cycloalkenyl, cycloheteroalkyl, cycloheteroalkenyl, acyl, aryl, heteroaryl, arylalkyl, arylalkenyl, or arylalkynyl; and
$R^2$, $R^3$, and $R^4$ are each independently selected from the group consisting of hydrogen, deuterium, —CN, —$CF_3$, and a halo.

In some illustrative embodiments, the present invention relates to a compound having the formula (I), wherein $R^1$ is

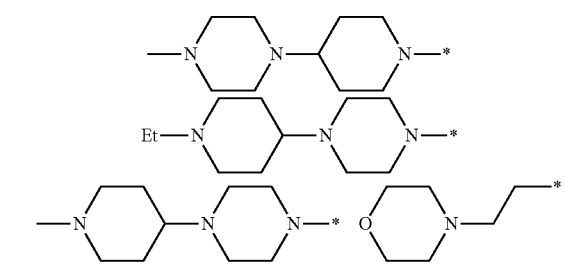

—$CH_2CH_2O(CH_2)nR^7$, —$CH_2CH_2CH_2O(CH_2)nR^7$, —$CH_2CH_2CH_2CH_2O(CH_2)nR^7$, —$CH_2(CH_2)nR^7$, or, wherein n=1~4 and
$R^7$ is 33
-continued
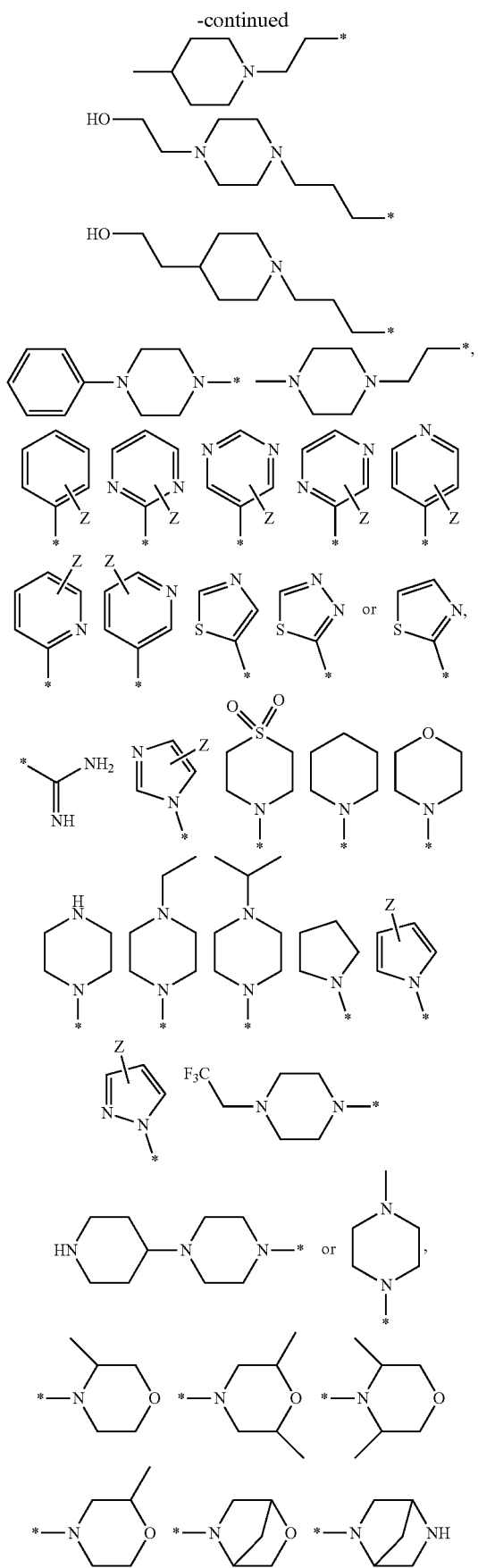
34
-continued
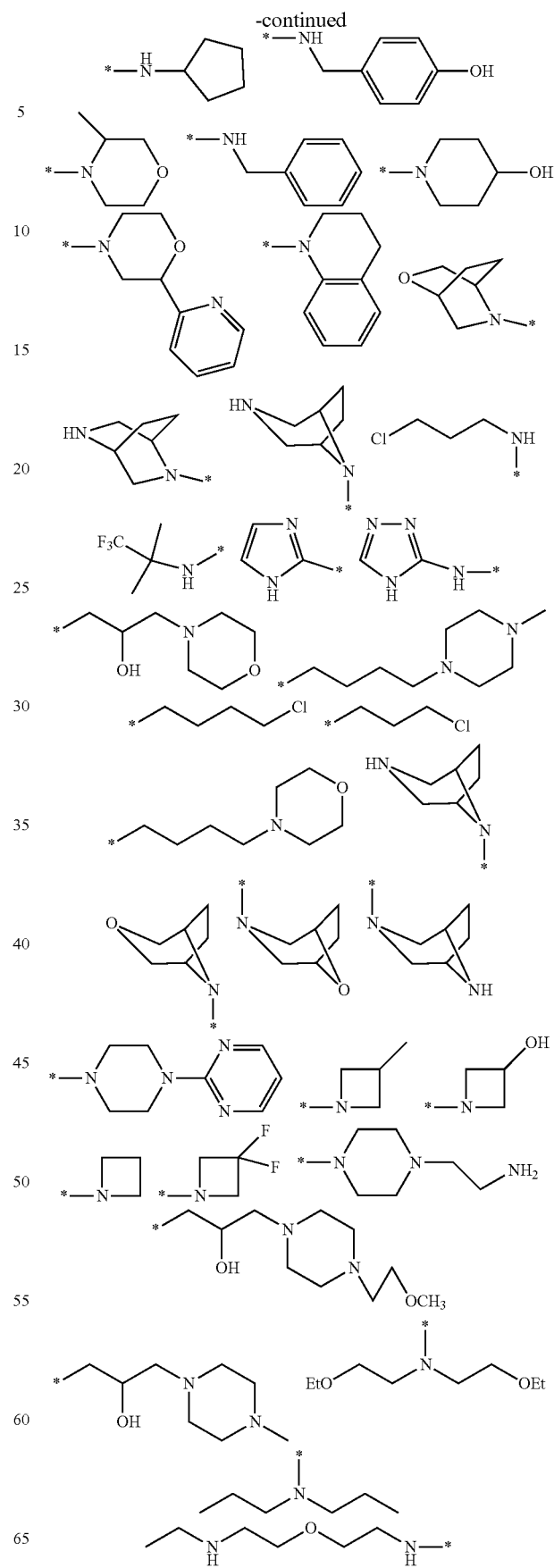

-continued

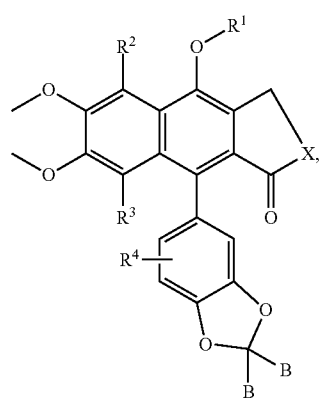

wherein Z is a halogen, C1~C3 alkyl, —CF$_3$, —CN, or —CONR$_2$, wherein R is hydrogen or a C1~C3 alkyl, and * represents site of attachment.

In some illustrative embodiments, the present invention relates to a compound having the formula (II):

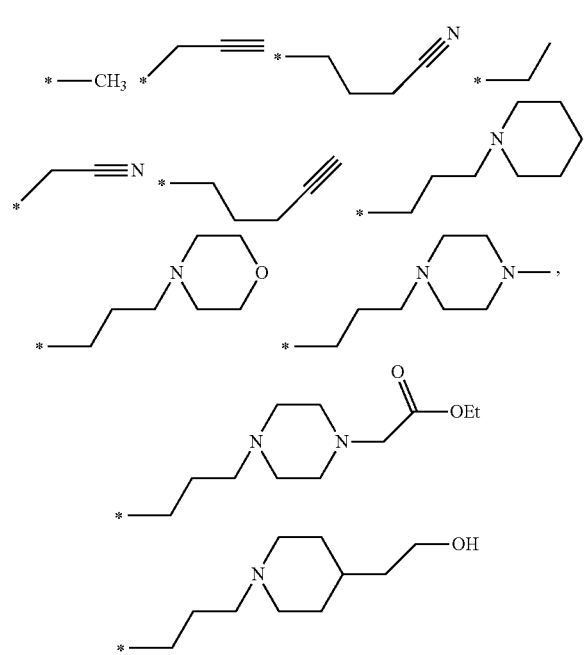

or a pharmaceutically acceptable salt thereof, wherein
B is hydrogen (H), deuterium (D), or fluorine (F);
X is CR$_2$, CH$_2$, CHR, O, S, NH, NR, wherein R is an alkyl;
R$^2$, R$^3$, and R$^4$ are each independently selected from the group consisting of hydrogen, deuterium, —CN, —CF$_3$, and a halo; and
R$^1$ is

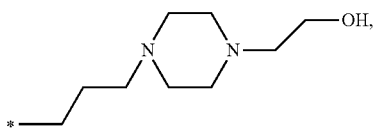

—CH$_2$CH$_2$O(CH$_2$)nR$^7$, —CH$_2$CH$_2$CH$_2$O(CH$_2$)nR$^7$, —CH$_2$CH$_2$CH$_2$CH$_2$O(CH$_2$)nR$^7$, —CH$_2$(CH$_2$)nR$^7$, or, wherein n=1~4 and R$^7$ is

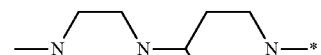

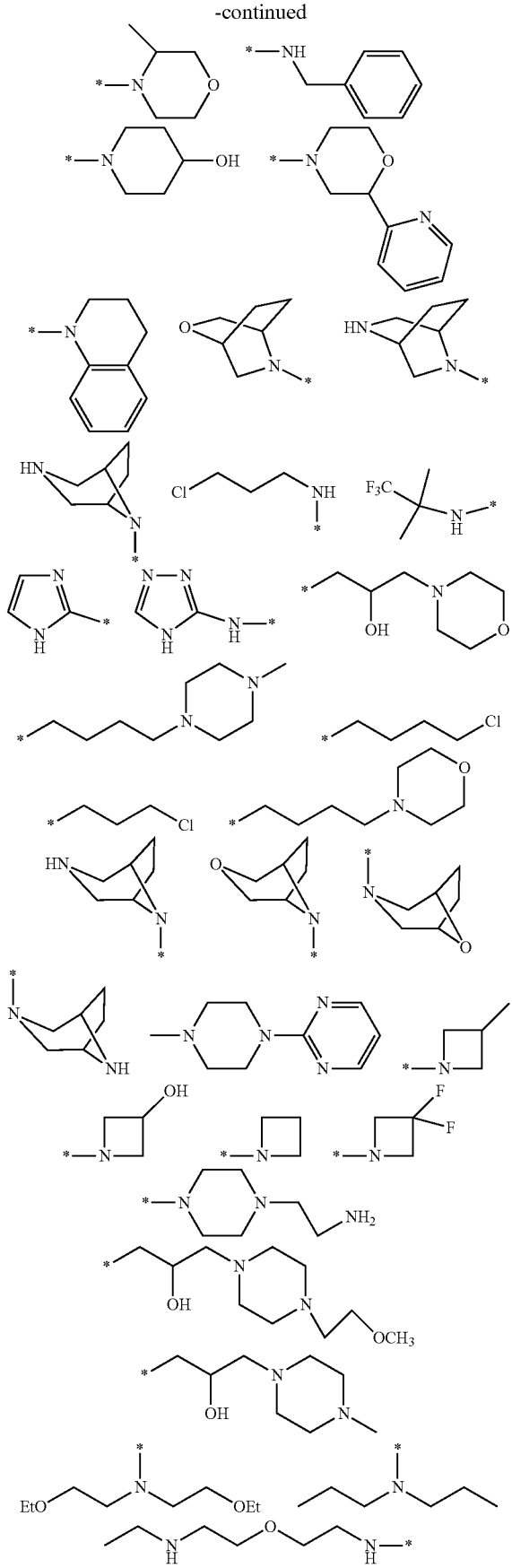
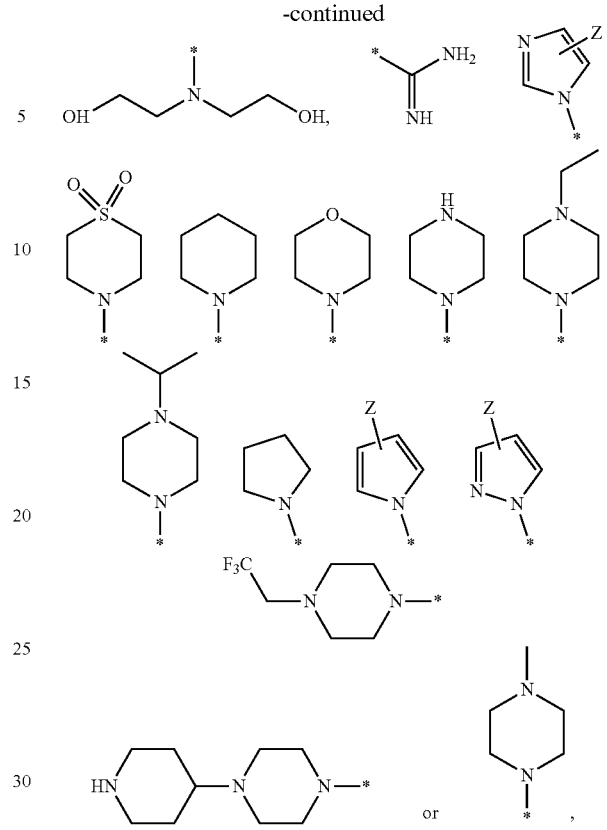
wherein Z is a halogen, C1~C3 alkyl, —CF₃, —CN, or —CONR₂, wherein R is hydrogen or a C1~C3 alkyl, and * represents site of attachment.
In some illustrative embodiments, the present invention relates to a compound having the formula (III),
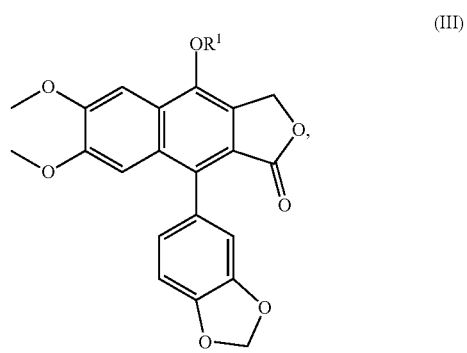
(III)
wherein R¹ is selected from the group consisting of
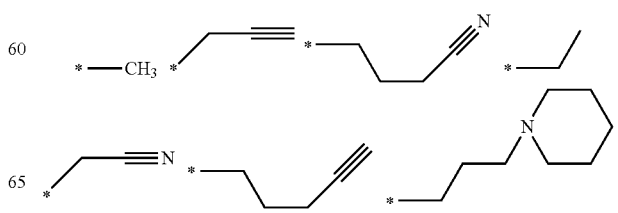

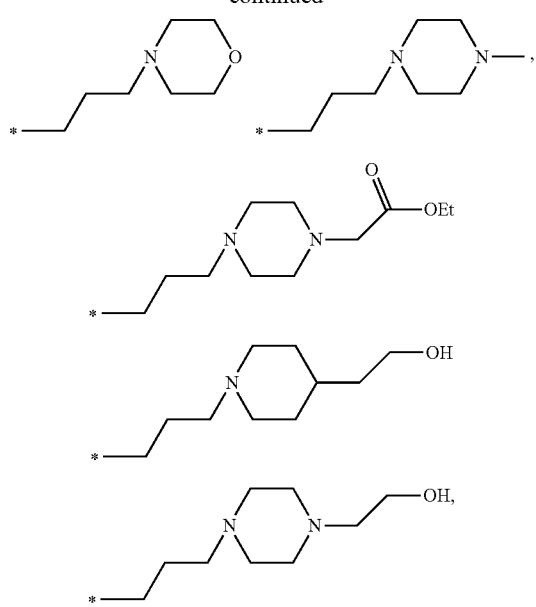
—CH$_2$CH$_2$O(CH$_2$)nR$^7$, —CH$_2$CH$_2$CH$_2$O(CH$_2$)nR$^7$, —CH$_2$CH$_2$CH$_2$CH$_2$O(CH$_2$)nR$^7$, —CH$_2$(CH$_2$)nR$^7$, or, wherein n=1~4 and
R$^7$ is
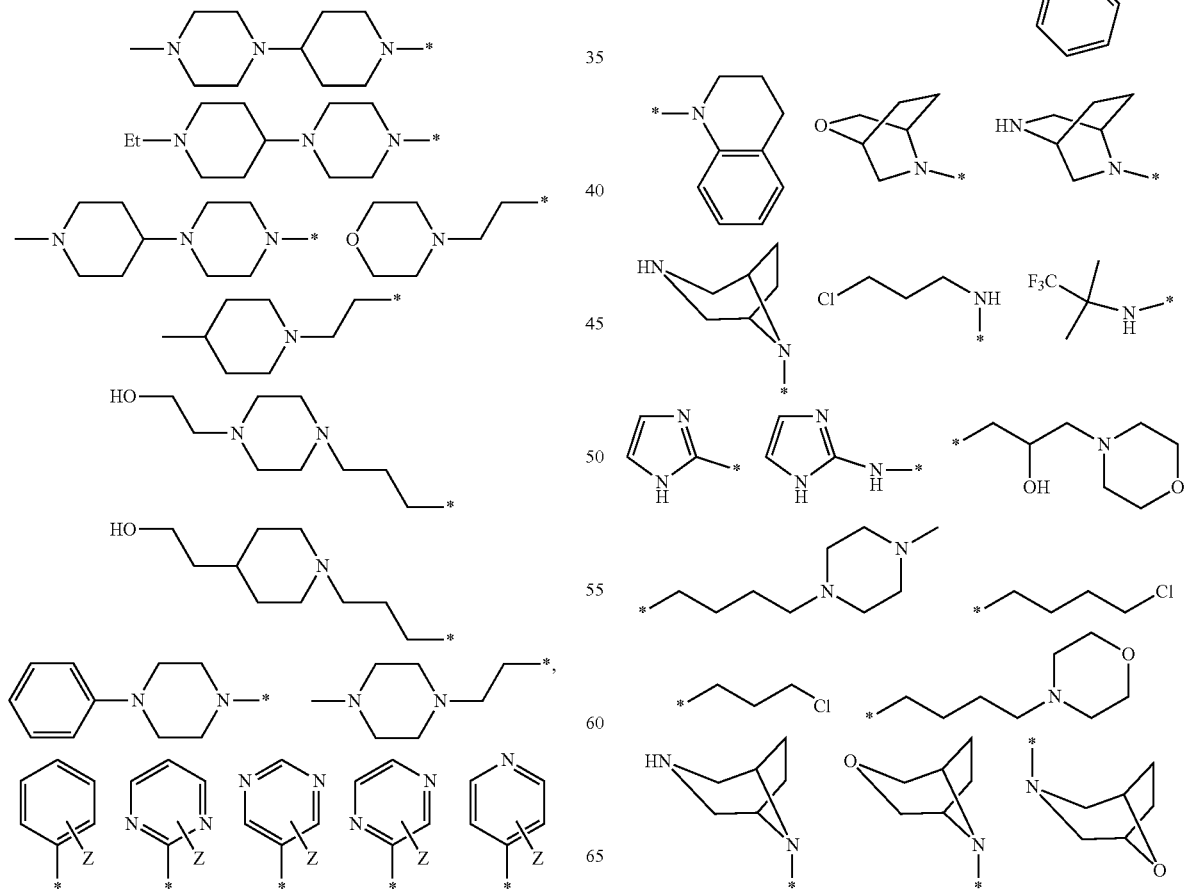

-continued
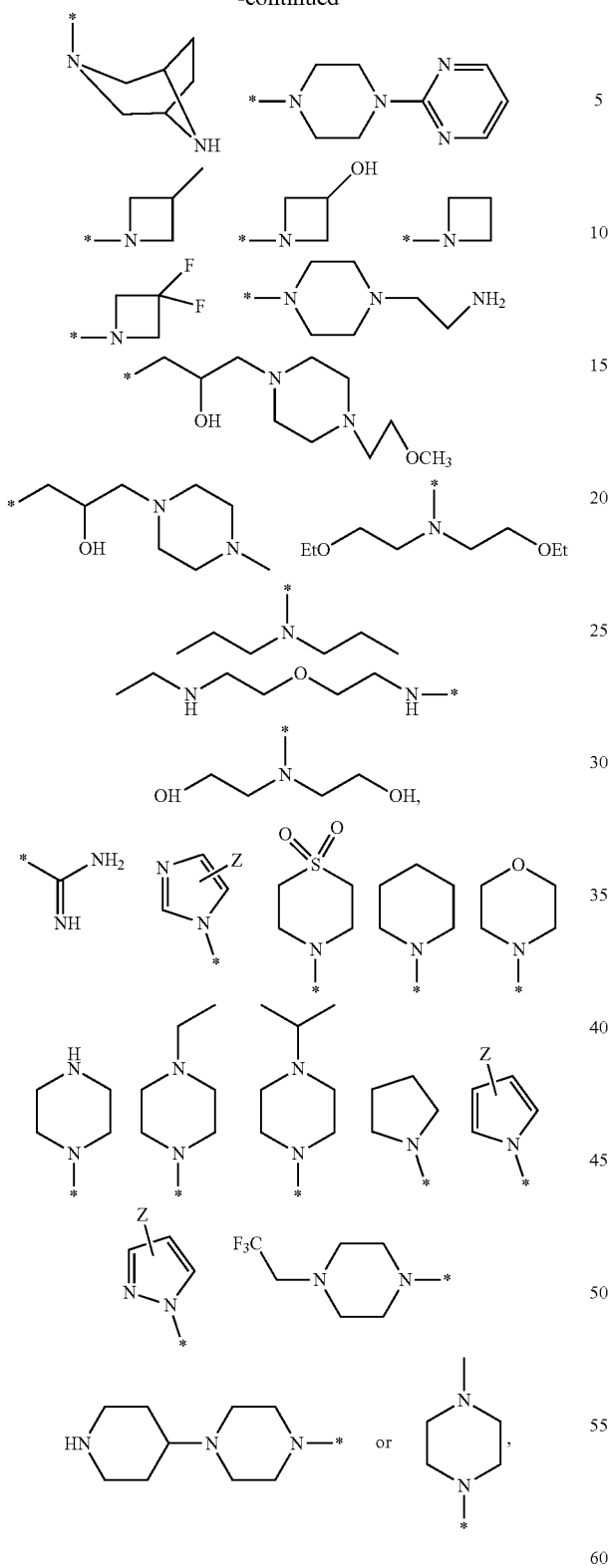
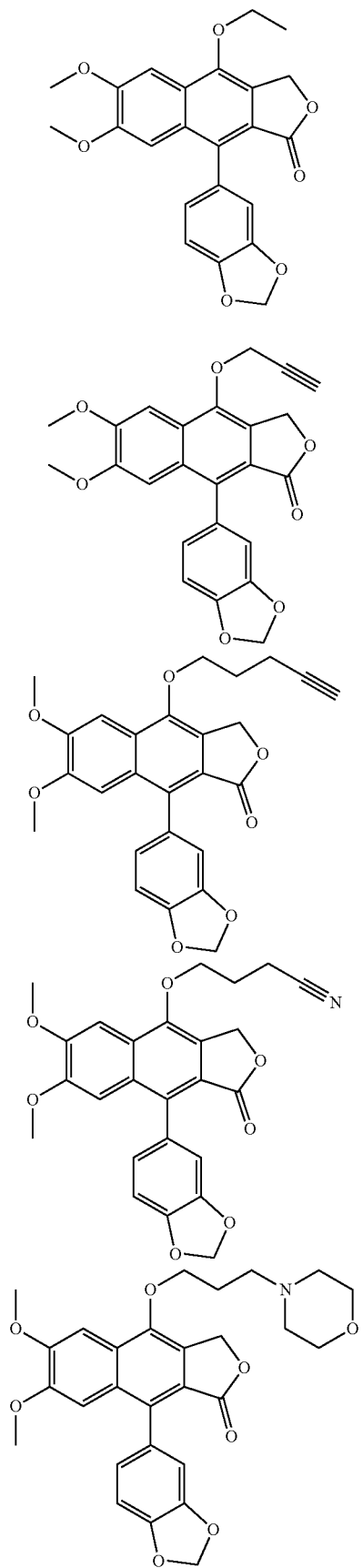
wherein Z is a halogen, C1~C3 alkyl, —CF₃, —CN, or —CONR₂, wherein R is hydrogen or a C1~C3 alkyl, and * represents site of attachment.
In some illustrative embodiments, the present invention relates to a compound having the formula (I), wherein said compound has the following structure:

-continued

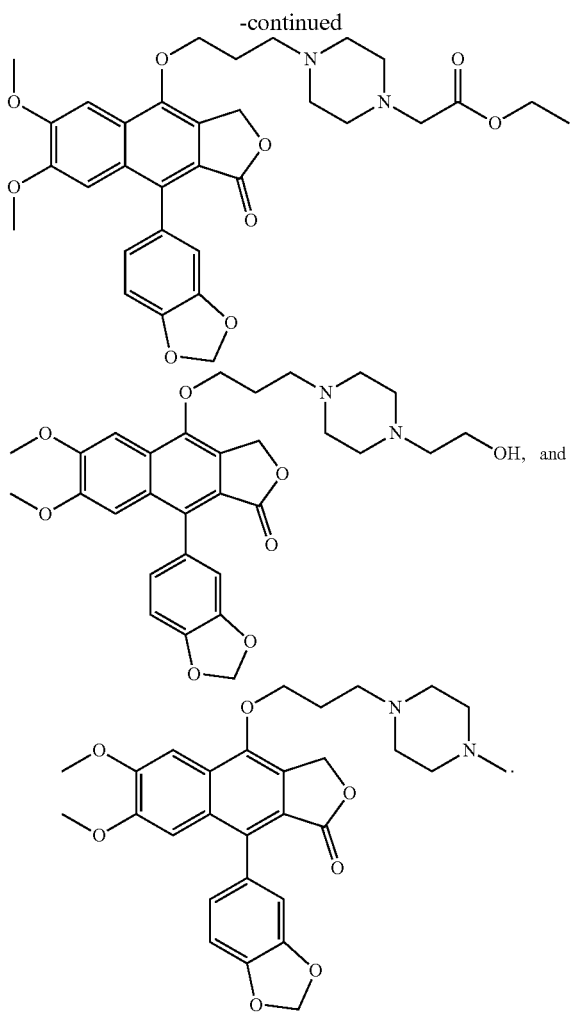

In some illustrative embodiments, the present invention relates to a pharmaceutical composition comprising one or more compounds having the formulae (I), (II), or (III) as disclosed herein, or a pharmaceutically acceptable salt thereof, together with one or more diluents, excipients or carriers.

In some illustrative embodiments, the present invention relates to a compound having the formulae (I), (II), or (III) as disclosed herein, or a pharmaceutically acceptable salt thereof, wherein the compound is an antiviral agent.

In some illustrative embodiments, the present invention relates to a compound having the formulae (I), (II), or (III) as disclosed herein, or a pharmaceutically acceptable salt thereof, wherein the compound is an antiviral agent for the treatment of a viral infection by flaviviridae viruses, including Dengue virus, West Nile virus, Yellow fever virus, Japanese encephalitis virus, Powassan virus, Zika virus, and Usutu virus; respiratory viruses, including MERS coronavirus, Influenza A H1N1 virus, Respiratory syncytial virus; Arenaviridae virus, including Tacaribe virus, Pichinde virus, Junin virus, Lassa fever virus, Lymphocytic Choriomeningitis virus; Filoviridae virus, including Ebolavirus, Marburgvirus; Togaviridae virus, including Venezuelan equine encephalitis virus, Eastern equine encephalitis virus, Western equine encephalitis virus, and Chikungunya virus; Mayarovirus; and Hantavirus.

In some illustrative embodiments, the present invention relates to a method for treating a patient with a viral infection, comprising the step of administering a therapeutically effective amount of one or more compounds having the formulae (I), (II), or (III) as disclosed herein, or a pharmaceutically acceptable salt thereof, and one or more carriers, diluents, or excipients, to a patient in need of relief from said infection.

In some illustrative embodiments, the present invention relates to a method for treating a patient with an infection, comprising the step of administering a therapeutically effective amount of one or more compounds, together with one or more carriers, diluents, or excipients, to a patient in need of relief from said infection, the compound having formula (I):

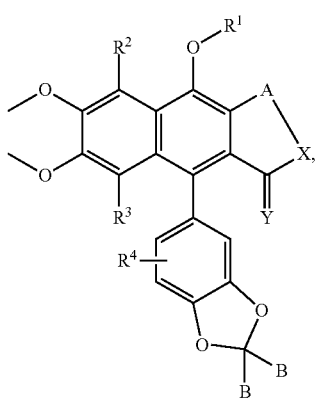

or a pharmaceutically acceptable salt thereof, wherein
A is C=O, $CR_2$, $CH_2$, CHR, O, S, NH, NR, wherein R is an alkyl;
B is hydrogen (H), deuterium (D), or fluorine (F);
X is C=O, $CR_2$, $CH_2$, CHR, O, S, NH, NR, wherein R is an alkyl;
Y is O, $CF_2$, $CH_2$, CHR, S, NH, NR, wherein R is an alkyl;
$R^1$ is hydrogen, an alkyl, alkylamide, alkenyl, alkenylamide, alkenylamino, alkynyl, alkynylamide, alkynylamino, heteroalkyl, heteroalkenyl, heteroalkynyl, heterocyclyl, cycloalkyl, cycloalkenyl, cycloheteroalkyl, cycloheteroalkenyl, acyl, aryl, heteroaryl, arylalkyl, arylalkenyl, or arylalkynyl; and
$R^2$, $R^3$, and $R^4$ are each independently selected from the group consisting of hydrogen, deuterium, —CN, —$CF_3$, and a halo.

In some illustrative embodiments, the present invention relates to a method for treating a patient with an infection, comprising the step of administering a therapeutically effective amount of one or more compounds, together with one or more carriers, diluents, or excipients, to a patient in need of relief from said infection, wherein said compound has a formula (II)
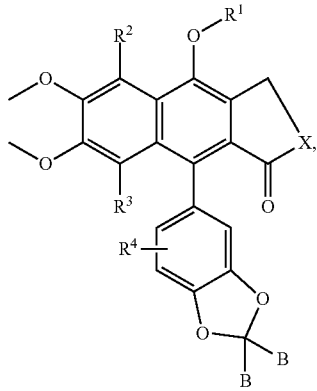
or a pharmaceutically acceptable salt thereof, wherein
  B is hydrogen (H), deuterium (D), or fluorine (F);
  X is $CR_2$, $CH_2$, CHR, O, S, NH, NR, wherein R is an alkyl;
  $R^2$, $R^3$, and $R^4$ are each independently selected from the group consisting of hydrogen, deuterium, —CN, —$CF_3$, and a halo; and
  $R^1$ is
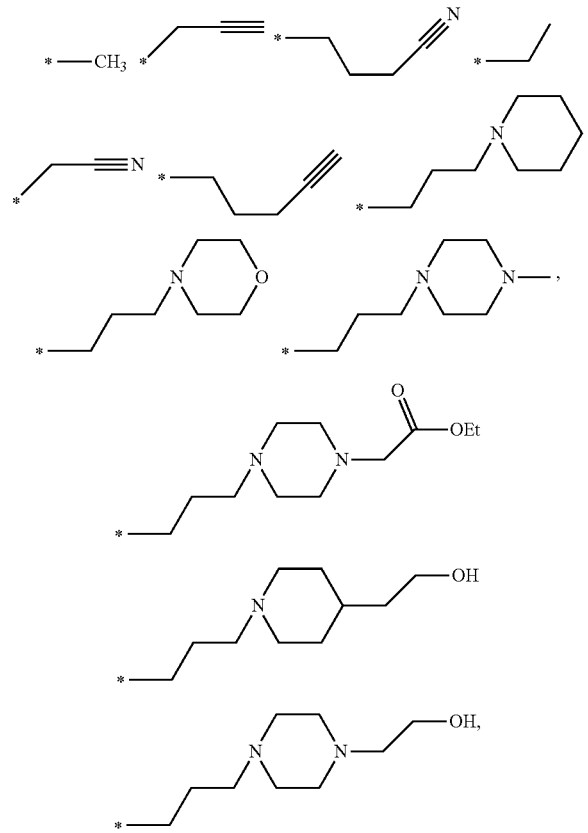
—$CH_2CH_2O(CH_2)nR^7$, —$CH_2CH_2CH_2O(CH_2)nR^7$, —$CH_2CH_2CH_2CH_2O(CH_2)nR^7$, —$CH_2(CH_2)nR^7$, or, wherein n=1~4 and
$R^7$ is
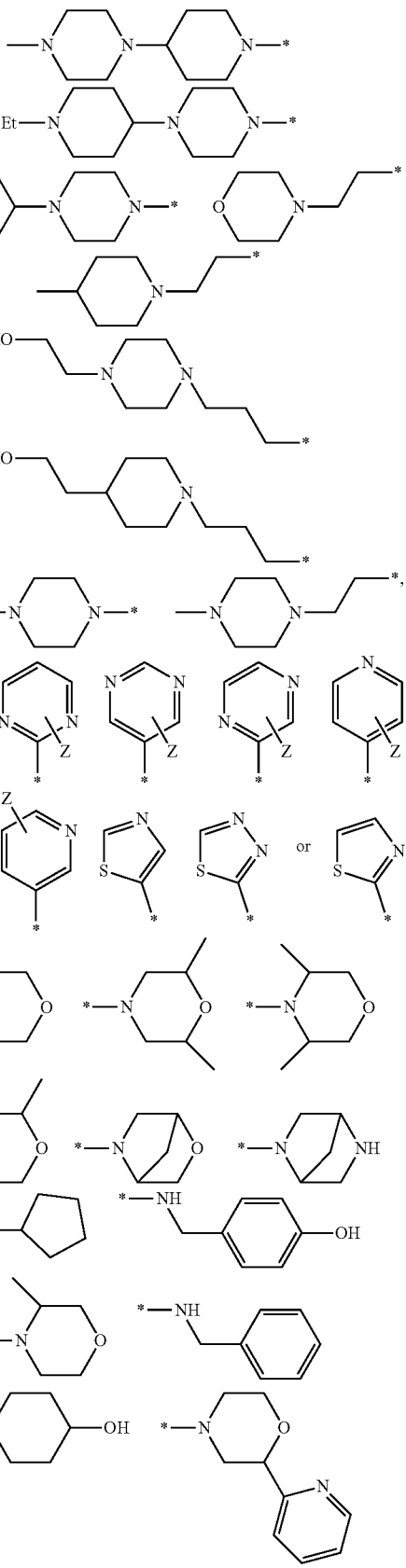

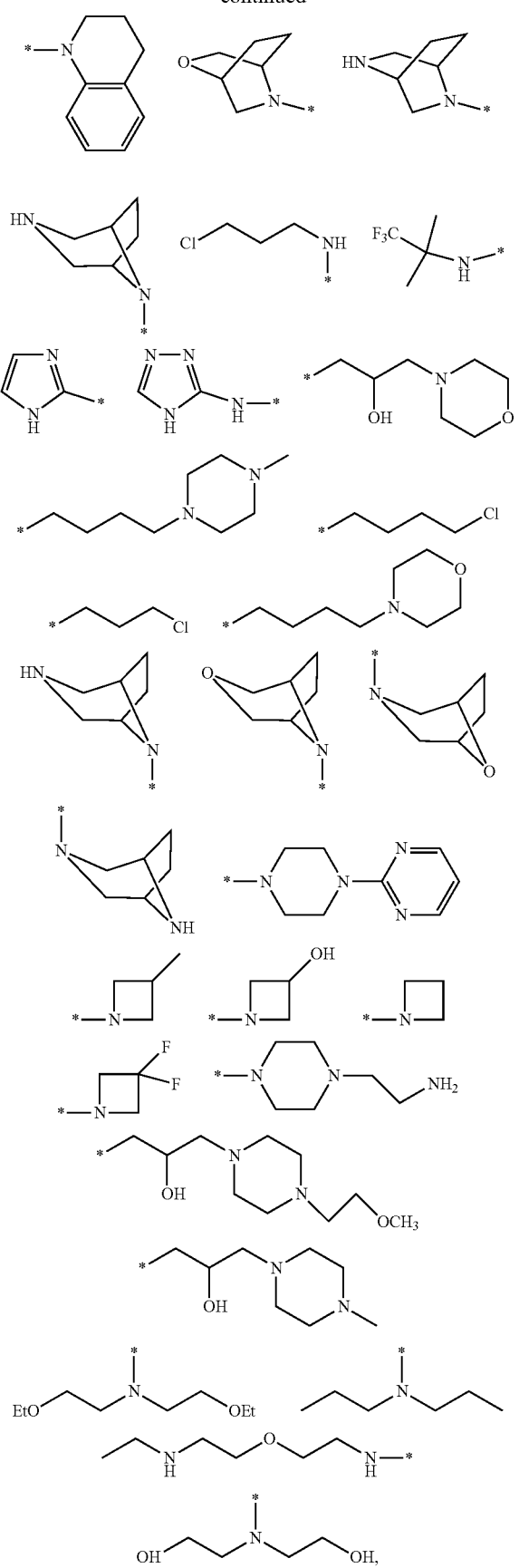
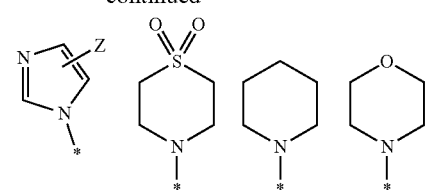
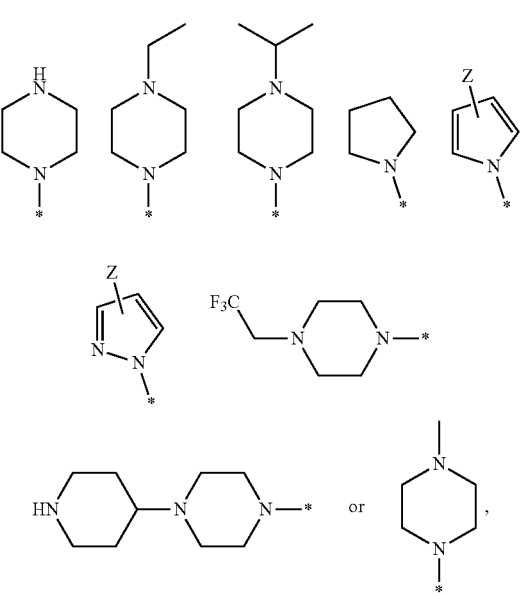
wherein Z is a halogen, C1~C3 alkyl, —CF₃, —CN, or —CONR₂, wherein R is hydrogen or a C1~C3 alkyl, and * represents site of attachment.
In some illustrative embodiments, the present invention relates to a compound having the formula
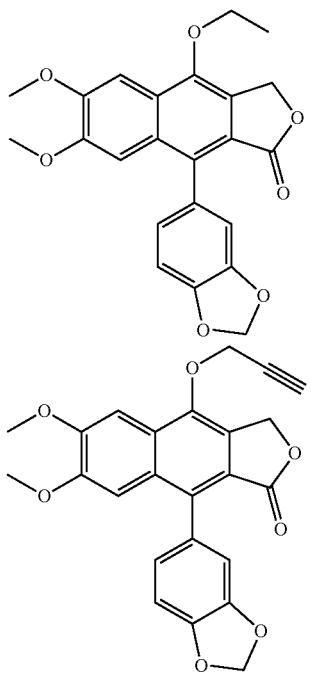

49
-continued
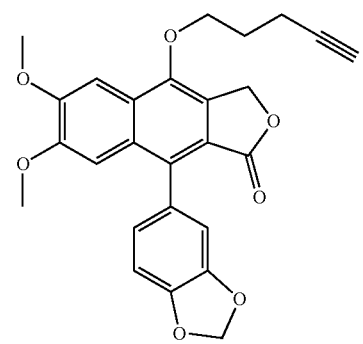
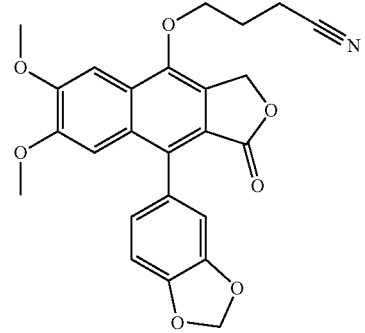
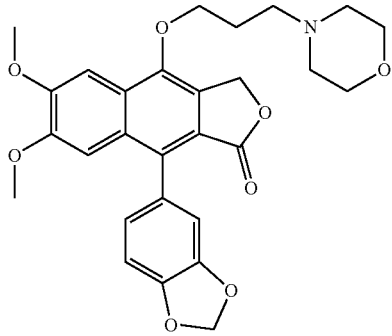
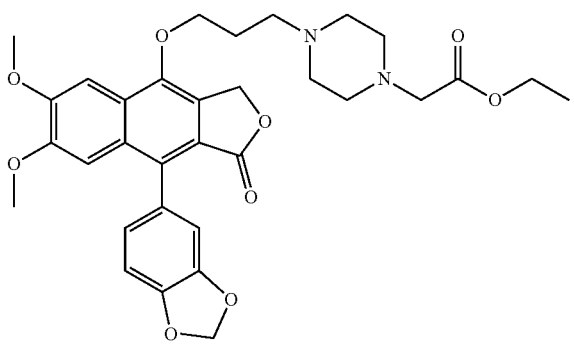
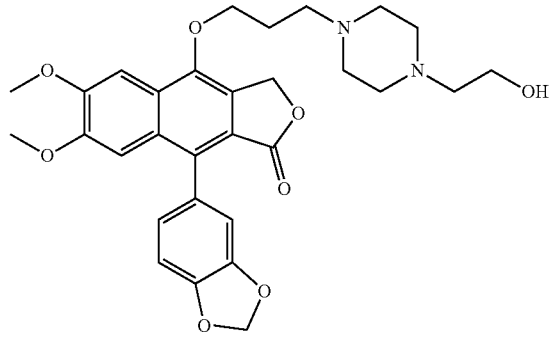
50
-continued
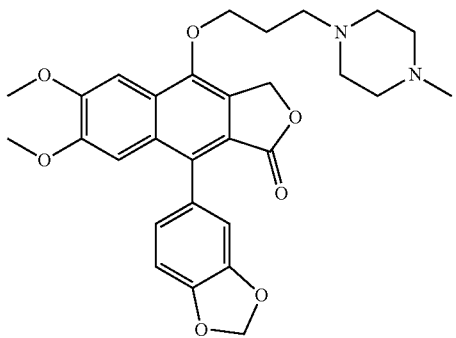
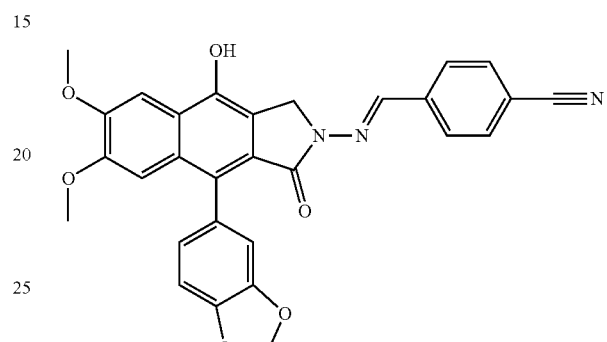
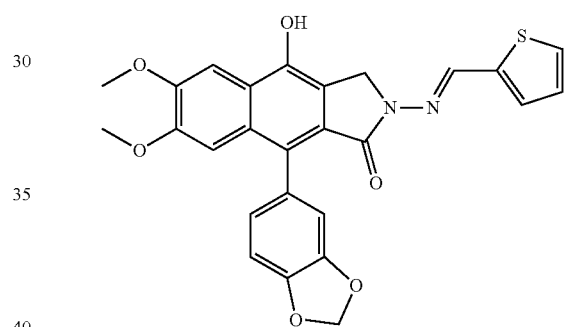
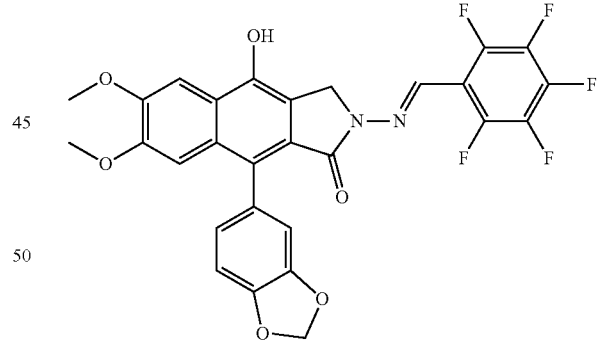
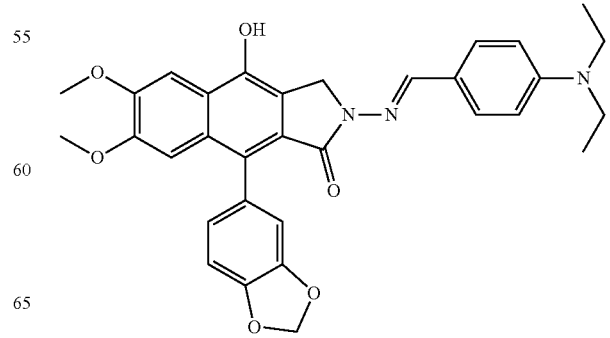

-continued

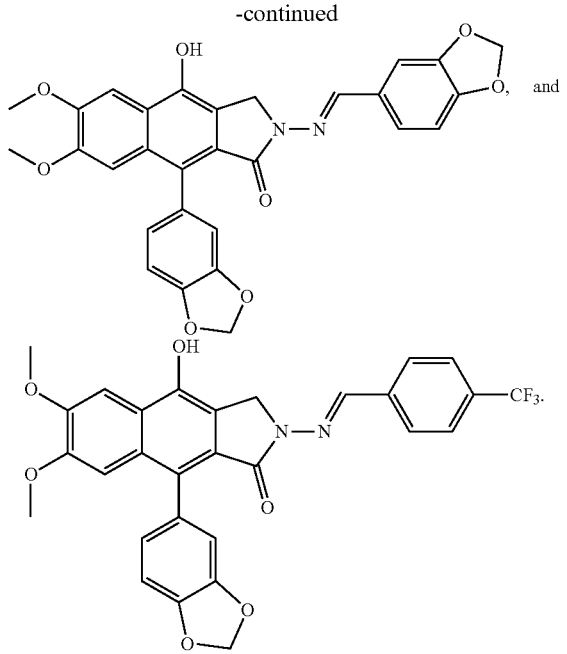
and

In some other illustrative embodiments, the present invention relates to a pharmaceutical composition comprising one or more compounds disclosed herein, or a pharmaceutically acceptable salt thereof, together with one or more diluents, excipients or carriers.

In some illustrative embodiments, the present invention relates to compounds disclosed herein, wherein the compounds are an antiviral agent.

In some other illustrative embodiments, the present invention relates to one or more compounds disclosed herein, wherein the compounds are an antiviral agent for the treatment of a viral infection by flaviviridae viruses, including Dengue virus, West Nile virus, Yellow fever virus, Japanese encephalitis virus, Powassan virus, Zika virus, and Usutu virus; respiratory viruses, including MERS coronavirus, Influenza A H1N1 virus, Respiratory syncytial virus; Arenaviridae virus, including Tacaribe virus, Pichinde virus, Junin virus, Lassa fever virus, Lymphocytic Choriomeningitis virus; Filoviridae virus, including Ebolavirus, Marburgvirus; Togaviridae virus, including Venezuelan equine encephalitis virus, Eastern equine encephalitis virus, Western equine encephalitis virus, and Chikungunya virus; Mayarovirus; and Hantavirus.

In some other illustrative embodiments, the present invention relates to a method for treating a patient with a viral infection, wherein said method comprises the step of administering a therapeutically effective amount of one or more compounds disclosed herein, and one or more carriers, diluents, or excipients, to a patient in need of relief from said infection.

In some other illustrative embodiments, the present invention relates to a method for treating a patient with a viral infection, wherein said method comprises the step of administering a therapeutically effective amount of a compound disclosed herein in combination with one or more other compounds of the same or different mode of action, and one or more carriers, diluents, or excipients, to a patient in need of relief from said viral infection.

In some illustrative embodiments, the present invention relates to a drug conjugate, wherein the drug conjugate comprises one or more compounds disclosed herein, wherein the conjugate confers cell-type or tissue type targeting or the conjugate targets another pathway that synergizes the action of compounds disclosed herein.

In some other illustrative embodiments, the present invention relates to a pharmaceutical composition comprising nanoparticles of one or more compounds disclosed herein, together with one or more diluents, excipients or carriers.

In some other illustrative embodiments, the present invention relates to a method for treating a patient with an infection comprising the step of administering a therapeutically effective amount of one or more compounds according formula (III), together with one or more carriers, diluents, or excipients, to a patient in need of relief from said infection, wherein said infection is a viral infection.

In some other illustrative embodiments, the present invention relates to a method for treating a patient with an infection comprising the step of administering a therapeutically effective amount of one or more compounds according formula (III), together with one or more carriers, diluents, or excipients, to a patient in need of relief from said infection, wherein said viral infection is an infection by flaviviridae viruses, including Dengue virus, West Nile virus, Yellow fever virus, Japanese encephalitis virus, Powassan virus, Zika virus, and Usutu virus; respiratory viruses, including MERS coronavirus, Influenza A H1N1 virus, Respiratory syncytial virus; Arenaviridae virus, including Tacaribe virus, Pichinde virus, Junin virus, Lassa fever virus, Lymphocytic Choriomeningitis virus; Filoviridae virus, including Ebolavirus, Marburgvirus; Togaviridae virus, including Venezuelan equine encephalitis virus, Eastern equine encephalitis virus, Western equine encephalitis virus, and Chikungunya virus; Mayarovirus; and Hantavirus.

In some other illustrative embodiments, the present invention relates to a method for treating a patient with an infection comprising the step of administering a therapeutically effective amount of one or more compounds together with one or more carriers, diluents, or excipients, to a patient in need of relief from said infection, wherein said compound is

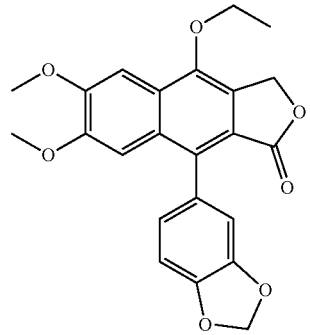

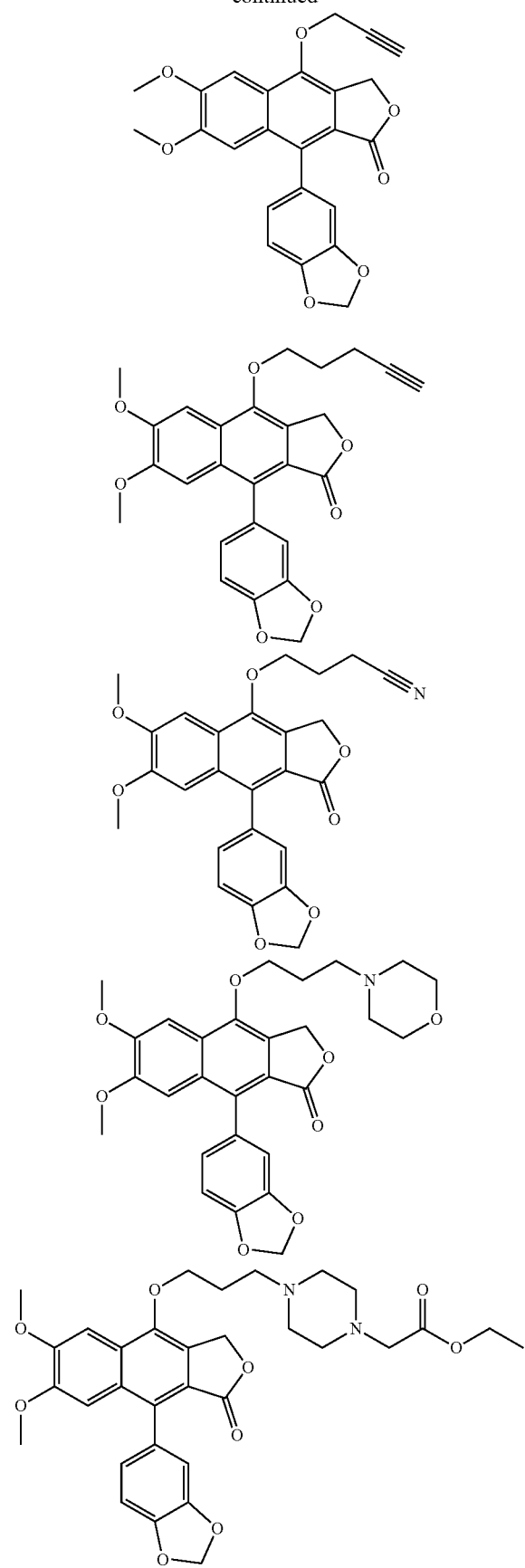

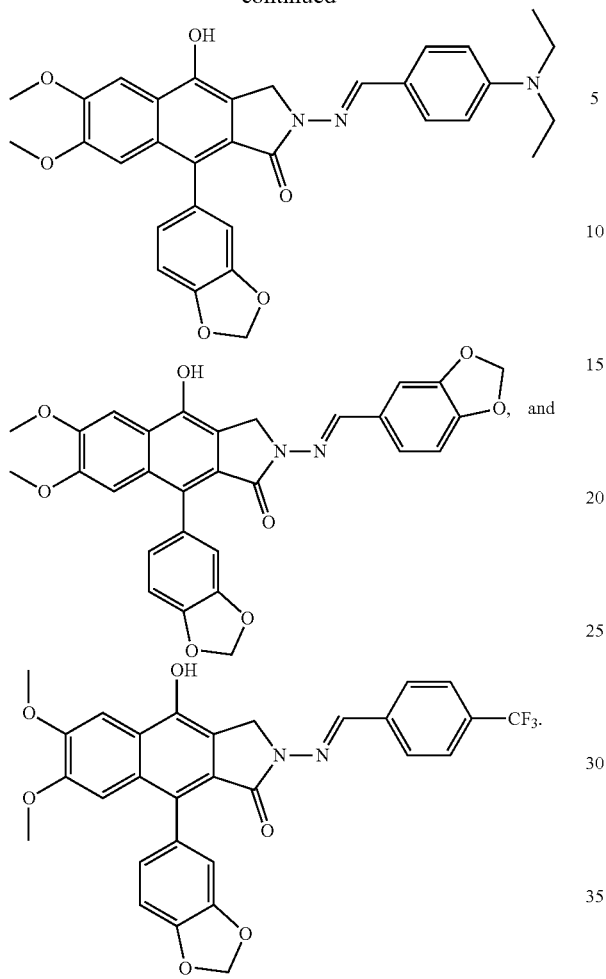

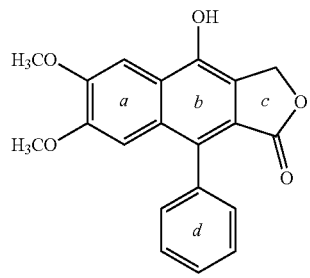

1

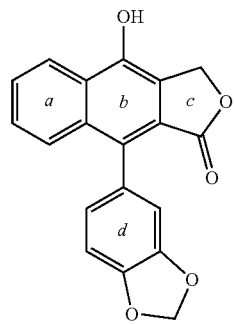

2

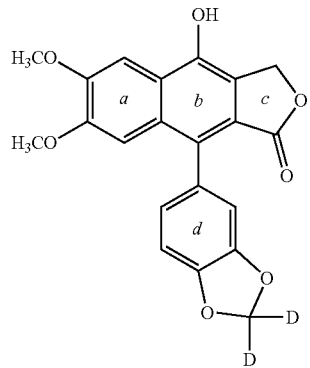

3

Fix the D-Ring

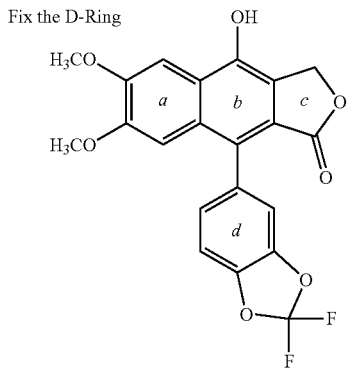

4

In some other illustrative embodiments, the present invention relates to a method for treating a patient with an infection, comprising the step of administering a therapeutically effective amount of one or more compounds as disclosed herein, together with one or more carriers, diluents, or excipients, to a patient in need of relief from said infection, wherein said infection is a viral infection.

In some other illustrative embodiments, the present invention relates to a method for treating a patient with an infection, comprising the step of administering a therapeutically effective amount of one or more compounds as disclosed herein, together with one or more carriers, diluents, or excipients, to a patient in need of relief from said infection, wherein said viral infection is an infection by flaviviridae viruses, including Dengue virus, West Nile virus, Yellow fever virus, Japanese encephalitis virus, Powassan virus, Zika virus, and Usutu virus; respiratory viruses, including MERS coronavirus, Influenza A H1N1 virus, Respiratory syncytial virus; Arenaviridae virus, including Tacaribe virus, Pichinde virus, Junin virus, Lassa fever virus, Lymphocytic Choriomeningitis virus; Filoviridae virus, including Ebolavirus, Marburgvirus; Togaviridae virus, including Venezuelan equine encephalitis virus, Eastern equine encephalitis virus, Western equine encephalitis virus, and Chikungunya virus; Mayarovirus; and Hantavirus.

In some other illustrative embodiments, the present invention relates to a compound having the following structure:

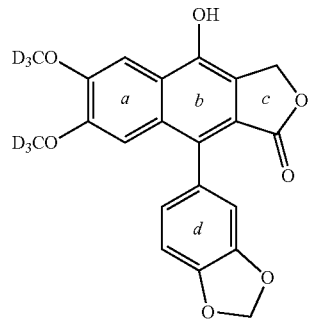
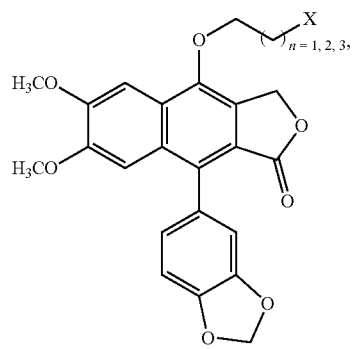
wherein X is selected from the group consisting of:
Made in C2/C3 version
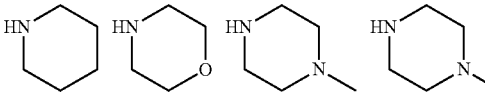
maybe
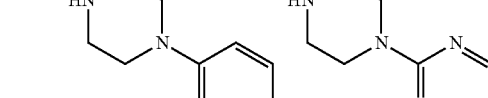
Make C3 version only
LogD up Clearance down
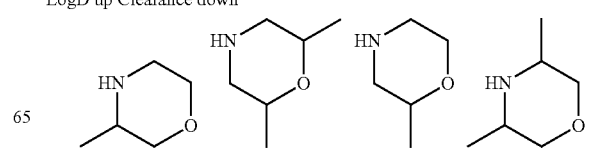
In some other illustrative embodiments, the present invention relates to a compound having the following structure:

-continued

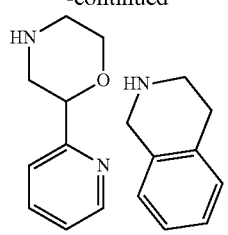

LogD down Clearence?

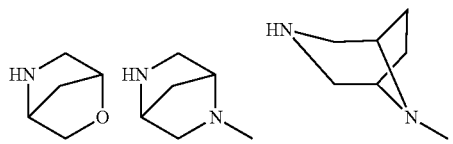

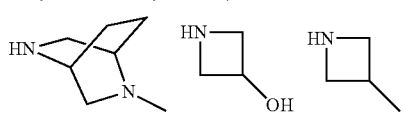

make C4 variants

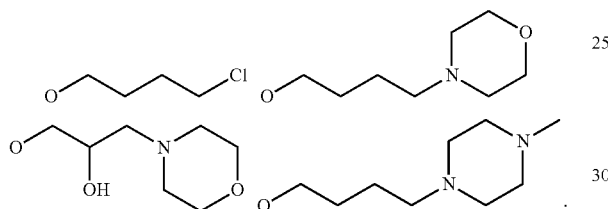

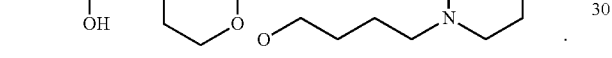

In some other illustrative embodiments, the present invention relates to a method for treating a patient with an infection, comprising the step of administering a therapeutically effective amount of one or more compounds as disclosed herein, together with one or more carriers, diluents, or excipients, to a patient in need of relief from said infection, wherein said compound is

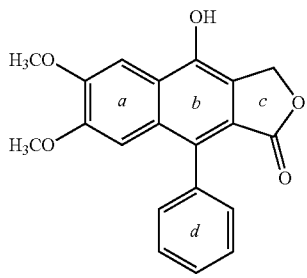

1

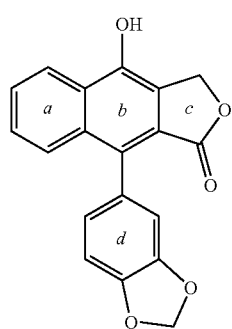

2

-continued

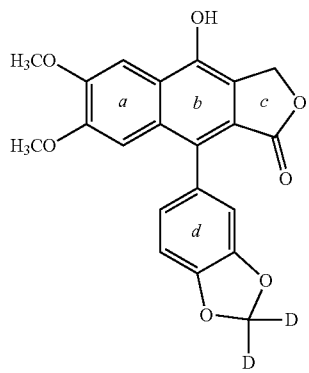

3

Fix the D-Ring

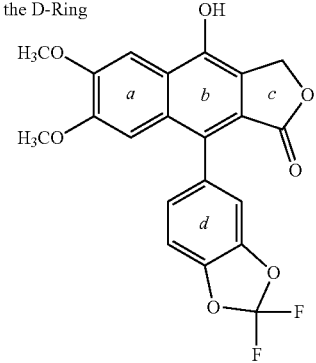

4

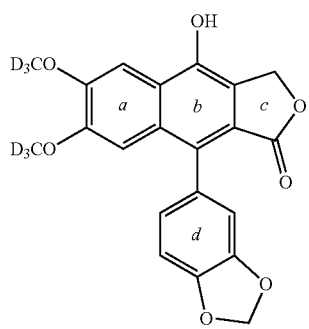

5

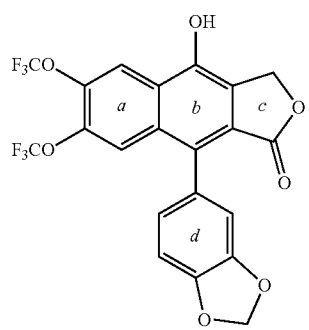

6

-continued

Fix the A-Ring

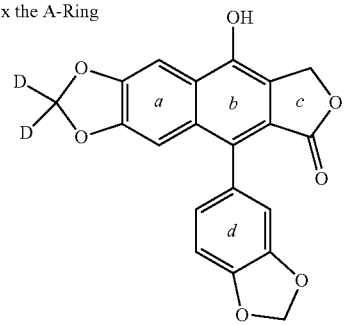

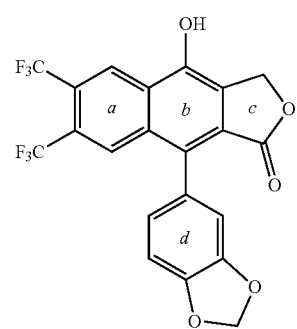

In some other illustrative embodiments, the present invention relates to a method for treating a patient with an infection, comprising the step of administering a therapeutically effective amount of one or more compounds as disclosed herein, together with one or more carriers, diluents, or excipients, to a patient in need of relief from said infection, wherein said compound is

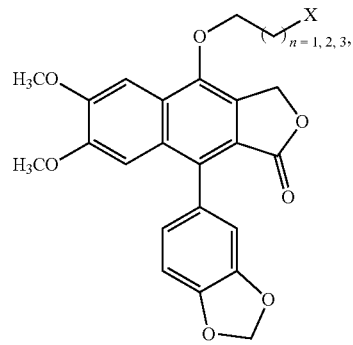

wherein X is selected from the group consisting of:

Made in C2/C3 version

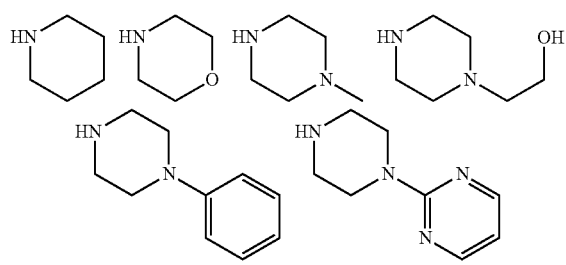

-continued

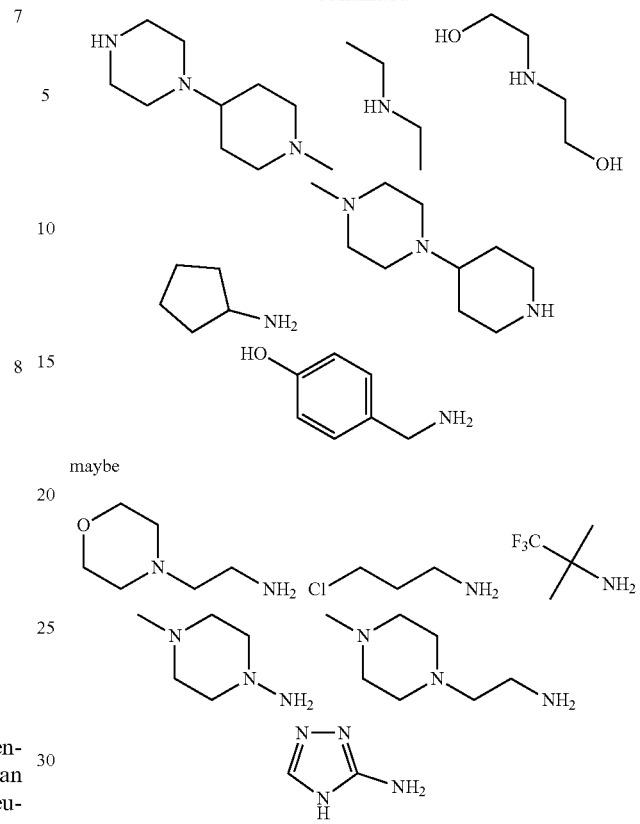

maybe

Make C3 version only
LogD up Clearance down

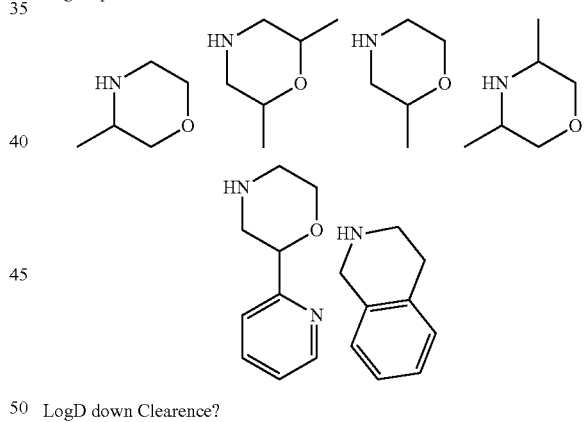

LogD down Clearence?

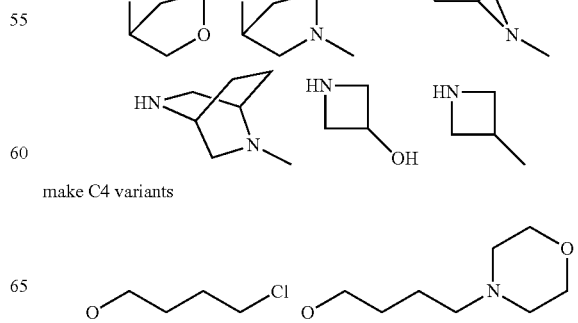

make C4 variants

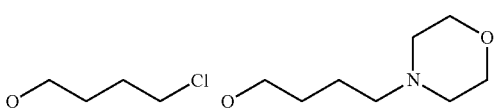

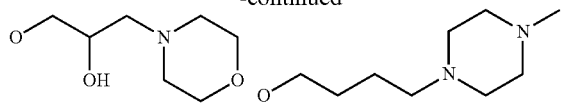

In some other illustrative embodiments, the present invention relates to a method for treating a patient with an infection, comprising the step of administering a therapeutically effective amount of one or more compounds as disclosed herein, together with one or more carriers, diluents, or excipients, to a patient in need of relief from said infection, wherein said compound is

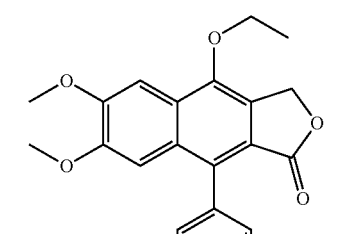

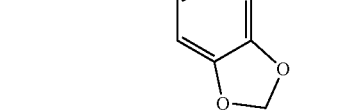

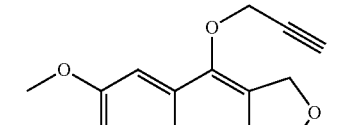

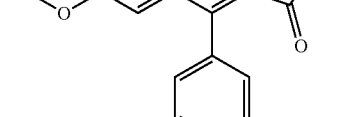

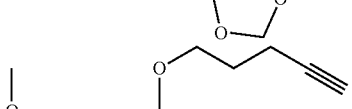

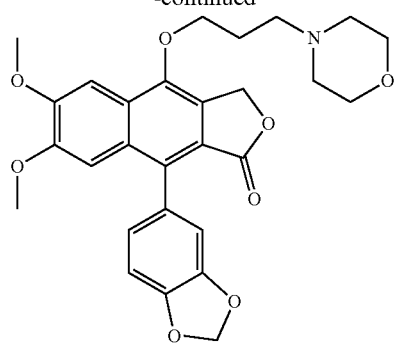

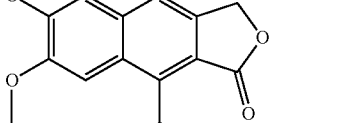

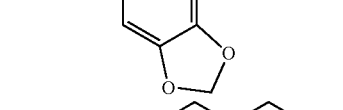

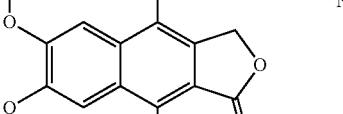

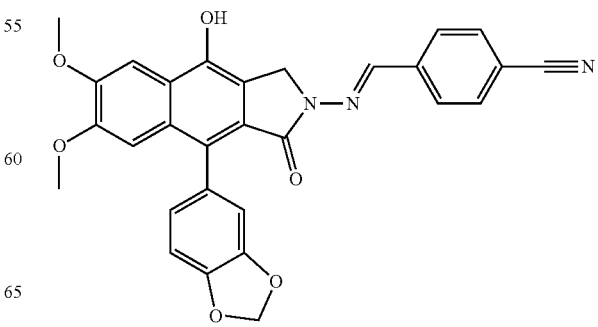

Endosomal acidification is a major pathway utilized by a wide number of viruses to facilitate cellular entry (Hunt, S R, et al., *J. Virol.* 2011, 85(3), 1257-1266). Most cellular infections by viruses begin when individual virions are taken into cells by one of several mechanisms of endocytosis. As the virion-containing endosomes mature toward lysosomes, the luminal pH decreases. Filoviruses, like many other virus types, require the endosomal acidification to trigger penetration of the membrane compartment to release the virus capsid into the cytosol and initiate replication. For enveloped viruses, penetration involves fusion of the virus membrane with that of the endosome. Additionally, for filoviruses, pH-dependent endosomal proteases need to cleave the membrane glycoprotein into a fusion-capable form (Chandran, K., et al., *Science* 2005, 308, 1643-1645). Acidification further induces a conformational change in the glycoprotein that allows it to fuse with the endosomal membrane and release of the viral ribonucleoprotein into the cell for initiation of the replicative phase of the viral lifecycle. Inhibitors of endosomal acidification are therefore potential broad-spectrum anti-viral compounds.

A primary host factor responsible for endosomal acidification is the multi-subunit enzyme vacuolar ($H^+$)-ATPase (V-ATPase), whose role is to couple proton transport across cellular membranes with hydrolysis of ATP. Many cellular and physiological processes are associated with V-ATPase function besides endosomal acidification, including roles in renal pH homeostasis, osteoclast bone remodeling, and sperm maturation (Cotter, K, et al., *Trends Biochem. Sci.* 2015, 40(10), 611-622). Different isoforms of V-ATPase are present in renal, neuronal, osteoclast and cancer cells along with the V-ATPase found in the endosomal membranes. Dysregulation of specific isoforms have been associated with diseases, including osteoporosis, metastatic cancers, male infertility and renal acidosis.

Many natural product inhibitors of V-ATPase have been identified that are generally hydrophobic macrocycles. Most of these natural inhibitors such as bafilomycin A1 have historic utility as cellular probes but lack the needed selectivity to serve as drug leads due to off-target effects (Huss, M. et al., *J. Exp. Biol.* 2009, 212(3), 341-346). There are disease indications where treatment for acute conditions could justify the pursuit of V-ATPase inhibition. The case would be valid if useful selectivity can be exhibited through structural modifications of the inhibitor chemotype. Diphyllin is an arylnaphthalene lignan natural product that represents a scaffold distinct from previous known natural product V-ATPase inhibitors. Cellular activities demonstrated for diphyllin have shown useful anti-tumor and anti-osteoclast activity, as well potential anti-viral activity in early testing using influenza and Dengue virus models (Konig, R. et al., *Nature* 2010, 463, 813-817; Chen, H W, et al., *Antiviral Res.* 2013, 99, 371-382)). The inhibition of pH-dependent virus infection prompted our evaluation of diphyllin as a scaffold for the development of selective V-ATPase inhibitors as potential broad-spectrum antiviral agents.

There are challenges to address for any targeted antiviral approach with both advantages and disadvantages to host-specific approaches.[21] Herein, we report the identification of several novel diphyllin derivatives that are potent inhibitors of V-ATPase and EBOV and MARV infection of macrophages by phenotypic screening of a small library of diphyllin derivatives. The compounds were first screened for inhibitors of EBOV cellular entry. Positive hits were assayed for the ability to inhibit cellular vesicle acidification. Compounds selected from these screens were ranked based on their selectivity between cytotoxicity and cellular endosomal acidification in two cell lines and their ability to inhibit V-ATPase function in isolated vesicles. The top 4 compounds were then classified on their ability to inhibit EBOV and MARV infections and cytotoxicity in primary human macrophages due to their importance as a primary site of infection (Rivera, A., et al., *J. Leukoc. Biol.* 2016, 100, 889-904). Overall, this approach demonstrates the use of phenotypic screens to down-select novel V-ATPase inhibitors compounds that selectively inhibit filovirus infections.

Four series of diphyllin-related compounds were synthesized to determine the tolerance of modifications of the lactone ring and alkylation of the phenol group (Scheme 1). Synthesis of intermediate 1a was completed using modified procedures from Charlton et al (Charlton, J L, *J. Nat. Prod.* 1998, 61, 1447-1451). A set of imide derivatives were synthesized by condensation of primary amines with intermediate 1a (Scheme 1). Diphyllin (2a) was synthesized from intermediate 1a by reduction with lithium aluminum hydride in THF and the final three series were synthesized with 2a as the starting material. A set of phenol derivatives were synthesized by Williamson ether synthesis with a series of propyl derivatives incorporating hydrophilic and hydrophobic groups at the terminus opposite 2a. The hydrazone derivatives were synthesized by first using the nucleophilic attack of hydrazine upon diphyllin's lactone ring to create the hydrazide derivative 3a. Then, condensation of 3a with a set of substituted benzyl aldehydes provided a hydrazone series. Ring-opened amides were synthesized by nucleophilic attack of both primary and secondary amines upon the lactone ring of diphyllin to yield 1 secondary amide and 4 tertiary amides.

All four classes were screened for the ability to inhibit ebolavirus infection using a GFP-expressing Ebola pseudovirus in HeLa cells. Compounds that significantly inhibited infection at 12.5 µM were then ranked by $IC_{50}$ against infection. None of the ring-opened amides and only the acetylated imide 1e proved active in this screen. However, hydrazone derivatives showed varying degrees of activity with analogs bearing electron-withdrawing groups at the para-position being the potent in the class. Phenol ether derivatives demonstrated the greatest potency amongst those tested and 2c exhibited a 10-fold improvement in potency compared to diphyllin (Table 1). In general, hydrophobic alkyl ethers appeared to be the more potent but the hydrophilic morpholino and piperazinyl acetate also exhibited improved potency compared to diphyllin.

Scheme 1. Synthesis of Diphyllin Derivatives*

*(a) LiAlH₄, THF, 0° C., 1 hr (92%); (b) H₂NNH₂, MeOH, reflux, 12 h (66%); (c) RNH₂, MeOH, reflux, 2-12 hr (57-93%); (d) RX, K₂CO₃, DMSO, 60° C., 1-48 hr (36-91%); (e) R₂NH, 0.5 M NaOH in MeOH, reflux, 12-18 h (16-57%); (f) R₃CHO, MeOH, relux, 6-12 hr (47-88%).

TABLE 1

Activity against Ebolavirus infection and cellular endosomal acidification

| ID | R1 | R2 | X | Y | EBOV IC$_{50}$ (nM)[a] | HEK AO IC$_{50}$ (nM)[b] | HEK CC$_{50}$ (μM) | HEK SI[c] |
|---|---|---|---|---|---|---|---|---|
| Baf A1 | — | — | — | — | 14.9 ± 8.93 | 40.5 ± 3.31 | 0.32 ± 0.042 | 7.90 |
| 1e | (acetyl, CH$_3$C(=O)-) | CH$_2$CH$_2$OH | N | C=O | 5400 ± 2920 | >10000 | — | — |
| 2a | H | — | O | CH$_2$ | 678 ± 161 | 476 ± 60.1 | 17.8 ± 4.31 | 37.4 |
| 2b | CH$_3$ | — | O | CH$_2$ | 171 ± 40.2 | 265 ± 58.6 | 5.73 ± 0.841 | 21.6 |
| 2c | CH$_2$CH$_3$ | — | O | CH$_2$ | 112 ± 14.7 | 254 ± 49.0 | 2.38 ± 22.9 | 9.37 |
| 2d | propargyl | — | O | CH$_2$ | 175 ± 21.7 | 263 ± 46.6 | 2.04 ± 26.8 | 7.76 |
| 2e | pent-4-ynyl | — | O | CH$_2$ | 73.2 ± 11.9 | 102 ± 19.0 | 4.04 ± 2.03 | 39.6 |
| 2f | cyanoalkyl | — | O | CH$_2$ | 93.1 ± 26.8 | 98.7 ± 29.5 | 3.31 ± 0.740 | 31.7 |
| 2g | morpholinopropyl | — | O | CH$_2$ | 107 ± 23.7 | 74.3 ± 23.9 | 11.2 ± 2.49 | 151 |
| 2h | 4-(ethoxycarbonylmethyl)piperazinylpropyl | — | O | CH$_2$ | 132 ± 32.3 | 172 ± 40.6 | 24.7 ± 2.68 | 144 |
| 2i | 4-(2-hydroxyethyl)piperazinylpropyl | — | O | CH$_2$ | 76.2 ± 14.6 | 104 ± 21.2 | | |
| 3a | H | NH$_2$ | N | CH$_2$ | 3940 ± 604 | 9060 ± 893 | 48.9 ± 3.61 | 5.40 |
| 3b | H | N=CH-phenyl | N | CH$_2$ | 6630 ± 437 | >10000 | — | — |
| 3c | H | N=CH-pyridyl | N | CH$_2$ | 4480 ± 467 | 8710 ± 769 | 49.9 ± 15.9 | 5.73 |

TABLE 1-continued

Activity against Ebolavirus infection and cellular endosomal acidification

[Structure: naphtho-fused ring system with OR1, two OMe groups, Y, X—R2, and a benzodioxole substituent; ketone C=O]

| ID | R1 | R2 | X | Y | EBOV IC$_{50}$ (nM)[a] | HEK AO IC$_{50}$ (nM)[b] | HEK CC$_{50}$ (μM) | HEK SI[c] |
|---|---|---|---|---|---|---|---|---|
| 3d | H | —N=CH—C$_6$H$_4$—Cl | N | CH$_2$ | 1170 ± 518 | 9930 ± 140 | 28.4 ± 2.71 | 2.86 |
| 3g | H | —N=CH—C$_6$H$_4$—C≡N | N | CH$_2$ | 1690 ± 233 | >10000 | — | — |
| 3h | H | —N=CH—C$_6$F$_5$ | N | CH$_2$ | 8740 ± 2180 | >10000 | — | — |

[a]Inhibition of GFP-expressing EBOV GP pseudotyped vesicular stomatitis virus (VSV) infection of HeLa cells; mean±SEM (n = 6).
[b]Inhibition of cellular endosomal acidification in HEK-293 cells; mean±SEM (n = 9).
[c]Selectivity index of endosomal acidification in HEK-293 cells over cytotoxicity.

To evaluate a role for V-ATPase function as a mechanism for inhibition of EBOV cell entry, all active compounds were screened for the ability to inhibit endosomal acidification in HEK293 cells. The dichromic dye acridine orange (AO) when neutral, freely passes through cells but accumulates in acidic endosomal compartments as the dye becomes protonated and aggregates. The neutral dye emits at 530 nm while the pH-dependent, aggregated dye shifts its emission to 650 nm which can be used to detect vesicle acidification in cells (Chen, H W, et al., Antiviral Res. 2013, 99, 371-382). Candidate V-ATPase inhibitors were identified in HEK293 cells by a significant decrease in the 650 nm/530 nm ratio of AO fluorescence when compared to the vehicle control. The IC$_{50}$ values for inhibition of endosomal acidification where then compared with the cytotoxicity values (CC50) in the same cell lines to determine if these activities could be separated. Overall, the relative potencies of the EBOV cell entry effects track with the endosome acidification. In this assay, known V-ATPase inhibitors bafilomycin and diphyllin (2a) showed a potency for endosome acidification that was consistent with the EBOV cell entry. The potency of the well-established V-ATPase inhibitor bafilomycin A1 was greater in the assay but its cytotoxicity was enhanced as well.

The acidification screen identified significant differences among the three diphyllin analog classes selected from the original screen. Imide 1e did not cause a significant change in the fluorescence ratio indicating lack of an effect on endosomal acidification. Hydrazide 3a and four of the six active hydrazones moderately inhibited acidification but none achieved the level of inhibition observed with 2a. Only the hydrazide precursor 3a and hydrazones 3c and 3d inhibited acidification to the level observed with Baf A1 at concentrations higher than 10 μM but these compounds proved to be 18-fold less potent than diphyllin. The cytotoxicity of this class of compounds had minimal separation from inhibition of endosomal acidification. The activities of the class may have activity against a separate target during EBOV entry assay because of the 2-10 fold difference between IC50 values in the two assays.

The phenol derivatives presented a different profile from the other classes when endosomal acidification and cytotoxicity were measured. All phenol derivatives inhibited acidification to a similar level to that of Baf A1 and all represented improved IC50 values compared with diphyllin. Compounds 2b and 2c were most potent in A549 cells but were roughly 4-fold less potent in HEK 293 cells (Table 2). We used A549 cell line activity to predict utility of an antiviral effect selective compounds based on the fact that this tumor derived cell line requires high activity of V-ATPase for growth and survival.

TABLE 2

A549 Endosomal acidification, Cytotoxicity and SI data

| ID | A549 AO IC50 (nM) | A549 CC50 (μM) | A549 SI |
|---|---|---|---|
| Bafilomycin A1 | 21.3 ± 2.55 | 0.479 ± 0.266 | 22.5 |
| 2a | 149 ± 20.5 | 50.1 ± 15.5 | 336 |
| 3a | 8110 ± 670 | 28.7 ± 16.6 | 3.40 |
| 3c | 11,600 ± 840 | 50.1 ± 27.7 | 4.32 |
| 3d | 8440 ± 367 | 78.0 ± 26.4 | 9.24 |
| 2b | 58.2 ± 8.76 | >100 | >1720 |
| 2c | 52.4 ± 19.3 | 77.4 ± 11.0 | >1480 |
| 2e | 84.8 ± 11.9 | >100 | >1180 |
| 2g | 56.1 ± 15.9 | >100 | >1780 |
| 2h | 101 ± 13.8 | >100 | >990 |

While the lipophilic derivatives demonstrated at least 3-fold greater potency than diphyllin, they also exhibited 3 to 10-fold increased toxicity in HEK293 cells. Overall, far less toxicity was observed in A549 cells for all tested ethers compared with the toxicity in HEK293 cells. The morpholino ether derivative 2g was the potent derivative both cell lines and demonstrated roughly equipotent cytotoxicity. The piperazinyl acetate ether 2h demonstrated less activity compared to the morpholino but also had lower toxicity and a similar SI range to 2g in HEK293 cells. STATE 2i result here. The hydrophilic basic derivatives were therefore able to expand the selectivity window between endosomal acidification and cytotoxicity in HEK293 cells compared to diphyllin.

Figure 1B:
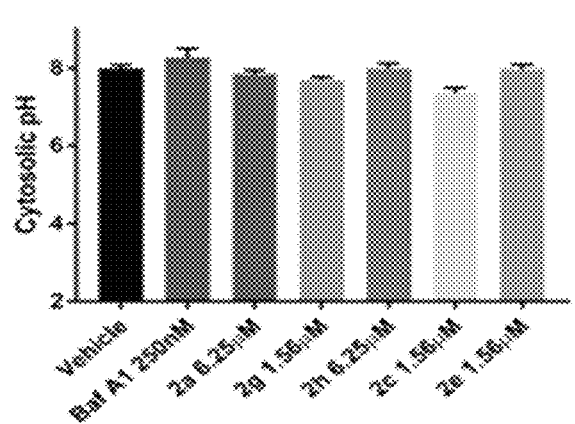
FIG. 1B demonstrates cytoslic pH measured by BCECF-AM staining (10 μg/ml) of HEK293 cells after 4 hr treatment with chosen inhibitor or vehicle, demonstrating that diphyllin derivatives cause an increase in intracellular vesicle pH but no corresponding change in cytosolic pH.
Figure 1C:
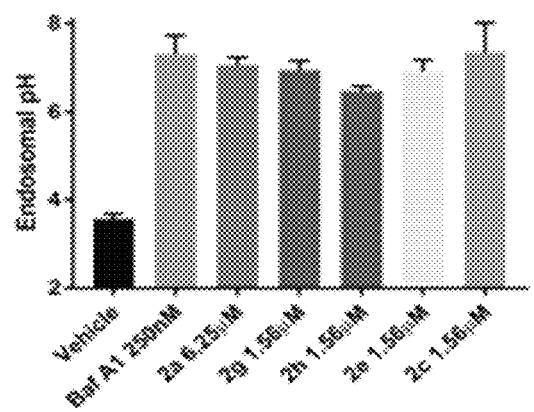
FIG. 1C shows endosomal pH measured by FITC-dextran staining of HEK293 cells after 4 hr treatment with chosen inhibitor or vehicle, demonstrating that diphyllin derivatives cause an increase in intracellular vesicle pH but no corresponding change in cytosolic pH.
Figure 2:
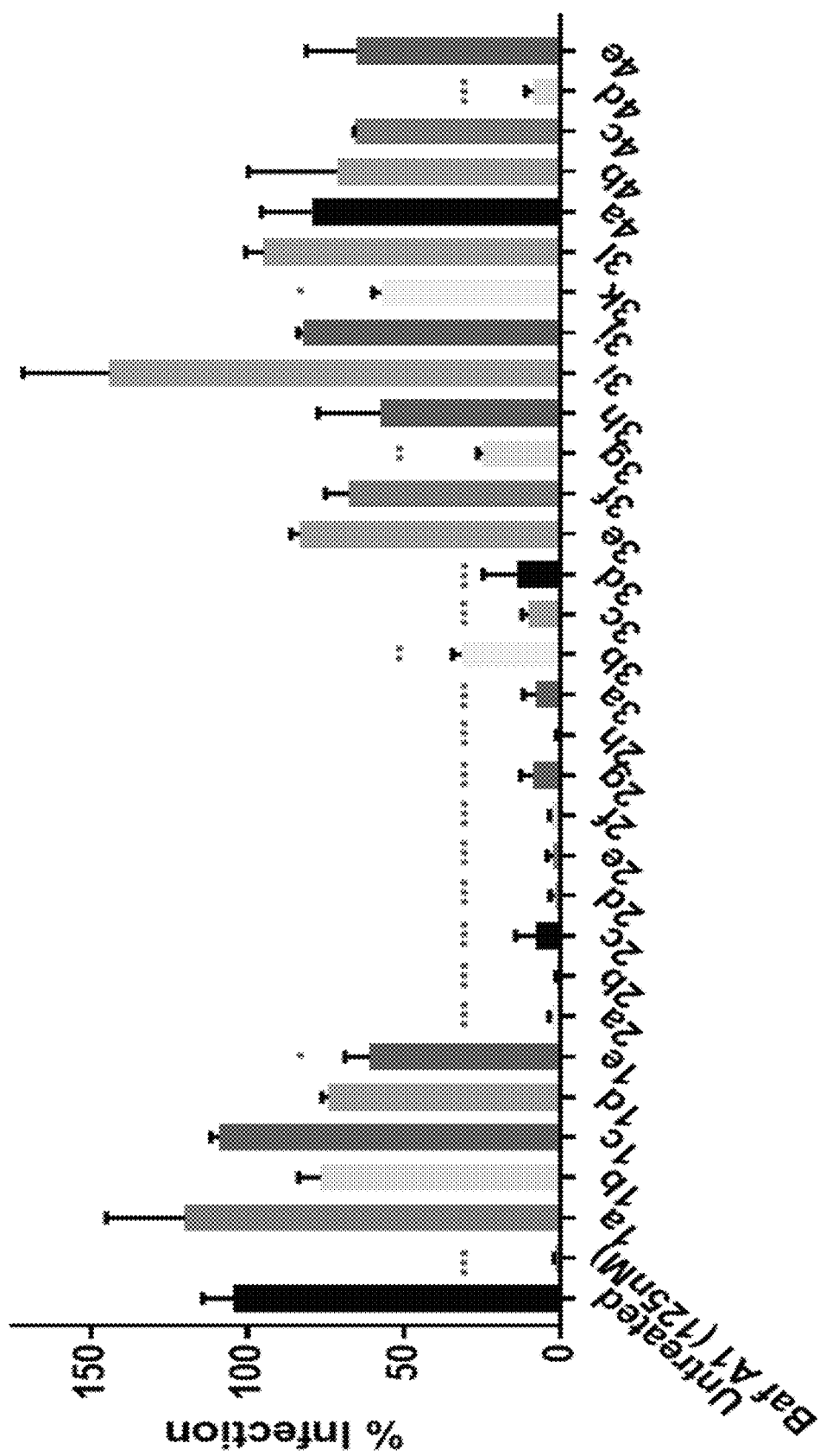
FIG. 2 depicts antiviral screening of Ebolavirus infection at 12.5 μM concentration in HeLa cells. *p<0.05, p>0.005, *p>0.001.
Figure 3:
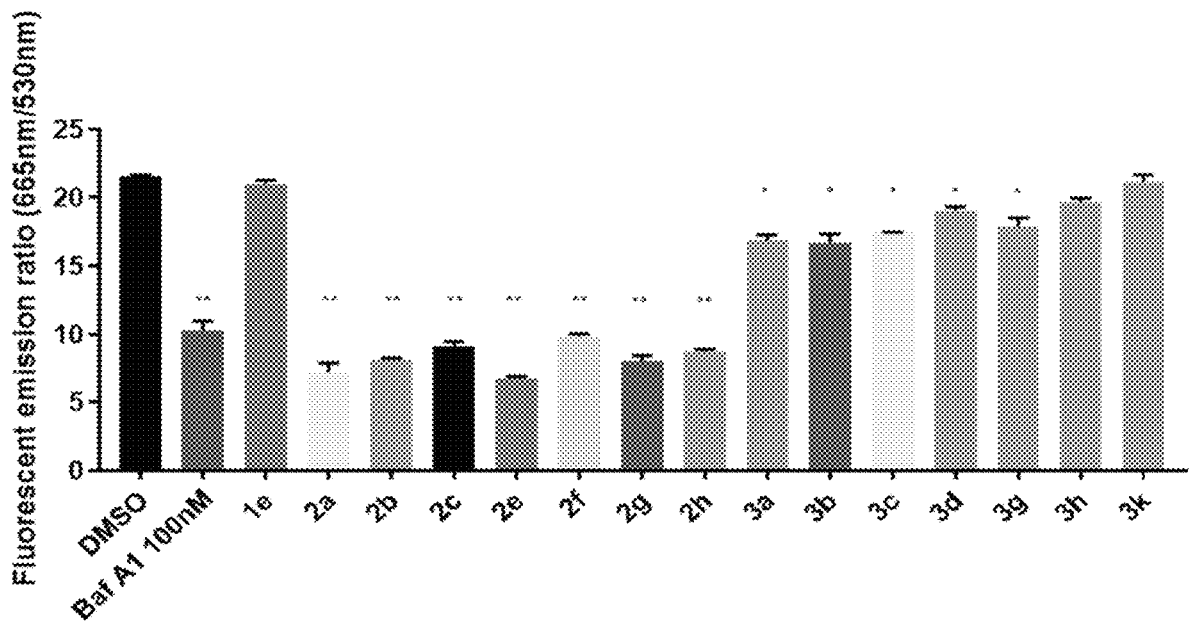
FIG. 3 shows screening with HEK293 and A549 cells for Acridine Orange (AO) activity.
Figure 4:
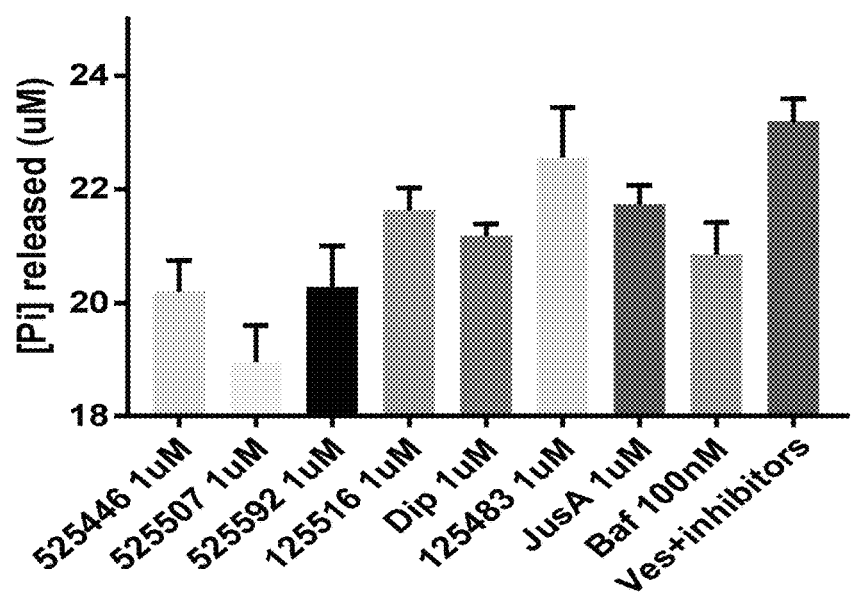
FIG. 4 depicts screening with HEK293 vesicles for ATPase activity at 1 μM concentration.

Since acridine orange is a promiscuous dye and can integrate with nucleic acids to also give a fluorescent emission, FITC-dextran fluorescence, which also is affected by pH, was used to further assess our top compounds ability change endosomal pH. For the measurement of endosomal pH, HEK293 cells were incubated with FITC-dextran overnight before treatment with inhibitors for 4 h. FITC-dextran fluorescence was standardized in vehicle treated cells using HEPES-phosphate buffers with 10 μg/ml of nigericin at pH values from 4-8 tor a standard pH curve. The ionophore nigericin was added to equilibrate the cell's internal pH with the external buffer pH. Both diphyllin and the top compounds from the acridine orange assay were assayed at several concentrations to determine if they caused alkalization of endosomal pH to a similar degree that is observed by bafilomycin A1 treatment. Both diphyllin and all tested derivatives caused endosomal pH to return to around pH 7 at low micromolar concentrations (1-3 μM; FIG. 1C).

To ensure that the change in endosomal pH was not due to an overall change in cellular pH, cytosolic pH was measured with the BCECF-AM dye mixture. Following the same inhibitor treatment of HEK293 cells for 3.5 h, the BCECF-AM dye mixture was added to cells and incubated for 30 min before cytosolic pH was quantified using the same HEPES-phosphate buffers used for endosomal pH. Treatment with bafilomycin A1, diphyllin and its derivatives showed no significant change in cytosolic pH compared to the vehicle treated control (FIG. 1B).

TABLE 3

Biochemical Activity of Diphyllin and Derivatives against V-ATPase

| ID | AO Quenching $IC_{50}$ (nM) | ATPase Inhibition |
|---|---|---|
| Baf A1 | 24.8 ± 2.66 | (+) |
| 2a | 189 ± 1.66 | (+) |
| 3c | 423 ± 3.96 | (−) |
| 3d | 724 ± 13.5 | (−) |
| 2b | 47.5 ± 5.28 | (+) |
| 2c | 16.9 ± 3.72 | (+) |
| 2e | 11.7 ± 2.97 | (+) |
| 2g | 27.4 ± 19.4 | (+) |
| 2h | 114 ± 1.71 | (+) |
| 2i | 61.0 ± 2.84 | (+) |

To assess if ability of diphyllin and derivatives to inhibit endosomal acidification is due to the expected ability of diphyllin to inhibit V-ATPase activity, compounds were assayed for inhibition of both the proton-pumping and ATPase functions of the isolated V-ATPase enzyme. V-ATPase containing vesicles were isolated from HEK293 cells following methods similar to that found in Aldrich et al. (Zoncu, R. et al., Science 2011, 334, 678-683). To determine the effect of compounds upon the proton pumping function of V-ATPase, isolated vesicles were incubated with acridine orange and the compound or vehicle for 1 h prior to the addition of ATP which initiated pump activity. The quenching of the 530 nm emission of acridine orange was measured over 1h before addition of nigericin to relax the proton gradient within vesicles. $IC_{50}$ values against the proton-pumping function of V-ATPase could be assessed by quantifying the change in Acridine Orange (AO) fluorescence immediately before and after the addition of nigericin. Compounds that were active at 10 μM against the cellular endosomal acidification in HEK293 and A549 cells were screened at 1 μM through this assay and IC50 values for compounds that exhibited significant changes in the amount of AO quenched were identified.

Diphyllin appeared to be about 7.5 times less potent than bafilomycin A1 at inhibiting V-ATPase-mediated fluorescent quenching (Table 3). The hydrazone derivatives 3c and 3d were 2 and 4 times less effective than diphyllin, respectively, which matches with the compounds being less active in previous assays. All phenol derivatives had improved activity relative to diphyllin. The lipophilic phenol derivatives had improved potencies with derivative 2e being 17 times that of diphyllin and 2 times better activity of Bafilomycin A1 at inhibiting the proton pumping activity of V-ATPase. Hydrophilic phenol derivatives were less active than the lipophilic derivatives but derivative 2g was still 7 times better activity compared to diphyllin and had similar potency to Bafilomycin A1.

To ascertain if diphyllin and derivatives also inhibit the ATPase function of V-ATPase, ATP hydrolysis in the presence of isolated V-ATPase-containing vesicles from HEK293 cells was quantified. Vesicles were incubated with compounds that were active at 10 μM against the cellular endosomal acidification for 1 h at a concentration of 1 μM. The amount of ATP hydrolyzed after 1 h was measured using malachite green to quantify free phosphate released by ATP hydrolysis. Diphyllin and the derivatives 2b, 2c, 2e, 2g and 2h all inhibited ATP hydrolysis to a similar extent at 1 μM compared to Bafilomycin A1 (Table 3). However, the hydrazone derivatives did not cause a significant decrease in free phosphate compared to the vehicle control.

TABLE 4

Pan-filoviral activity and cytotoxicities of top diphyllin derivatives in HeLa infection model and PHM

| ID | HeLa CC$_{50}$ (μM)$^a$ | EBOV IC$_{50}$/CC$_{50}$$^b$ | MARV IC$_{50}$ (nM)$^c$ | MARV IC$_{50}$/CC$_{50}$$^b$ | PHM EBOV IC$_{50}$(nM) | PHM IC$_{50}$/CC$_{50}$$^b$ |
|---|---|---|---|---|---|---|
| 2a | >100 | >147 | 1770 ± 80.0 | >56.5 | 678 ± 218 | >73.7 |
| 2e | 36.5 ± 7.13 | 499 | 402 ± 45.9 | 90.8 | 240 ± 36.4 | >416 |
| 2g | 36.6 ± 18.8 | 342 | 135 ± 11.4 | 271 | 57.7 ± 8.6 | >1530 |
| 2h | 63.0 ± 11.2 | 477 | 81.6 ± 28.7 | 772 | 256 ± 21.3 | >391 |

$^a$Cellular cytotoxicity for select compounds; mean:SEM (n = 6).
$^b$Selectivity index between cytotoxicity and inhibition of infection.
$^c$Inhibition of GFP-expressing MARV GP pseudotyped vesicular stomatitis virus (VSV) infection of Hela cells; mean:SEM (n = 6).
[d] Inhibition of replication-competent EBOV infection; mean:SEM (n = 6).

The top lead candidates were further evaluated for the capacity to inhibit MARV cellular entry. Hydrophilic and hydrophobic phenol ether derivatives, 2e, 2g, and 2h were further assessed for activity against Marburg virus infection along with derivative 2h because of its increased SI value. The hydrophobic derivative 2e and diphyllin had a significant drop in potency against Marburg virus compared with their activity against EBOV infection (Table 4). Hydrophilic derivative 2g exhibited a 2-fold decrease in potency while 2h had a slight increase in potency compared to their activity against EBOV infection (Table 4). These activities suggest that the compounds have activity against multiple class of filoviruses. Selectivity indices were also increased in the infection model which indicates that compounds will selectively block filoviral infection while not causing cytotoxicity (Table 4). However, toxicities were not as high as those observed in the HEK293 model.

In some illustrative embodiments, additional compounds are prepared according to Scheme 2 below.

Scheme 2.

(a) R-NH$_2$, MeOH, reflux, 16 h;
(b) LiAlH$_4$, THF, 0° C., 1 h;
(c) H$_2$NNH$_2$, MeOH, reflux, 12 h;
(d) Zn, AcOH, reflux, 48 h.

-continued
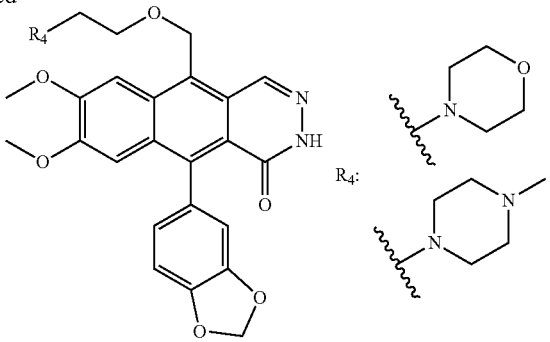
(a) (CH₂)₂CHCH₂OCOCl, Et₃N, Dioxane, RT, 1 h; (b) R-X, K₂CO₃, DMSO, 16 h: (c) TFA, DCM, 4 h.
In some illustrative embodiments, additional compounds are prepared according to Scheme 3 below.
wherein X is selected from the group consisting of:
Scheme 3.
Made in C2/C3 version
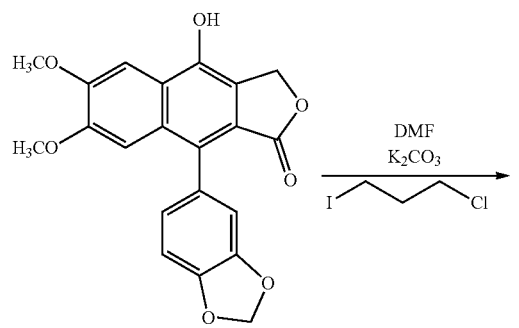
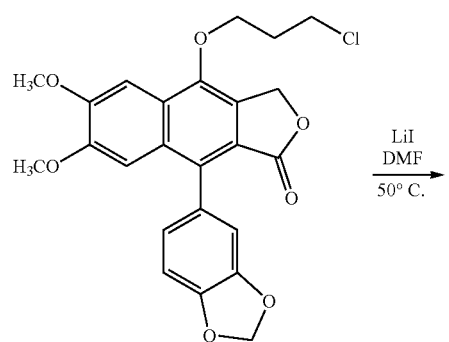
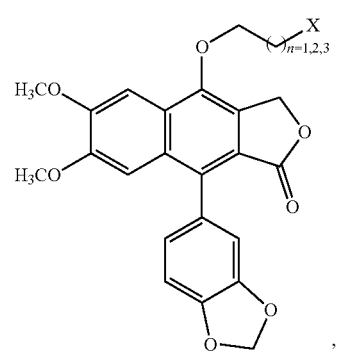
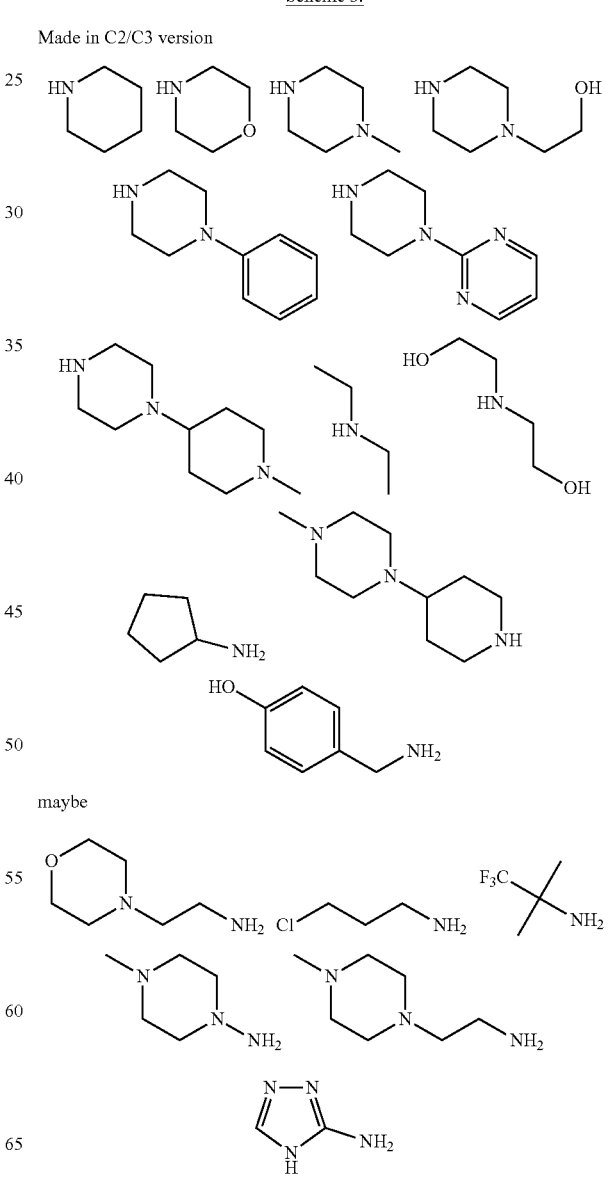
maybe Make C3 version only
LogD up Clearance down
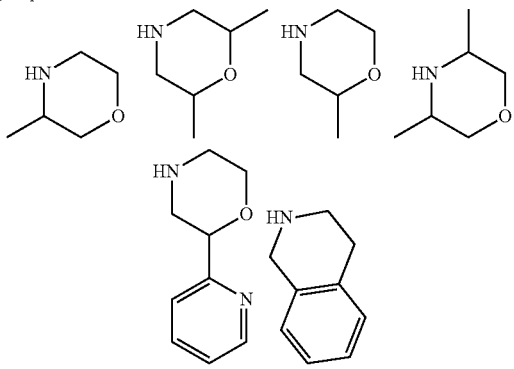
LogD down Clearence?
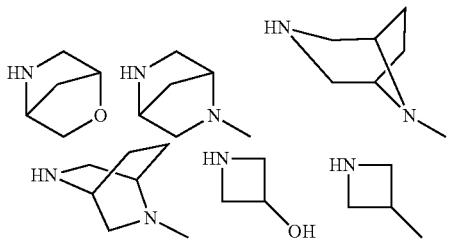
make C4 variants
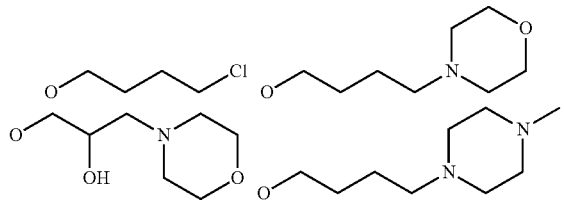
In summary, we syn Synthetic Methods General: All commercially purchased reagents used in this study were of the highest purity available. Regular solvents (THF, EtOAc, $CH_2Cl_2$, DMSO, etc.) were used as received without further purification. NMR spectra were recorded at 298 K on Bruker ARX300, DRX500, and Avance-III-800 spectrometers using $[D_6]$DMSO as the solvent and internal reference ($\delta_H$=2.46 ppm, $\delta_C$=40.0 ppm). Chemical shifts are reported in parts per million (ppm), and coupling constants (J) are given in Hertz (Hz). The proton spectra are reported as follows: d (multiplicity, coupling constant, number of protons). Proton multiplicities are designated as follows: s (singlet), d (doublet), t (triplet), q (quartet), and m (multiplet). High-resolution mass spectra were taken using an Agilent 6550 Q-Tof mass spectrometer using electrospray ionization (ESI). Low-resolution mass spectra were taken on an Advion expression Compact Mass Spectrometer using ESI. High-performance liquid chromatography (HPLC) was performed on a Hitachi D-7000 system using a Phenomenex Kromasil C18 column with water and acetonitrile (MeCN) solvents containing 1% trifluoroacetic acid (TFA). HPLC was used for purity determination using a general method as follows: 5% MeCN for 1 min, 5-100% MeCN over 15 min, 100% MeCN for 2 min, 100-5% MeCN for 2 min.

9-(benzo[d][1,3]dioxol-5-yl)-4-hydroxy-6,7-dimethoxynaphtho[2,3-c]furan-1(3H)-one (2a)-diethyl 1-(benzo[d][1,3]dioxol-5-yl)-4-hydroxy-6,7-dimethoxynaphthalene-2,3-dicarboxylate (1a). ESI-MS (ESI+) m/z: calculated 381.0969 $[M+H]^+$, found 381.0964 $[M+H]^+$.

Imide Synthesis 2-amino-4-(benzo[d][1,3]dioxol-5-yl)-9-hydroxy-6,7-dimethoxy-1H-benzo[f]isoindole-1,3(2H)-dione (1b)-1a (148 mg, 0.316 mmol) was dissolved in methanol (5 ml) and heated to reflux. Hydrazine hydrate (500 ul, ~60% solution) was added dropwise and the reaction was allowed to react overnight. Precipitate formed upon cooling the mixture to −20° C. and was filtered off to yield a pure, yellow solid (121 mg, 93%). $^1$H NMR (500 MHz, DMSO-$d_6$): 8.53 (s, 1H), 7.68 (s, 1H), 7.11 (s, 1H), 6.97 (d, J=10 Hz, 1H), 6.86 (s, 1H), 6.85 (d, 1.5 Hz, 1H), 6.09 (d, J=20 Hz, 2H), 4.08 (s, 3H), 4.07 (s, 2H), 3.83 (s, 3H). LC-MS: m/z=409.2 $[M+H]^+$.

4-(benzo[d][1,3]dioxol-5-yl)-9-hydroxy-2-(2-hydroxyethyl)-6,7-dimethoxy-1H-benzo[f]isoindole-1,3(2H)-dione (1c)-1a (150 mg, 0.320 mmol) was dissolved in methanol (5 ml) and heated to reflux. Ethanolamine (1 ml, 1.012 g, 16.6 mmol) was added dropwise and the reaction was allowed to react overnight. The reaction was cooled and methanol was removed by rotary evaporation. The remaining liquid was acidified by 1M HCl and the resulting precipitate was collected by vacuum filtration. The precipitate was recrystallized from toluene and methanol to yield 120 mg (85%) of yellow solid. $^1$H NMR (500 MHz, DMSO-$d_6$): 7.78 (s, 1H), 7.03 (s, 1H), 6.93 (d, J=10 Hz, 1H), 6.82 (s, 1H), 6.80 (d, J=10 Hz, 1H), 6.02 (d, J=5 Hz, 2H), 4.59 (s, 2H), 3.97 (s, 3H), 3.72 (s, 3H), 3.68 (s, 4H). LC-MS: m/z=438.1 $[M+H]^+$.

4-(benzo[d][1,3]dioxol-5-yl)-9-hydroxy-6,7-dimethoxy-2-(2-morpholinoethyl)-1H-benzo[f]isoindole-1,3(2H)-dione (1d)-1a (102 mg, 0.218 mmol) was dissolved in methanol (5 ml) and heated to reflux. Ethanolamine (1 ml, 1.012 g, 16.6 mmol) was added dropwise and the reaction was allowed to react overnight. The reaction was cooled and methanol was removed by rotary evaporation. The remaining liquid was acidified by 1M HCl and the resulting precipitate was collected by vacuum filtration. The filtrate was extracted with ethyl acetate (3×20 ml) and DCM (3×20 ml). The organic layers were combined, dried with anhydrous sodium sulfate and concentrated by rotovap. The precipitate was recrystallized from toluene and methanol to yield an amorphous, yellow solid (61 mg, %).

9-(benzo[d][1,3]dioxol-5-yl)-2-(2-hydroxyethyl)-6,7-dimethoxy-1,3-dioxo-2,3-dihydro-1H-benzo[f]isoindol-4-yl acetate (1e)-Yield: ESI-MS (ESI+) m/z: calculated 480.1295 $[M+H]^+$, found 480.1289 $[M+H]^+$.

General Procedure for synthesis of chloro-alkene precursors: 1.1 mL (1.72 g, 11 mmol; 1.5 equiv.) of 1-bromo-3-chloropropane and amine component (1 eq) were dissolved in acetonitrile (40 mL) at room temperature while stirring. 4.1 mL (2 equiv.) of triethylamine was then added dropwise. The reaction mixture was stirred at room temperature for 24-48 hours. When complete, the solvent was removed under reduced pressure to yield a crude oil. The crude oil was purified by normal phase silica gel chromatography (DCM/MeOH 100/0 to 50/50) to yield the pure oil.

4-(3-chloropropyl)morpholine-Yield: 351 mg, 30%. LC-MS: m/z=164.1 $[M+H]^+$.

ethyl 2-(4-(3-chloropropyl)piperazin-1-yl)acetate-Yield: 654 mg, 36%. LC-MS: m/z=248.2 $[M+H]^+$.

2-(4-(3-chloropropyl)piperazin-1-yl)ethan-1-ol-Yield: 551 mg, 36%. LC-MS: m/z=207.2 $[M+H]^+$.

1-(3-chloropropyl)-4-methylpiperazine-Yield: 481 mg, 37%. LC-MS: m/z=177.1 $[M+H]^+$.

General synthetic procedure for hydrophobic phenol ether derivatives: 2a (50 mg, 0.131 mmol, 1 eq), bromoalkane (2 eq), and potassium carbonate (91 mg, 0.655 mmol, 5 eq) were dissolved in dimethyl sulfoxide (6 mL). The reaction was heated to reflux overnight (16-20 h). The reaction was then cooled to room temperature and 20 mL of distilled water was added to the flask. The mixture was added to a separatory funnel and extracted with dichloromethane (3×20 mL). The organic layers were combined and washed with distilled water (30 mL) and brine (30 mL) before concentrating the organic layers under reduced pressure. The crude product was purified with normal phase silica gel chromatography (Hexanes/EtOAc 100/0 to 80/100) to yield the pure solid.

9-(benzo[d][1,3]dioxol-5-yl)-4,6,7-trimethoxynaphtho[2,3-c]furan-1(3H)-one (2b)- Yield: 46 mg, 91%. ESI-MS (ESI+) m/z: calculated 395.1125 $[M+H]^+$, found 395.1125 $[M+H]^+$.

9-(benzo[d][1,3]dioxol-5-yl)-4-ethoxy-6,7-dimethoxynaphtho[2,3-c]furan-1(3H)-one (2c)-Yield: 40 mg, 74%. $^1$H NMR (500 MHz, DMSO-$d_6$) δ 7.48 (s, 1H), 6.99 (d, J=7.9 Hz, 1H), 6.92 (s, 1H), 6.84 (d, J=1.7 Hz, 1H), 6.72 (dd, J=7.9, 1.7 Hz, 1H), 6.09 (s, 2H), 5.72 (s, 2H), 5.57 (s, 2H), 4.29 (q, J=7.0 Hz, 2H), 3.91 (s, 3H), 3.62 (s, 3H), 1.42 (t, J=7.0 Hz, 3H). $^{13}$C NMR (201 MHz, DMSO-$d_6$) δ 169.51, 151.68, 150.40, 147.36, 147.23, 146.86, 133.29, 129.94, 128.85, 126.10, 125.82, 124.05, 119.41, 111.30, 108.38, 105.98, 101.54, 101.06, 68.03, 67.11, 56.04, 55.65, 31.14, 16.14. ESI-MS (ESI+) m/z: calculated 409.1281 $[M+H]^+$, found 409.1276 $[M+H]^+$.

9-(benzo[d][1,3]dioxol-5-yl)-6,7-dimethoxy-4-(prop-2-yn-1-yloxy)naphtho[2,3-c]furan-1(3H)-one (2d)-Yield: 31 mg, 56%. $^1$H NMR (500 MHz, DMSO-$d_6$) δ 7.52 (s, 1H), 7.01 (dd, J=7.9, 1.9 Hz, 1H), 6.94 (s, 1H), 6.87 (d, J=1.8 Hz, 1H), 6.74 (dd, J=7.9, 1.8 Hz, 1H), 6.10 (d, J=1.9 Hz, 2H), 5.59 (s, 2H), 5.00 (d, J=2.4 Hz, 2H), 3.93 (s, 3H), 3.70 (t, J=2.4 Hz, 1H), 3.63 (s, 3H). ESI-MS (ESI+) m/z: calculated 419.1125 $[M+H]^+$, found 419.1129 $[M+H]^+$.

9-(benzo[d][1,3]dioxol-5-yl)-6,7-dimethoxy-4-(pent-4-yn-1-yloxy)naphtho[2,3-c]furan-1(3H)-one (2e)-Yield: 36 mg, 61%. $^1$H NMR (500 MHz, DMSO-d6) δ 7.48 (s, 1H), 7.02-6.91 (m, 2H), 6.85 (d, J=1.6 Hz, 1H), 6.73 (dd, J=7.8, 1.7 Hz, 1H), 6.09 (s, 2H), 5.56 (s, 2H), 4.28 (t, J=5.9 Hz, 2H), 3.92 (s, 3H), 3.62 (s, 3H), 2.86 (t, J=2.7 Hz, 1H), 2.50-2.48 (m, 2H), 2.00 (q, J=6.5 Hz, 2H). ESI-MS (ESI+) m/z: calculated 447.1438 [M+H]$^+$, found 447.1432 [M+H]$^+$.

4-((9-(benzo[d][1,3]dioxol-5-yl)-6,7-dimethoxy-1-oxo-1,3-dihydronaphtho[2,3-c]furan-4-yl)oxy)butanenitrile (2f)-Yield: 21 mg, 36%. $^1$H NMR (500 MHz, DMSO-d6) δ 7.54 (s, 1H), 7.03-6.91 (m, 2H), 6.86 (d, J=1.7 Hz, 1H), 6.73 (dd, J=7.9, 1.7 Hz, 1H), 6.09 (s, 2H), 5.61 (s, 2H), 4.33 (t, J=5.8 Hz, 2H), 3.94 (s, 3H), 3.63 (s, 3H), 2.80 (t, J=7.0 Hz, 2H), 2.13 (q, J=6.5 Hz, 2H). ESI-MS (ESI+) m/z: calculated 448.1390 [M+H]$^+$, found 448.1287 [M+H]$^+$.

General synthetic procedure for hydrophilic phenol ether derivatives: 2a (50 mg, 0.131 mmol, 1 eq), the amine linker (2 eq), and potassium carbonate (91 mg, 0.655 mmol, 5 eq) were dissolved in dimethyl sulfoxide (6 mL). The reaction was heated to reflux overnight (16-20 h). The reaction was then cooled to room temperature and 20 mL of distilled water was added to the flask. The mixture was added to a separatory funnel and extracted with ethyl acetate (5×30 mL). The organic layers were combined and washed with brine (30 mL) before concentrating the organic layers under reduced pressure. The crude product was purified with normal phase silica gel chromatography (DCM/MeOH 100/0 to 80/20) to yield the pure solid.

9-(benzo[d][1,3]dioxol-5-yl)-6,7-dimethoxy-4-(3-morpholinopropoxy)naphtho[2,3-c]furan-1(3H)-one (2g)-Yield: 44 mg, 65%. ESI-MS (ESI+) m/z: calculated 508.1966 [M+H]$^+$, found 508.1967 [M+H]$^+$.

ethyl 2-(4-(3-((9-(benzo[d][1,3]dioxol-5-yl)-6,7-dimethoxy-1-oxo-1,3-dihydronaphtho[2,3-c]furan-4-yl)oxy)propyl)piperazin-1-yl)acetate (2h)-Yield: 6 mg, 8%. ESI-MS (ESI+) m/z: calculated 593.2493 [M+H]$^+$, found 593.2491 [M+H]$^+$.

9-(benzo[d][1,3]dioxol-5-yl)-4-(3-(4-(2-hydroxyethyl)piperazin-1-yl)propoxy)-6,7-dimethoxynaphtho[2,3-c]furan-1(3H)-one (2i)-Yield: 32 mg, 44% ESI-MS (ESI+) m/z: calculated 551.2388 [M+H]$^+$, found 551.2383 [M+H]$^+$.

9-(benzo[d][1,3]dioxol-5-yl)-6,7-dimethoxy-4-(3-(4-methylpiperazin-1-yl)propoxy)naphtho[2,3-c]furan-1(3H)-one (2j)-Yield: 14 mg, 19%. LC-MS: m/z=164.1 [M+H]$^+$.

2-amino-9-(benzo[d][1,3]dioxol-5-yl)-4-hydroxy-6,7-dimethoxy-2,3-dihydro-1H-benzo[f]isoindol-1-one (3a)-2a (200 mg, 0.526 mmol, 1 eq) and hydrazine hydrate (0.5 mL) were dissolved in 50 mL of methanol. The reaction was heated to reflux overnight (16-20 h). The solution was cooled to −20° C. and the precipitate that formed was collected. The crude product was recrystallized with ethanol to yield 136 mg (66%) of 3a as a yellow solid. ESI-MS (ESI+) m/z: calculated 395.1237 [M+H]$^+$, found 395.1240 [M+H]$^+$.

General Procedure for Hydrazone synthesis: 3a (50 mg, 0.126 mmol, 1 eq) and the select aromatic aldehyde (1.2 eq) were dissolved in methanol (10 mL). The reaction was heated to reflux overnight (16-20 h). The reaction was then cooled to room temperature and concentrated under reduced pressure. The residual solution was then cooled to −20° C. to cause the precipitate to form. The crude precipitate was collected and recrystallized with ethanol to yield the final product.

(E)-9-(benzo[d][1,3]dioxol-5-yl)-2-(benzylideneamino)-4-hydroxy-6,7-dimethoxy-2,3-dihydro-1H-benzo[f]isoindol-1-one (3b)-ESI-MS (ESI+) m/z: calculated 483.1551 [M+H]$^+$, found 483.1547 [M+H]$^+$.

(E)-9-(benzo[d][1,3]dioxol-5-yl)-4-hydroxy-6,7-dimethoxy-2-((pyridin-3-ylmethylene)amino)-2,3-dihydro-1H-benzo[f]isoindol-1-one (3c)-$^1$H NMR (300 MHz, DMSO-d$_6$) δ 10.24 (s, 1H), 8.90 (s, 1H), 8.60 (s, 1H), 8.23 (s, 1H), 8.13 (d, J=8.1 Hz, 1H), 7.67 (s, 1H), 7.56-7.45 (m, 1H), 7.06-6.91 (m, 2H), 6.86 (d, J=1.6 Hz, 1H), 6.75 (d, J=8.1 Hz, 1H), 6.11 (s, 2H), 4.88 (s, 2H), 3.93 (s, 3H), 3.64 (s, 3H), 1.90 (s, 1H). ESI-MS (ESI+) m/z: calculated 483.1503 [M+H]$^+$, found 483.1500 [M+H]$^+$.

(E)-9-(benzo[d][1,3]dioxol-5-yl)-2-((4-chlorobenzylidene)amino)-4-hydroxy-6,7-dimethoxy-2,3-dihydro-1H-benzo[f]isoindol-1-one (3d)-ESI-MS (ESI+) m/z: calculated 517.1161 [M+H]$^+$, found 517.1156 [M+H]$^+$.

(E)-9-(benzo[d][1,3]dioxol-5-yl)-2-((4-bromobenzylidene)amino)-4-hydroxy-6,7-dimethoxy-2,3-dihydro-1H-benzo[f]isoindol-1-one (3e)-

(E)-9-(benzo[d][1,3]dioxol-5-yl)-4-hydroxy-6,7-dimethoxy-2-((4-methylbenzylidene)amino)-2,3-dihydro-1H-benzo[f]isoindol-1-one (3f)-

(E)-4-(((9-(benzo[d][1,3]dioxol-5-yl)-4-hydroxy-6,7-dimethoxy-1-oxo-1,3-dihydro-2H-benzo[f]isoindol-2-yl)imino)methyl)benzonitrile (3g)-$^1$H NMR (300 MHz, DMSO-d$_6$) δ 10.22 (s, 1H), 8.17 (s, 1H), 7.65 (s, 1H), 7.01 (d, J=7.9 Hz, 1H), 6.93 (s, 1H), 6.90-6.84 (m, 1H), 6.80-6.70 (m, 1H), 6.12 (s, 2H), 4.83 (s, 2H), 3.92 (s, 3H), 3.64 (s, 3H). ESI-MS (ESI+) m/z: calculated 508.1500 [M+H]$^+$, found 508.1503 [M+H]$^+$.

(E)-9-(benzo[d][1,3]dioxol-5-yl)-4-hydroxy-6,7-dimethoxy-2-(((perfluorophenyl)methylene)amino)-2,3-dihydro-1H-benzo[f]isoindol-1-one (3h)-ESI-MS (ESI+) m/z: calculated 573.1079 [M+H]$^+$, found 573.1077 [M+H]$^+$.

(E)-9-(benzo[d][1,3]dioxol-5-yl)-2-((4-(diethylamino)benzylidene)amino)-4-hydroxy-6,7-dimethoxy-2,3-dihydro-1H-benzo[f]isoindol-1-one (3i)-(E)-9-(benzo[d][1,3]dioxol-5-yl)-2-((benzo[d][1,3]dioxol-5-ylmethylene)amino)-4-hydroxy-6,7-dimethoxy-2,3-dihydro-1H-benzo[f]isoindol-1-one (3j)-(E)-9-(benzo[d][1,3]dioxol-5-yl)-4-hydroxy-6,7-dimethoxy-2-((thiophen-2-ylmethylene)amino)-2,3-dihydro-1H-benzo[f]isoindol-1-one (3k)-(E)-9-(benzo[d][1,3]dioxol-5-yl)-4-hydroxy-6,7-dimethoxy-2-((4-(trifluoromethyl)benzylidene)amino)-2,3-dihydro-1H-benzo[f]isoindol-1-one (3l)-

General synthesis of ring-opened diphyllin amide synthesis-4a (50 mg, 0.131 mmol, 1 eq) and the amine component (2 eq) were dissolved in a 0.5M NaOH in MeOH solution (5 mL). The reaction was heated to reflux overnight (16-20 h). The reaction was then cooled to room temperature and the solvent was removed under reduced pressure. The reaction was then suspended in 10 mL of distilled water and the pH was adjusted to 7. The solution was then added to a separatory funnel and extracted with ethyl acetate (3×30 mL). The organic layers were combined and washed with distilled water (30 mL) and brine (30 mL) before being concentrated under reduced pressure. The crude product was purified using normal phase silica gel chromatography (DCM/MeOH 100/0 to 80/20) to yield the final product.

(1-(benzo[d][1,3]dioxol-5-yl)-4-hydroxy-3-(hydroxymethyl)-6,7-dimethoxynaphthalen-2-yl)(piperidin-1-yl)methanone (4a)-(1-(benzo[d][1,3]dioxol-5-yl)-4-hydroxy-3-(hydroxymethyl)-6,7-dimethoxynaphthalen-2-yl)(morpholino)methanone (4b)-(1-(benzo[d][1,3]dioxol-5-yl)-4-hydroxy-3-(hydroxymethyl)-6,7-dimethoxynaphthalen-2-yl)(4-methylpiperazin-1-yl)methanone (4c)-(1-(benzo[d][1,3]dioxol-5-yl)-4-hydroxy-3-(hydroxymethyl)-6,7-dimethoxynaphthalen-2-yl)(piperazin-1-yl)methanone (4d)-1-(benzo[d][1,3]dioxol-5-yl)-N-cyclopentyl-4-hydroxy-3-(hydroxymethyl)-6,7-dimethoxy-2-naphthamide (4e)-Yield: 21 mg, 19%. $^1$H NMR (500 MHz, DMSO-d$_6$) 7.50 (s, 1H), 6.91 (s, 1H), 6.75 (s, 1H), 6.73 (s, 1H), 6.675 (d, J=5 Hz, 1H), 6.03 (d, J=20 Hz, 2H), 4.03 (2H, s), 3.84 (3H, s), 3.56

(3H, s), 3.31 (b, too many protons), 3.21 (1H, s, b), 1.84 (2H, m), 1.64 (2H, m), 1.5 (4H, m). LC-MS: m/z=466.12 [M+H]⁺.

Parts of this disclosure has been published, Aaron Lindstrom, et al., "Phenotypic Prioritization of Diphyllin Derivatives That Block Filoviral Cell Entry by Vacuolar (H+)-ATPase", *Chem Med Chem,* 2018, 13(24), 2664-2676, the contents of which are incorporated herein by reference in its entirety.

Those skilled in the art will recognize that numerous modifications can be made to the specific implementations described above. The implementations should not be limited to the particular limitations described. Other implementations may be possible.

While the inventions have been illustrated and described in detail in the drawings and foregoing description, the same is to be considered as illustrative and not restrictive in character, it being understood that only certain embodiments have been shown and described and that all changes and modifications that come within the spirit of the invention are desired to be protected. It is intended that the scope of the present methods and apparatuses be defined by the following claims. However, it must be understood that this disclosure may be practiced otherwise than is specifically explained and illustrated without departing from its spirit or scope.

The invention claimed is:

1. A compound having a formula

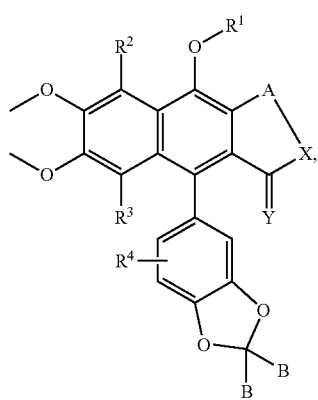

(I)

or a pharmaceutically acceptable salt thereof, wherein
A is $CR_2$, $CH_2$, S, NH, NR, wherein R is alkyl;
B is hydrogen (H), deuterium (D), or fluorine (F);
X is C=O, $CR_2$, $CH_2$, CHR, S, NH, NR, wherein R is unsubstituted alkyl;
Y is O, $CF_2$, $CH_2$, CHR, S, NH, NR, wherein R is an alkyl;
$R^1$ is hydrogen, alkyl, alkylamide, alkenyl, alkenylamide, alkenylamino, alkynyl, alkynylamide, alkynylamino, heterocyclyl, cycloalkyl, cycloalkenyl, acyl, aryl, heteroaryl, arylalkyl, arylalkenyl, or arylalkynyl;
$R^2$, $R^3$, and $R^4$ are each independently selected from the group consisting of hydrogen, deuterium, —CN, and a halo.

2. The compound according to claim 1, wherein $R^1$ is

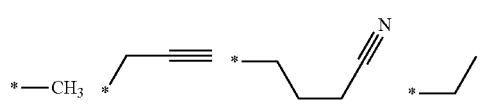

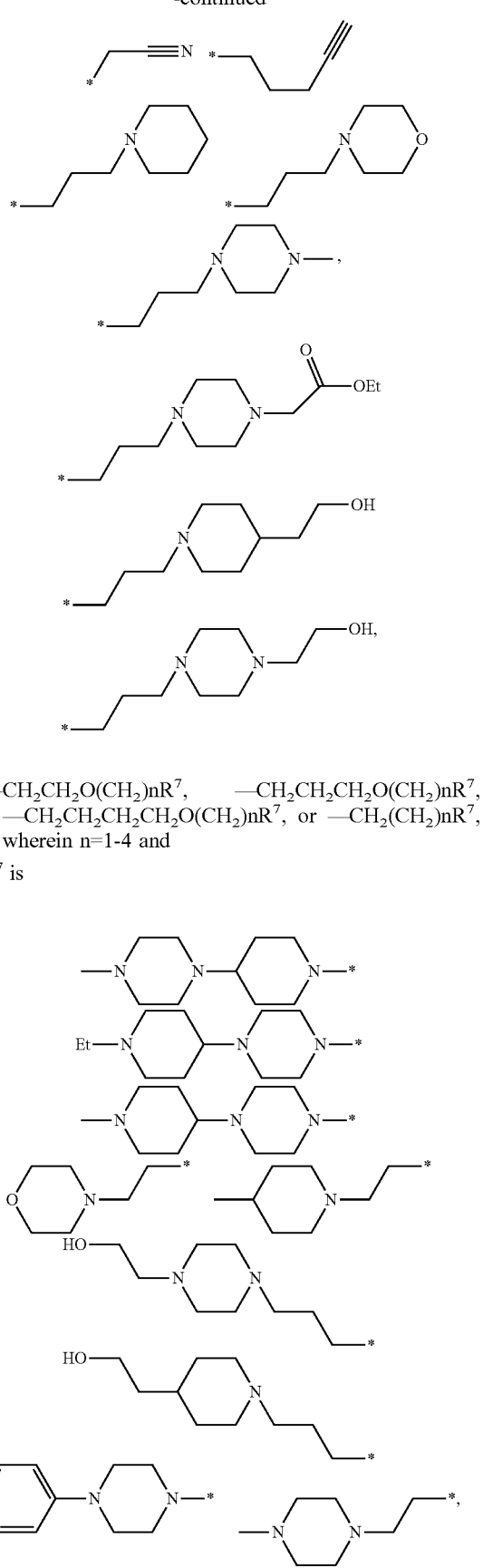

—$CH_2CH_2O(CH_2)nR^7$, —$CH_2CH_2CH_2O(CH_2)nR^7$,
—$CH_2CH_2CH_2CH_2O(CH_2)nR^7$, or —$CH_2(CH_2)nR^7$,
wherein n=1-4 and
$R^7$ is

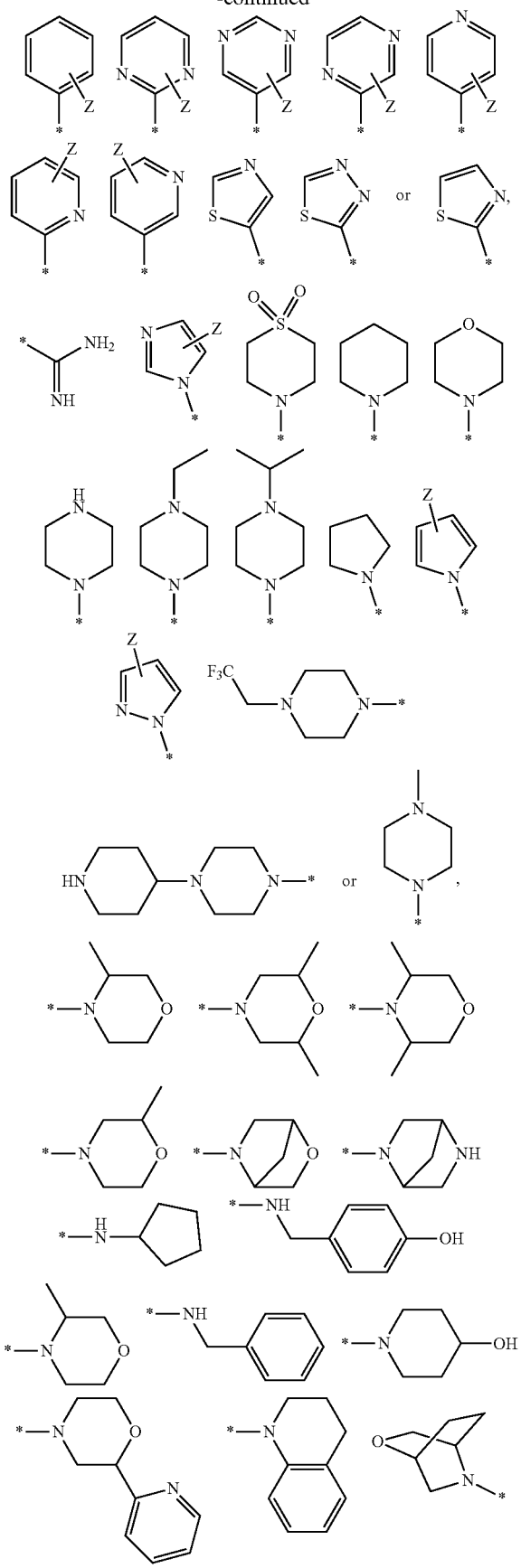
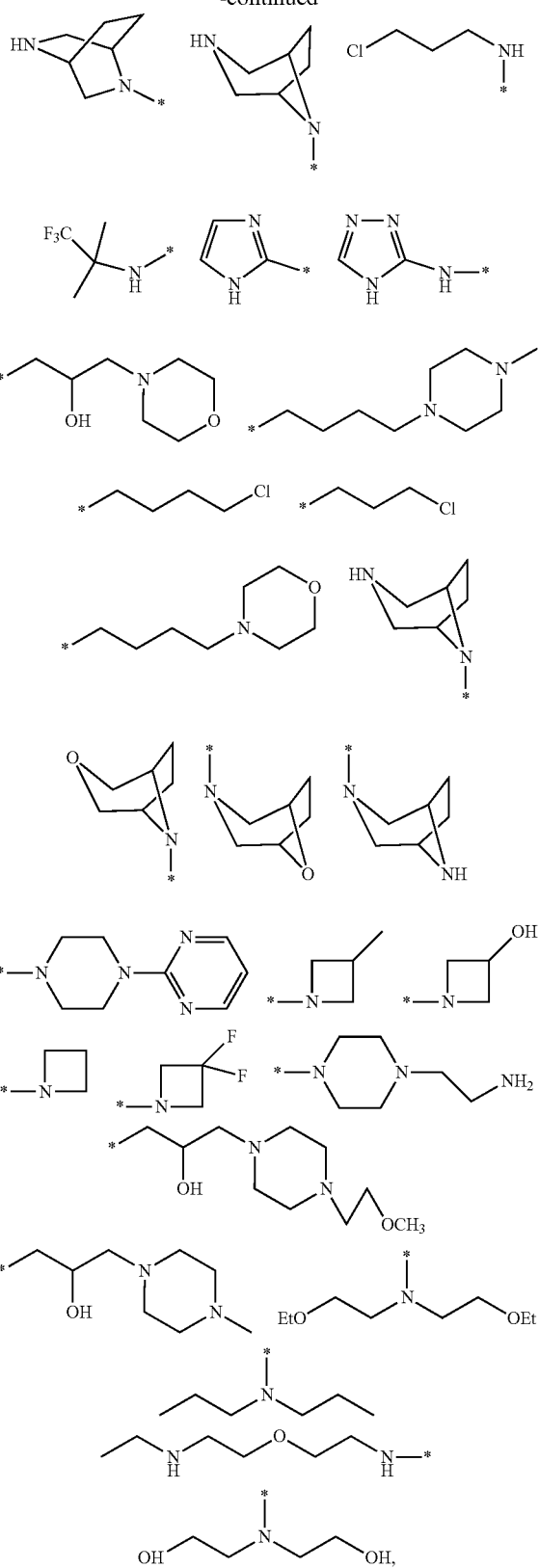
wherein Z is a halogen, C1~C3 alkyl, —CF$_3$, —CN, or —CONR$_2$, wherein R is hydrogen or a C1~C3 alkyl, and * represents site of attachment.

3. The compound according to claim 1, wherein the compound has the following formula:

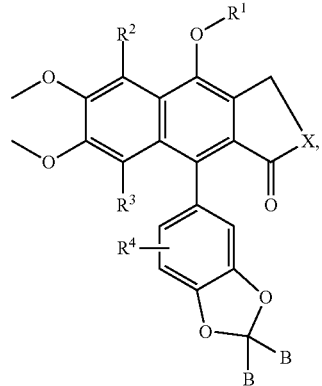
(II)

or a pharmaceutically acceptable salt thereof, wherein
B is hydrogen (H), deuterium (D), or fluorine (F);
X is CR$_2$, CH$_2$, CHR, S, NH, or NR, wherein R is alkyl;
R$^2$, R$^3$, and R$^4$ are each independently selected from the group consisting of hydrogen, deuterium, —CN, —CF$_3$, and a halo; and
R$^1$ is

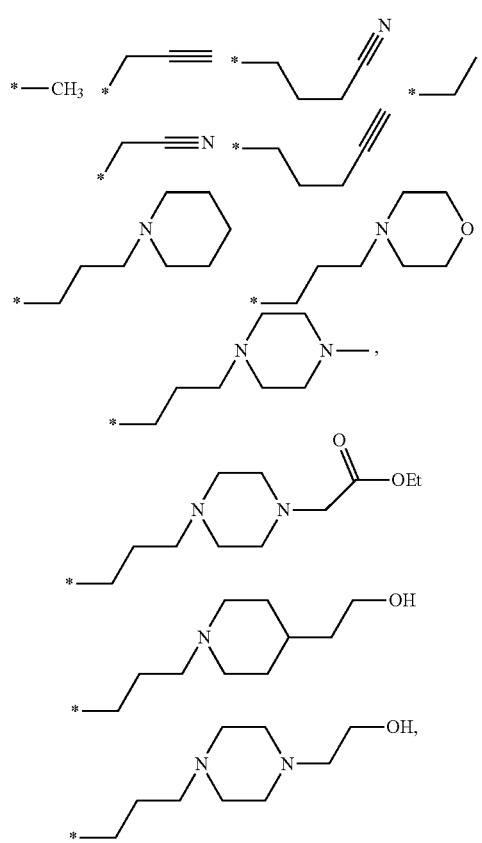

—CH$_2$CH$_2$O(CH$_2$)nR$^7$, —CH$_2$CH$_2$CH$_2$O(CH$_2$)nR$^7$, —CH$_2$CH$_2$CH$_2$CH$_2$O(CH$_2$)nR$^7$, or —CH$_2$(CH$_2$)nR$^7$, wherein n=1-4 and R$^7$ is

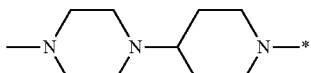
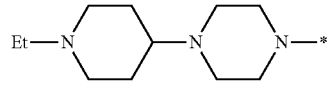
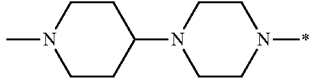
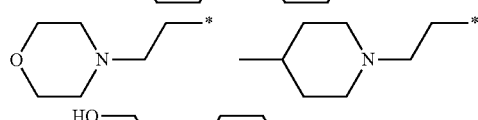
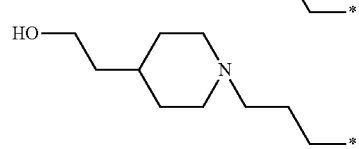
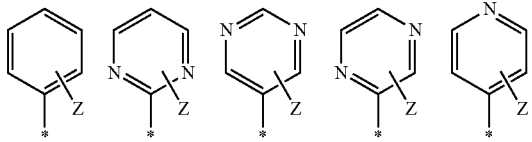
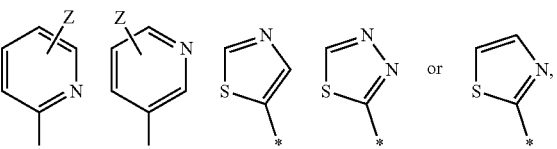
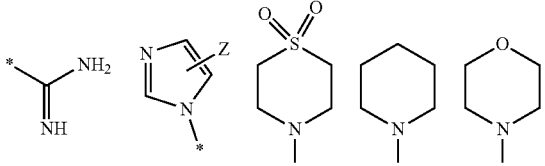
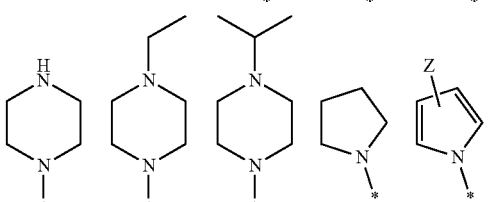
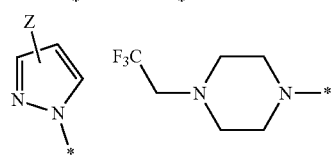

wherein Z is halogen, C1–C3 alkyl, —CF₃, —CN, or —CONR₂, wherein R is hydrogen or C1C3 alkyl, and * represents site of attachment.

4. The compound according to claim 1, wherein B is deuterium and R², R³, and R⁴ are hydrogen.

5. The compound according to claim 1, wherein B is fluorine (F); and R², R³, and R⁴ are hydrogen.

6. The compound according to claim 1, wherein B, R², R³, and R⁴ are hydrogen.

7. A pharmaceutical composition comprising one or more compounds of claim 1, or a pharmaceutically acceptable salt thereof, together with one or more diluents, excipients or carriers.

8. A method for treating a patient with an infection with Ebola virus or Marburg virus, comprising the step of administering a therapeutically effective amount of one or more compounds, together with one or more carriers, diluents, or excipients, to a patient in need of relief from said infection, the compound having formula (I):

or a pharmaceutically acceptable salt thereof, wherein
A is CR₂, CH₂, S, NH, or NR, wherein R is alkyl;
B is hydrogen (H), deuterium (D), or fluorine (F);
X is CR₂, CH₂, CHR, S, NH, or NR, wherein R is unsubstituted alkyl;
Y is O, CF₂, CH₂, CHR, S, NH, or NR, wherein R is an alkyl;

$R^1$ is hydrogen, alkyl, alkylamide, alkenyl, alkenylamide, alkenylamino, alkynyl, alkynylamide, alkynylamino, heterocyclyl, cycloalkyl, cycloalkenyl, acyl, aryl, heteroaryl, arylalkyl, arylalkenyl, or arylalkynyl;

$R^2$, $R^3$, and $R^4$ are each independently selected from the group consisting of hydrogen, deuterium, —CN, and a halo.

9. The method according to claim 8, wherein said compound has a formula

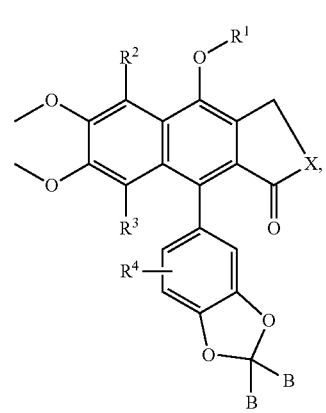

(II)

or a pharmaceutically acceptable salt thereof, wherein

B is hydrogen (H), deuterium (D), or fluorine (F);

X is $CR_2$, $CH_2$, CHR, S, NH, or NR, wherein R is alkyl;

$R^2$, $R^3$, and $R^4$ are each independently selected from the group consisting of hydrogen, deuterium, —CN, and a halo; and $R^1$ is

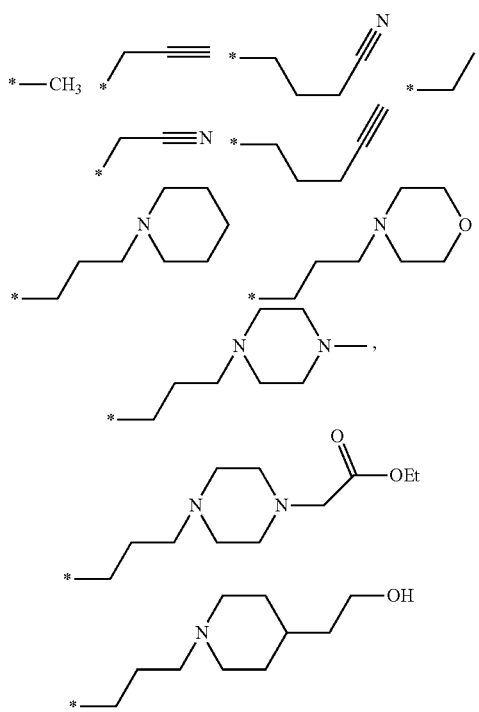

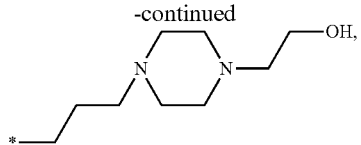

$CH_2CH_2O(CH_2)nR^7$, —$CH_2CH_2CH_2O(CH_2)nR^7$, —$CH_2CH_2CH_2CH_2O(CH_2)nR^7$, or —$CH_2(CH_2)nR^7$, wherein n=1~4 and $R^7$ is

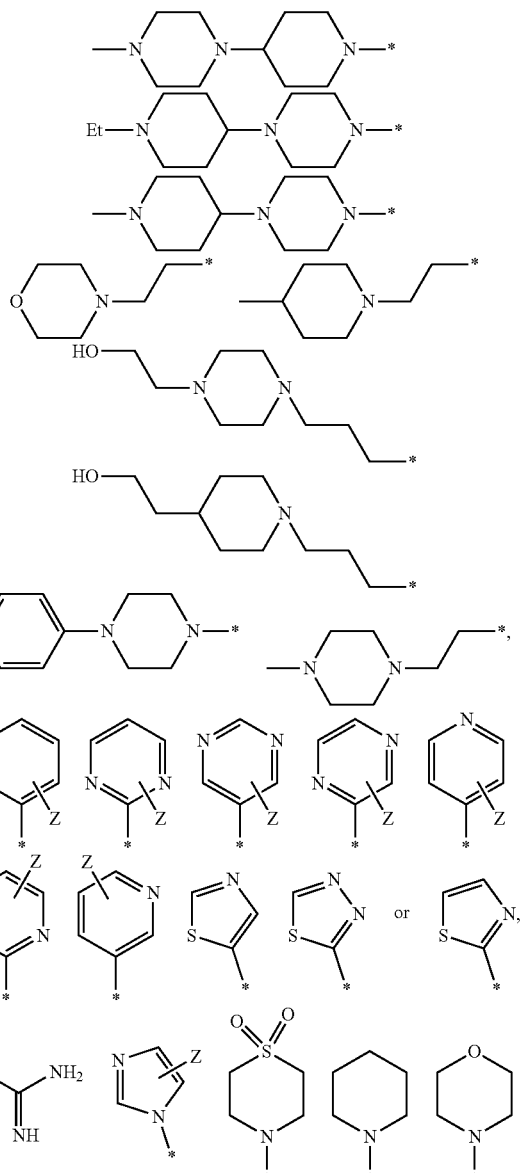

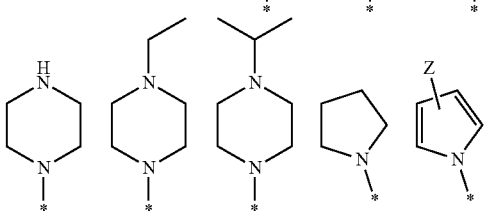

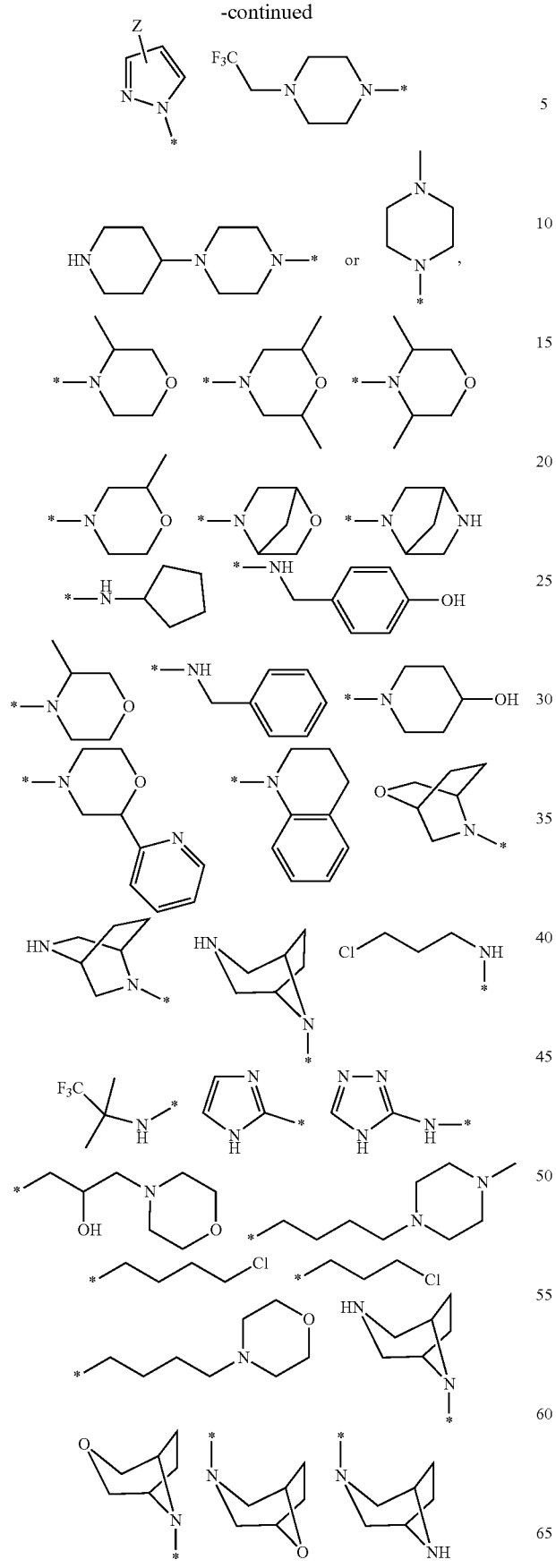

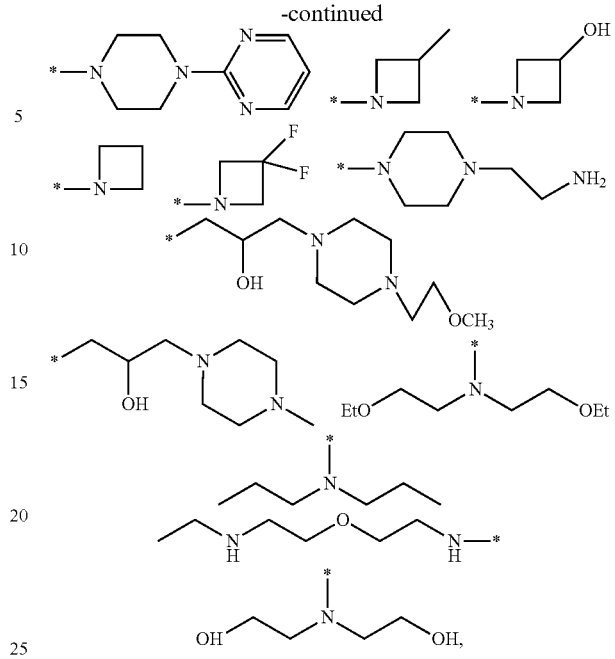

wherein Z is halogen, C1~C3 alkyl, —CF₃, —CN, or —CONR₂, wherein R is hydrogen or C1~C3 alkyl, and * represents site of attachment.

10. A compound of formula (I):

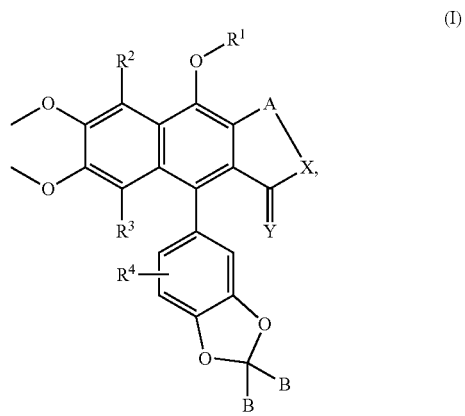

(I)

or a pharmaceutically acceptable salt thereof, wherein
A is CH₂;
B is hydrogen (H), deuterium (D), or fluorine (F);
X is O or S;
Y is O, CF₂, CH₂, CHR, S, NH, or NR, wherein R is an alkyl;
$R^1$ is

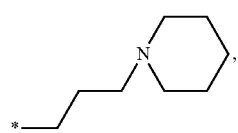 [SMILES: *CCCN1CCCCC1]

—CH₂CH₂O(CH₂)nR⁷, —CH₂CH₂CH₂O(CH₂)nR⁷, —CH₂CH₂CH₂CH₂O(CH₂)nR⁷, or —CH₂(CH₂)nR⁷, wherein n=1-4;

97
$R^2$, $R^3$, and $R^4$ are each independently selected from the group consisting of hydrogen, deuterium, —CN, —$CF_3$, and halo;
$R^7$ is
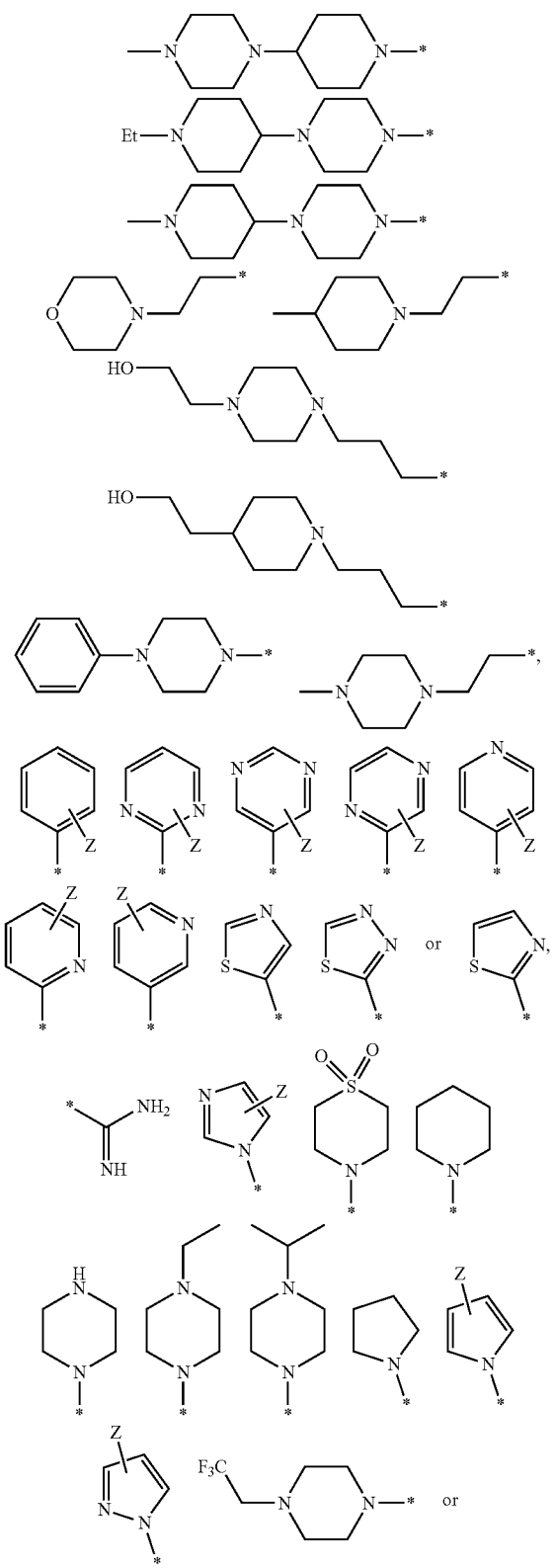
98
-continued
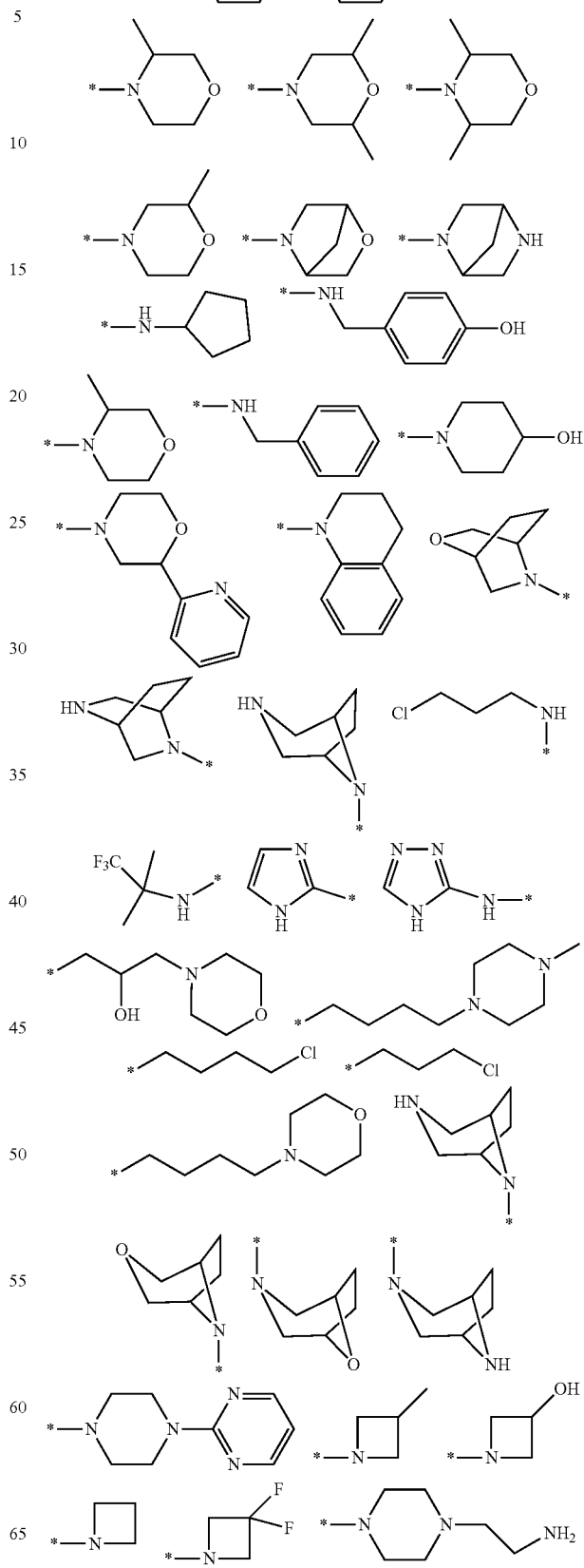

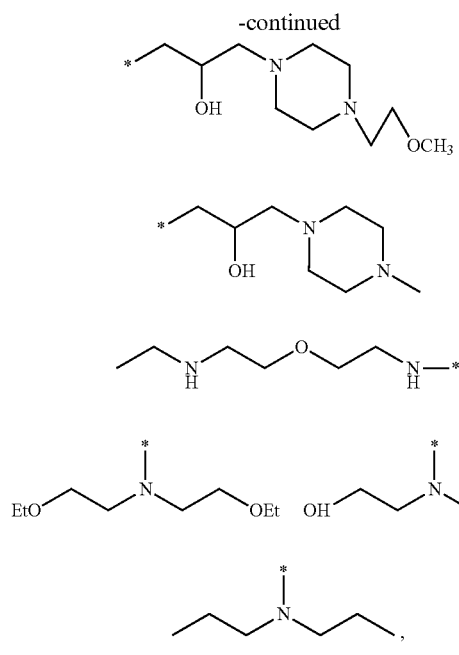
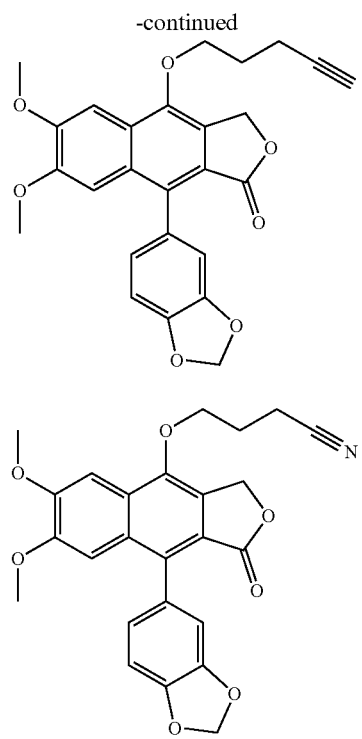
wherein Z is halogen, C1~C3 alkyl, —CF₃, —CN, or —CONR₂, wherein R is hydrogen or C1~C3 alkyl, and * represents site for Attachment.
11. The compound of claim 10, wherein the compound of formula (I) is a compound of formula (III),
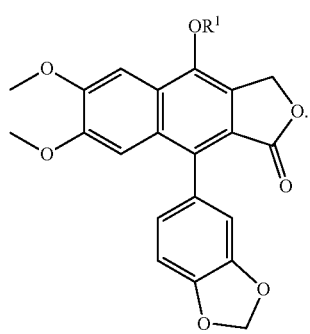
(III)
12. A compound selected from:
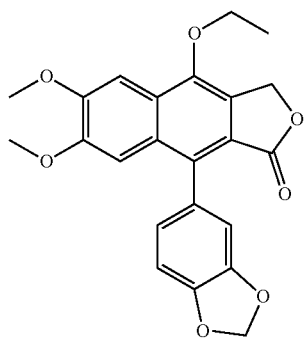
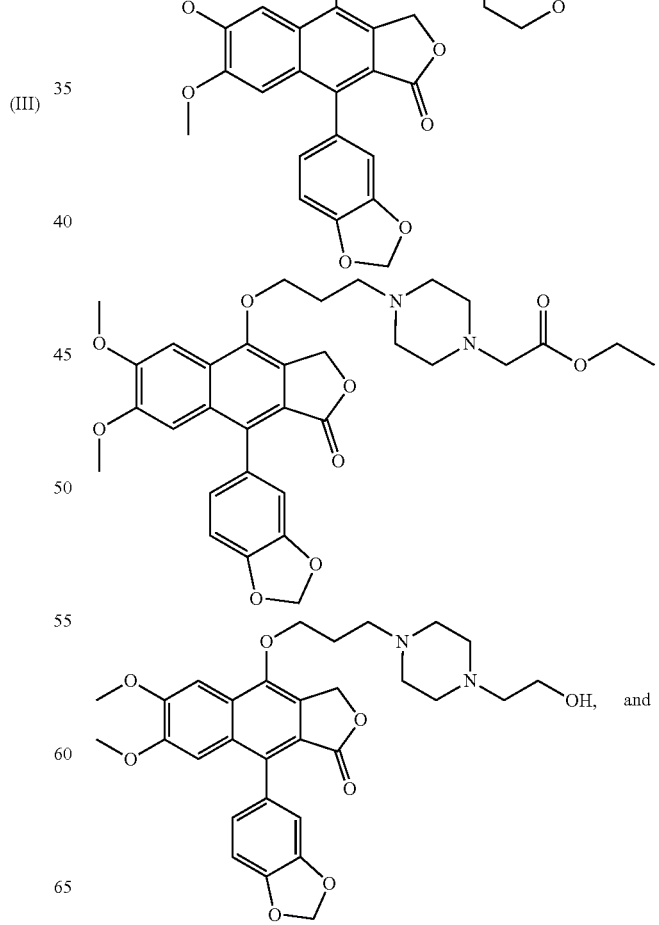

-continued

[chemical structure]

13. A compound having a formula (I)

[chemical structure]

or a pharmaceutically acceptable salt thereof, wherein
A is C=O, CR$_2$, S, NH, NR, wherein R is alkyl;
B is hydrogen (H), deuterium (D), or fluorine (F);
X is C=O, CR$_2$, CH$_2$, CHR, O, S, NH, NR, wherein R is unsubstituted alkyl;
Y is O, CF$_2$, CH$_2$, CHR, S, NH, NR, wherein R is an alkyl;
R$^1$ is hydrogen, alkyl, alkylamide, alkenyl, alkenylamide, alkenylamino, alkynyl, alkynylamide, alkynylamino, heterocyclyl, cycloalkyl, cycloalkenyl, heterocycloalkyl, aryl, heteroaryl, arylalkyl, arylalkenyl, or arylalkynyl;
R$^2$, R$^3$, and R$^4$ are each independently selected from the group consisting of hydrogen, deuterium, —CN, —CF$_3$, and halo.

14. A method for treating a patient with an infection with Ebola virus or Marburg virus, comprising the step for Administering a therapeutically effective amount of one or more compounds, together with one or more carriers, diluents, or excipients, to a patient in need of relief (I)

[chemical structure]

from said infection, the compound having formula (I):
or a pharmaceutically acceptable salt thereof, wherein
A is CH$_2$;
B is hydrogen (H), deuterium (D), or fluorine (F);
X is O or S;
Y is O, CF$_2$, CH$_2$, CHR, S, NH, or NR, wherein R is alkyl;
R$^1$ is alkylamide, alkenylamide, alkenylamino, alkynylamide, alkynylamino, cycloalkyl, cycloalkenyl, aryl, heteroaryl, or arylalkenyl; and
R$^2$, R$^3$, and R$^4$ are each independently selected from the group consisting of hydrogen, deuterium, —CN, and halo.

* * * * *